United States Patent
Kumagai et al.

(10) Patent No.: US 6,426,185 B1
(45) Date of Patent: *Jul. 30, 2002

(54) METHOD OF COMPILING A FUNCTIONAL GENE PROFILE IN A PLANT BY TRANSFECTING A NUCLEIC ACID SEQUENCE OF A DONOR PLANT INTO A DIFFERENT HOST PLANT IN AN ANTI-SENSE ORIENTATION

(75) Inventors: Monto H. Kumagai, Davis; Guy R. della-Cioppa, Vacaville; Robert L. Erwin, Vacaville; David R. McGee, Vacaville, all of CA (US)

(73) Assignee: Large Scale Biology Corporation, Vacaville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/359,301

(22) Filed: Jul. 21, 1999

Related U.S. Application Data

(63) Continuation-in-part of application No. 09/232,170, filed on Jan. 15, 1999, which is a continuation-in-part of application No. 09/008,186, filed on Jan. 16, 1998.

(51) Int. Cl.[7] ............... C12Q 1/68; C12P 19/34; C12N 15/82; C07H 21/02; C07H 21/04
(52) U.S. Cl. ............. 435/6; 435/91.1; 435/468; 536/23.1; 536/23.6; 536/23.72; 536/24.1; 536/24.5
(58) Field of Search .............. 435/6, 468, 69.1, 435/69.2, 91.1, 91.32; 536/23.1, 23.6, 24.3, 24.5

(56) References Cited

U.S. PATENT DOCUMENTS

| | | |
|---|---|---|
| 4,373,071 A | 2/1983 | Itakura |
| 4,401,796 A | 8/1983 | Itakura |
| 4,415,732 A | 11/1983 | Caruthers et al. |
| 4,458,066 A | 7/1984 | Caruthers et al. |
| 4,500,707 A | 2/1985 | Caruthers et al. |
| 4,668,777 A | 5/1987 | Caruthers et al. |
| 4,683,195 A | 7/1987 | Mullis et al. |
| 4,683,202 A | 7/1987 | Mullis |
| 4,885,248 A | 12/1989 | Ahlquist |
| 4,973,679 A | 11/1990 | Caruthers et al. |
| 5,047,524 A | 9/1991 | Andrus et al. |
| 5,132,418 A | 7/1992 | Caruthers et al. |
| 5,143,854 A | 9/1992 | Pirrung et al. |
| 5,153,319 A | 10/1992 | Caruthers et al. |
| 5,173,410 A | 12/1992 | Ahlquist |
| 5,262,530 A | 11/1993 | Andrus et al. |
| 5,312,910 A | 5/1994 | Kishore et al. |
| 5,316,931 A | 5/1994 | Donson et al. |
| 5,412,087 A | 5/1995 | McGall et al. |
| 5,466,788 A | 11/1995 | Ahlquist et al. |
| 5,489,678 A | 2/1996 | Fodor et al. |
| 5,491,076 A | 2/1996 | Carrington et al. |
| 5,500,360 A | 3/1996 | Ahlquist et al. |
| 5,571,639 A | 11/1996 | Hubbell et al. |
| 5,589,367 A | 12/1996 | Donson et al. |

(List continued on next page.)

FOREIGN PATENT DOCUMENTS

| | | |
|---|---|---|
| WO | WO 91/01375 A | 2/1991 |
| WO | WO 94/10329 | 5/1994 |
| WO | WO 95/34668 | 12/1995 |
| WO | WO 96/04393 | 2/1996 |
| WO | WO 96/06111 | 2/1996 |
| WO | WO 97/04112 | 2/1997 |
| WO | WO 97/04113 | 2/1997 |
| WO | WO 97/10328 | 3/1997 |
| WO | WO 97/32024 | 9/1997 |

(List continued on next page.)

OTHER PUBLICATIONS

Branch, A. Trends in Biochem. Sci. (TIBS), vol. 23, pp. 45–50, 1998.*
Crooke, S.T. Antisense Res. and Application, Chapter 1, pp. 1–50, Publi. Springer–Verlag, 1998.*
Fields et al, editors, Fundamental Virology, pp. 370–371, Publi. Lippincott–Raven, 1996.*
Abramson, et al., Current Opinion Biotechnology 4:41–47 (1993).
Agapov, E., et al., "Noncytopathic Sinbis virus RNA vectors for heterologous gene expression," *Proc. Natl. Acad. Sci. USA* 95: 12989–12994 (1998).
Ahlquist, et al., "Complete Nucleotide Sequence of Brome Mosaic Virus RNA3," *J. Mol. Biol.* 153:23–38 (1981).
Ahlquist, D., et al., "Multicomponent RNA plant virus infection derived from cloned viral cDNA," *Proc. Natl. Acad. Sci. USA* 81:7066–7070 (1984).

(List continued on next page.)

*Primary Examiner*—Andrew Wang
*Assistant Examiner*—Jane Zara
(74) *Attorney, Agent, or Firm*—Albert P. Halluin; Viola T. Kung; Thomas Gallegos

(57) ABSTRACT

The present invention provides a method of compiling a plant functional gene profile, a method of changing the phenotype or biochemistry of a plant, a method of determining a change in phenotype or biochemistry of a plant, and a method of determining the presence of a trait in plant. The methods comprise expressing transiently a nucleic acid sequence of a plant into a host plant to affect phenotypic or biochemical changes in the host plant. A viral vector functional genomic screen has been developed to identify nucleotide sequences in transfected plants by systemically knocking out endogenous gene expression in an antisense mechanism. Once the presence of a trait in a plant is identified by phenotypic or biochemical changes in the host plant, the nucleic acid insert in the cDNA clone or in the vector that results in the changes is then sequenced. The present invention exemplifies that genes encoding GTP binding proteins in one plant can silence endogenous gene expression in a different plant.

14 Claims, 15 Drawing Sheets

U.S. PATENT DOCUMENTS

| | | |
|---|---|---|
| 5,602,242 A | 2/1997 | Ahlquist et al. |
| 5,605,793 A | 2/1997 | Stemmer |
| 5,618,699 A | 4/1997 | Hamamoto et al. |
| 5,627,060 A | 5/1997 | Ahlquist et al. |
| 5,629,175 A | 5/1997 | Goodman et al. |
| 5,633,447 A | 5/1997 | Ahlquist et al. |
| 5,700,642 A | 12/1997 | Monforte et al. |
| 5,714,313 A | 2/1998 | Garfinkel et al. |
| 5,716,802 A | 2/1998 | Sijmons et al. |
| 5,723,755 A | 3/1998 | Fortin |
| 5,744,305 A | 4/1998 | Fodor et al. |
| 5,811,238 A | 9/1998 | Stemmer et al. |
| 5,811,653 A | 9/1998 | Turpen |
| 5,830,721 A | 11/1998 | Stemmer et al. |
| 5,834,252 A | 11/1998 | Stemmer et al. |
| 5,837,458 A | 11/1998 | Minshull et al. |
| 5,866,785 A | 2/1999 | Donson et al. |
| 5,889,165 A | 3/1999 | Fodor et al. |
| 5,889,190 A | 3/1999 | Donson et al. |
| 5,891,665 A | 4/1999 | Wilson |
| 5,899,191 A | 5/1999 | Turpen |
| 5,922,602 A | 7/1999 | Kumagai et al. |
| 5,977,438 A | 11/1999 | Turpen et al. |
| 6,037,456 A | 3/2000 | Garger et al. |

FOREIGN PATENT DOCUMENTS

| | | |
|---|---|---|
| WO | WO 97/37014 | 10/1997 |
| WO | WO 97/40178 | 10/1997 |
| WO | WO 97/42210 | 11/1997 |
| WO | WO 98/07886 | 2/1998 |
| WO | WO 98/13487 | 4/1998 |
| WO | WO 98/27230 | 6/1998 |
| WO | WO 98/31837 | 7/1998 |
| WO | WO 98/36083 A | 8/1998 |
| WO | WO 99/06593 | 2/1999 |
| WO | WO 99/07888 | 2/1999 |

OTHER PUBLICATIONS

Allison, R., et al., "Regeneration of a functional RNA virus genome by recombination between deletion mutants and requirement for cowpea chlorotic mottle virus 3a and coat genes for systemic infection," *Proc. Natl. Acad. Sci. USA* 87(5): 1820–1824 (1990).

Alwine, et al., "Method for detection of specific RNAs in agarose gels by transfer to diazobenzyloxymethyl–paper and hybridization with DNA probes," *Proc. Natl. Acad. Sci. USA* 74(12:5350–5354 (1977).

Angell, S. M. et al., "Consistent gene silencing in transgenic plants expressing a replicating potato virus X RNA," *EMBO Journal 16* (12):3675–3684 (1997).

Arkin, et al., *Proc. Natl. Acad. Sci. USA* 89:7811–7815 (1992).

Armstrong, et al., "Conserved enzymes mediate the early reactions of carotenoids biosynthesis in nonphotosynthetic and photosynthetic prokaryotes," *Proc. Natl. Acad. Sci. USA* 87:9975–9979 (1990).

Armstrong, et al., "Genetic and Biochemical Characterization of Carotenoid Biosynthesis Mutants of *Rhodobacter capsulatus*," *J. Biol. Chem.* 265:8329–8338 (1990).

Arnold, "Design by Directed Evolution," *Acc. Chem. Res.* 31:125–131 (1998).

Arnold, *Proc. Natl. Acad. Sci. USA* 95:2035–2036 (1998).

Aslanidis, et al., "Ligation–independent cloning of PCR products (LIC–PCR)," *Nucleic Acids Research* 18(20):6069–6074 (1990).

Aslanidis, et al., "Minimal Length Requirement of the Single–stranded Tails for Ligation–independent Cloning (LIC) of PCR Products," *PCR Methods Appl.* 4:172–177 (1994).

Ausubel, F., et al., *Current Protocols in Molecular Biology*, Green Publishing and Wiley–Interscience, NY (1987).

Baldwin, I.T., "Jasmonate–induced responses are costly but benefit plants under attacl in native populations," *Proc. Natl. Acad. Sci. USA* 95(14):8113–8118 (1998).

Baulcombe, "fast forward genetics based on virus–induced gene silencing", *Current Opinion In Plant Biology*, 2:109–113.

Baulcombe, "RNA as a target and an initiator of post–transcriptional gene silencing in transgenic plants," *Plant Mol. Biol.* 32:79–88 (1996).

*Biotechnology* 11:1548–1552 (1993).

Bisaro, D., et al., "Genetics Analysis of Tomato Golden Mosaic Virus," *Current Communications in Molecular Biology: Viral Victors*, Guzman, Y., Editor, Cold Spring Harbor Laboratory, pp. 172–189 (1988).

Black, et al., *Proc. Natl. Acad.. Sci. USA* 93:3525–3529 (1996).

Bobak, et al., *Proc. Natl. Acad. Sci. USA* 86:6101–6105 (1989).

Braun, et al., *Nature* 391:775–778 (1998).

Brisson, et al., "[46] Plant Virus Vectors: Cauliflower Mosaic Virus," *Methods in Enzymology* 118:659–668 (1986).

Brock, et al., *Biology of Microorganisms*, Prentice–Hall, Inc. Upper Saddle River, NJ, pp. 263–284 (1997).

Buchman, et al., *Focus* 14:41–45 (1992).

Bulyk, et al., "Quantifying DNA–protein interactions by double–stranded DNA arrays," *Nature Biotechnology*, 17:573–577 (1999).

Cadwell, et al., *PCR Methods App.* 3:S136–40 (1994).

Cadwell, et al., *PCR Methods App.* 2:28–33 (1992).

Camara, B., "[32] Plant Phyoene Synthase Complex: Component Enzymes, Immunology, and Biogenesis," *Methods in Enzymol.* 214:352–365 (1993).

Carrington, et al.,.

Cease, et al., "A Vector for Facile PCR Product Cloning and Modification Generating Any Desxired 4–Base 5' Overhang: pRPM," *Biotechniques*, 14:250–255 (1993).

Chang, G–J. and Trent, D., "Nucleotide Sequence of the Genome Region Encoding the 26S mRNA of Eastern Equine Encephalomyelitis Virus and the Deduced Amino Acid Sequence of the Viral Structural Proteins," *J. Gen. Virol.* 68:2129–2142 (1987).

Chittenden, T., et al., "Regulated Republication of an Episomal Simian Virus 40 Origin Plasmid in COS7 Cells," *J. Virol.* 65(11):5944–5951 (1991).

Christians, et al., "Directed evolutionof thymidine kinase for AZT phosphorylation using DNA family shuffling", *Nat. Biotechnol.* 17:259–264 (1999).

Cillo, et al., "Homeobox Genes and Cancer," *Exp. Cell Res.*, 248:1–9 (1999).

Cleland, et al., *Protein Engineering: Principles and Practice*, Wiley–Liss (1996).

Condreay, et al., *Proc. Natl. Acad. Sci. USA*, 96:127–132 (1999).

Couto, et al., "Cloning and Sequence Analysis of Human Breast Epithelian Antigen BA46 Reveals and RGD Cell Adhesion Sequence Presented on an Epidermal Growth Facor–Like Domain," *DNA Cell Biology* 15:281–286 (1996).

Crameri, A., et al., "Improved Green Fluorescent Protein by Molecular Evolution Using DNA Shuffling," *Nature Biotech.* 14:315–319 (1996).

Crameri, A., et al., "Molecular evolution of an arsenate detoxification pathway by DNA shuffling," *Nature Biotech.* 15:436–438 (1997).

Crameri, et al., "DNA shuffling of a family of genes from diverse species accelerates directed evolution," *Nature* 391:288–291.

Crameri, et al., *Nature Medicine* 2:100–103 (1996).

*Curr. Opin. Biotechnol* 6(1):30–36 (1995).

*Curr. Opin. Cell Biol.* 7:399–405 (1995).

Dallman, et al., "Molecular characterization of tobacco cDNAs encoding two small GTP–binding proteins," *Plant Molecular Biol.* 19:847–857 (1992).

Davis, N., et al., "A Viral Vaccine Vector That Expresses Foreign Genes in Lymph Nodes and Protects against Mucosal Challenge," *J. Virol.* 70(6):3781–3787 (1996).

Dawson, et al., "A Tobacco Mosaic Virus–Hybrid Expresses and Loses an Added Gene," *Virology* 172:285–292 (1989).

Dawson, et al., "cDNA cloning of the complete genome of tobacco mosaic virus and production of infectious transcripts," *Proc. Natl. Acad. Sci. USA* 83:1832–1836 (1986).

Dawson, W., et al., "Regulation of Tobamovirus Gene Expression," *Advances in Virus Res*, 38:307–342 (1990).

Delagrave, et al., *Biotechnology* 11:1548–1552 (1993).

Della–Cioppa, et al., "Genetic Engineering of herbicide resistance in plants," *Frontiers of Chemistry: Biotechnology*, Chemical Abstract Service, ACS, Columbus, OH, pp. 665–670 (1989).

Deom, et al., "The 30–Kilodalton Gene Product of Tobacco Mosaic Virus Potentiates Virus Movement," *Science* 237:389–394 (1987).

DeRisi, et al., "Exploring the Metabolic and Genetic Control of Gene Expression on a Genomic Scale," *Science* 278:680–686 (1997).

Dietmaier, et al., "DISEC–TRISEC: di and–trinucleotide–sticky–end closing of PCR–amplified DNA," *Nucleic Acids Res.* 21:3603–3604 (1993).

Dijkstra, et al., *Practical Plant Virology: Protocols and Exercises*, Springer Verlag (1998).

*DNA Cloning*, D.M. Clover, Ed., IRL Press, Oxford (1985).

Donson, et al., "Agrobacterium–Mediated Infectivity of Cloned Digitaria Streak Virus DNA," *Virology* 162:248–250 (1988).

Dougherty and Parks, "Transgenes and gene suppression: telling us something new?" *Current Biology Ltd.* 7:399–405 (1995).

Duechler, et al., "Evolutionary relationships within the human rhinovirus genus: Comparison of serotypes 89, 2, and 14," *Proc. Natl. Acad. Sci. USA* 84:2605–2609 (1987).

Eckert, et al., *PCR Methods App.* 1:17–24 (1991).

Elmer, et al., "Agrobacterium–mediated inoculation of plants with tomato golden mosaic virus DNAs," *Plant Mol. Biol.* 10:225–234 (1988).

Flasinski, S., et al., "Mutational analysis of the Coat Protein Gene of Brome Mosaic Virus: Effects on Replication and Movement in Barley and in *Chenopodium hybridum*," *Mol. Plant Microbe Interact* 8(1):23–31 (1995).

Flasinski, S., et al., "Structure–Based Rationale for the Rescue of Systemic Movement of Brome Mosaic Virus by Spontaneous Second–Site Mutations in the Coat Protein Gene," *J. Virol.* 71(3):2500–2504 (1997).

Fray, et al., "Identification and genetic analysis of normal and mutant phytoene synthase genes of tomato by sequencing, complementation and co–suppression," *Plant Mol. Biol.* 22:589–602 (1993).

French, et al., "Bacterial Gene Inserted in an Engineered RNA Virus: Efficient Expression in Monocotyledonous Plant Cells," *Science* 231:1294–1297 (1986).

Frolov, I., et al., "Sindbis Virus Replicons and Sindbis Virus: Assembly of Chimeras and of Particles Deficient in Virus RNA," *J. Virol.* Apr. 71(4):2819–2829 (1997).

Frontiers of Chemistry: Biotechnology Chemical Abstract Service ACS, Columbus, OH pp. 665–670 (1980).

Fukuda, et al., "The Site of Initiation of Rod Assembly on the RNA of a Tomato and a Cowpea Strain of Tobacco Mosaic Virus," *Virology* 101:493–502 (1980).

Gardiner, et al., "Genetic analysis of tomato golden mosaic virus: the coat protein is not required for systemic spread of symptom development," *EMBO J.* 7(4):899–904 (1988).

Gardner, et al., "Potato spindle tuber viroid infections mediated by the Ti plasmid of *Agrobacterium tumefaciens*," *Plant. Mol. Biol.* 6:221–228 (1986).

Garoff, J., et al., "Recent advances in gene expression using alphavirus vectors," *Curr. Opin. Biotechnol.* 9(5):464–469 (1988).

Girard, et al., "Capsid Proteins of Simian Virus 40," *Biochem. Biophy. Res. Comm.* 40(1):97–102 (1970).

Giver, et al., ibid 2:335–338 (1998).

Giver, et al., *Proc. Natl. Acad. Sci. USA* 95:12809–12813 (1998).

Glazebrook, et al., "Use of Arabidopsis for Genetic Dissection of Plant Defense Responses," *Annu. Rev. Gen.* 31:547–569 (1997).

Gluzman, et al., *Communications in Molecular Biology: Viral Vectors*, Cold Spring Harbor Laboratory, pp. 172–189 (1988).

Goelet, et al., "Nucleotide sequence of tobacco mosaic virus RNA," *Proc. Natl. Acad. Sci. USA* 79:5818–5822 (1982).

Gorschen, E. et al., "Expression of the ribosome–inactivating protein JIP60 from barely in transgenic tobacco leads to an abnormal phenotype and alterations on the level transcription," *Planta* 202(4):470–478 (1997).

Graham, et al., "Wound–induced Proteinase Inhibitors from Tomato Leaves," *J. Biol. Chem.* 260(11):6555–6560 (1985).

Gramm, et al., *Proc. Natl. Acad. Sci. USA* 89:3576–3580 (1992).

Greene, A. and Allison, R., "Deletions in the 3' Untranslated Region of Cowpea Chlorotic Mottle Virus Transgene Reduce Recovery of Recombinant Viruses in Transgenic Plants," *Virology* 225(1):231–234 (1996).

Greene, A. and Allison, R., "Recombination Between Viral RNA and Transgenic Plant Transcripts," *Science* 263(5152):1423–1425 (1994).

Grierson, et al., "Does co–suppression of sense genes in transgenic plants involve antisense RNA?" *Trends Biotechnol.* 9:122–123 (1993).

Grimsley, et al., "Ágroinfection, an alternative route for viral infection of plants by using the Ti plasmid," *Proc. Natl. Acad. Sci. USA* 83:3282–3286 (1986).

Grimsley, et al., "Agrobacterium–mediated delivery of infectious maize streak virus into maize plants," *Nature* 325:177–179 (1987).

Grimwade, D., et al., "RT–PCR in Diagnosis and Disease Monitoring of Acute Promyelocytic Leukemia (APL)," *Methods Mol. Biol.*, 89:333–358 (1998).

Hahn, et al., "Sequence analysis of three Sindbis virus mutants temperature–sensitive in the capsid protein autoprotease," *Proc. Natl. Acad. Sci. USA* 82:4648–4652 (1985).

Hahn, et al., "Western equine encephalitis virus is a recombinant virus," *Proc. Natl. Acad. Sci. USA* 85:5997–6001 (1988).

Haizel, et al., "Characterization of proteins that interact with the GTP–bound form of the regulatory GTPase Ran in Arabidopsis," *The Plant J.*, 11:93–103 (1997).

Hayes, et al., "Agroinfection of *Triticum aestivum* with Cloned DNA of Wheat Dwarf Virus," *J. Gen. Virol.* 69:891–896 (1988).

Henry, et al., High–Leven Expression of the Ribosomal Protein L19 in Human Breast Tumors That Overexpress erb B–2[1] *Cancer Res.*, 53:1403–1408 (1993).

Horten, et al., "Engineering hybrid genes without the use of restriction enzymes: gene splicing by overlap extension," *Gene* 77:61–68 (1989).

Isaksson and Landegren, *Curr. Opinion Biotechnology* 10:11–15 (1999).

Ishikawa, M., et al., "In Vivo DNA Expression of Functional Brome Mosaic Virus RNA Replicons in *Saccharomyces cerevisiae*," *J. Virol.* 71(10):7781–7790 (1997).

Izant, et al., "Inhibition of Thymidine Kinase Gene Expression by Anti–Sense RNA: A Molecular Approach to Genetic Analysis," *Cell* 36(4):1007–1015 (1984).

Jacobson, G. and Roenbusch, J., "TP binding to a protease–resistant core of actin," *Proc. Natl. Acad. Sci. USA* 73(8):2742–2746 (1976).

Janda, M., et al., "RNA–Dependent Replication, Transcription, and Persistence of Brome Mosaic Virus RNA Replicons in *S. cerevisiae*," *Cell* 72(6):961–970 (1993).

Kaido, M., et al., "Inhibition of brome mosaic virus (BMV) amplification in protoplasts from transgenic tobacco plants expressing replicable BMV RNAs," *J. Gen. Virol.* 76(pt 11):2827–2833 (1995).

Karas, et al., "Laser Desorption Ionization of Proteins with Molecular Masses Exceeding 10 000 Daltons," *Anal. Chem.*, 60:2299–2301 (1988).

Kermode, "Mechanisms of Intracellular Protein Transport and Targeting in Plant Cells," *Critical Reviews in Plant Sciences* 15(4):285–423 (1996).

Kitamura, et al., "Primary structure, gene organization and polypeptide expression of poliovirus RNA," *Nature* 291:547–553 (1981).

Kovalic, et al., *Nucleic Acids Res.* 19:4560 (1991).

Kozak, "Compilation and analysis of sequences upstream from the translational start site in eukaryotic mRNAs," *Nucleic Acids Res.* 12:857 (1984).

Kozak, "How Do Eucaryotic Ribosomes Select Initiation Regions in Messenger RNA," *Cell* 15:1109–1123 (1978).

Kuchner, et al., *Trends Biotechnol.* 15:523–530 (1997).

Kumagai, et al., "Conversion of Starch to Ethanol in a Recombinant *Saccharomyces cerevisiae* Strain Expressing Rice –Amylase from a Novel *Pichia pastoris* Alcohol Oxidase Promoter," *Bio. Technology* 11:606–610 (1993).

Kumagai, et al., Cytoplasmic inhibition of carotenoid biosynthesis with virus–derived RNA, *Proc. Natl. Acad. Sci. USA* 92:1679–1683 (1995).

Kurisu, et al., "Biochemical Characterization of Cucumber Green Mottle Mosaic Virus Ribonucleic Acid," *Virology* 70:214–216 (1976).

Landegren, *Current Opinion Biotechnology* 7:95–97 (1996).

Lazar, G., et al., "Identification of a plant serine–arginine–rich protein similar to the mammalian splicing factor SF2/ASF," *Proc. Natl. Acad. Sci. USA* 92:7672–7676 (1995).

Lazarowitz, S., "Infectivity and complete nucleotide sequence of the genome of a Sough African isolate of maize streak virus," *Nucl. Acids Res.* 16(1):229–249 (1988).

Lebeurier, et al., "Inside–out model for self–assembly of tobacco mosaic virus," *Proc. Natl. Acad. Sci. USA* 74:149–153 (1977).

Levis, et al., "Engineered defective interfering RNAs of Sindbis virus express bacterial chloramphenicol acetyltransferase in avian cells," *Proc. Natl. Acad. Sci. USA* 84:4811–4815 (1987).

Lightner, et al., "Isolation of signaling mutants of tomato (*Lycopersicon esculentum*)," *J. Mol. Gen. Genet.* 241:595–601 (1993).

Lijsebettens, et al., *EMBO j.*, 13:3378–3388 (1994).

Lin, et al., *Proc. Natl. Acad. Sci. USA* 96:6535–6540 (1999).

Lindquist, et al., Sindbis Virus Mutant ts20 of Complementation Group E Contains a Lesion i Glycoprotein E2, *Virology* 151:10–20 (1986).

Liu, X., et al., "Receptor–mediated uptake of an extracellular Bcl–x(L) fusion protein inhibits apoptosis," *Proc. Natl. Acad. Sci. USA*, 96(17):9563–9567 (1999).

Lopato, S., et al. PNAS 92:7672–7676 (1995).

Lopato, S., et al., "Characterization of a Novel Arginine/Serine–Rich Splicing Factor in Arabidopsis," *The Plant Cell* 8:2255–2264 (1996).

Lopez, A., "Alternative Splicing of Pre–mRNA: Developmental Consequences and Mechanisms of Regulation," *Annu. Rev. Genetics* 32:279–305 (1998).

Maniatis, *Molecular Cloning*, 1st Ed.

Matthews, *Plant Virology*, 3rd Ed. Academic Press, San Diego (1991).

McCormick, et al., *Proc. Natl. Acad. Sci. USA* 96:703–708 (1999).

Medappa, et al., "On the Structure of Rhinovirus 1AP[1]," *Virology* 44:259–270 (1971).

Meshi, et al., "Nucleotide Sequence of the Coat Protein Cistron and the 3' Noncoding Region of Cucumber Green Mottle Mosaic Virus (Watermelon Strain) RNA," *Virology* 127:54–64 (1983).

*Methods in Enzymol* vols. 68, 100, 101, 118, and 152–155) (1979, 1983, 1986 and 1987).

*Methods Mol. Biol.* 89:333–358 (1998).

Miller, J., *Experiments in Molecular Genetics*, Cold Spring Harbor Laboratory, New York (1972).

Miller, W. and Hall, T., "RNA–Dependent RNA Polymerase Isolated from Cowpea Chlorotic Mottle Virus–Infected Cowpeas Is Specific for Bromoviral RNA," *Virology* 132:53–60 (1984).

Minshull, et al., "Protein evolution by molecular breeding," *Curr. Opin. Chem. Biol.* 3:284–290 (1999).

Misawa, et al., "Expression of an Erwinia phytoene desaturase gene not only confers multiple resistance to herbicides interfering with carotenoid biosynthesis but also alters xanthophyll metabolism in transgenic plants," *Plant J.* 6(4):481–489 (1994).

Mitsui, T. and Akazawa, T., "Preferential Secretion of R–Type –Amylast Molecules in Ride Seed Scutellum at High Temperatures," *Plant Physiol.* 82:880–884 (1986).

Monroe, S. and Schlesinger, S., "Common and Distinct Regions of Defective–Interfering RNAs of Sindbis Virus," *J. Virology* 49(3):865–872 (1984).

Moore, et al., "Directed evolution of a para–nitrobenzyl esterase for aqueous–organic solvents," Natl. *Biotechnol.* 14:458–467 (1996).

Morcey, et al., *Proc. Natl. Acad. Sci. USAi* 95:7866–7871 (1998).

Mori, et al., "mRNA amplification system by viral replicase in transgenic plants," *FEBS Lett.* 336(1):171–174 (1993).

Morozov, SYu, et al., "Complementation of a potatoe virus X mutant mediated by bombardment of plant tissues with cloned viral movement protein genes," *J Gen Virol (Pt 8)*:2077–2083 (1997).

Munishkin, et al., *Nature* 333(6172):473–5 (1988).

Nagano, H., et al., "Deletion of the C–terminal 33 Amino Acids of Cucumber Mosaic Virus Movement Protein Enables a Chimeric Brome Mosaic Virus to Move from Cell to Cell," *J. Virol.* 71(3):2270–2276 (1997).

Nagar, et al., "A Geminivirus Induces Expression of a Host DNA Synthesis Protein in Terminally Differentiated Plant Cells," *The Plant Cell*, 7:705–719 (1995).

Napoli, et al., "Introduction of a Chimeric Chalcone Synthase Gene into Petunia Results in Reversible Co–Suppression of Homologous Genes in trans," *The Plant Cell* 2:279–289 (1990).

*Natl. Acad. Sci. USA* 74:149 (1977).

Nozu, et al., "Chemical and Immunological Characterization of Cucumber Green Mottle Mosaic Virus (Watermelon Strain Protein)," *Virology* 45:577–585 (1971).

O'Neal, et al., "Isolation of tobacco SSU genes: characterization of a transcriptionally active pseudogene," *Nucl. Acids Res.* 15(21):8661–8677 (1987).

O'Neill, et al., "The amylase gene in *Oryza sativa*: Characterization of cDNA clones and mRNA expression during seed germination," *Mol. Gen. Genet.* 221:235–244 (1990).

Ogawa, et al., "Trans Complementation of Virus–Encoded Replicase Components of Tobacco Mosaic," *Virology* 185:580–584 (1991).

Ooshika, I., et al., "Identification of the 30K Protein of TMV by Immunoprecipitation with Antibodies Directed against a Synthetic Peptide," *Virology* 132:71 (1984).

Padgett, et al., "Creating seamless junctions independent of restriction sites in PCR cloning," *Gene* 168:31–35 (1996).

Patanjali, et al., "Construction of a uniform–abundance (normalized) cDNA library," *Proc. Natl. Acad. Sci. USA* 88:1943–1947 (1991).

Patten, et al., "Applications of DNA shuffling to pharmaceuticals and vaccines," *Curr. Opin. Chem. Biol.* 8:724–733 (1997).

Perrault, J., "Origin and Replication of Defective Interfering Particles," *Current Topics in Microgiology and Immunology* 93:151–207 (1981).

Piechaczek, C., et al., "A vector based on the SV40 origin of replication and chromosomal S/MARs replicates episomally in CHO cells," *Nucleic Acids Res.* 27(2):426–428 (1999).

*Plant Virology Protocol: From Virus Isolation to Transgenic Resistance in Methods in Molecular Biology*, vol. 81, Foster and Taylor, Ed., Humana Press (1998).

Priano, C., et al., "Translational Activation in Coliphase Qγ: On a Polycistronic Messenger RNA, Repression of One Gene can Activate Translation of Another," *J. Mol. Biol.* 271(3):299–310 (1997).

Price, et al., *Proc. Natl. Acad. Sci. USA* 93:9465–9570 (1996).

Prives, et al., "Cell–Free Translation of Messenger RNA of Simian Virus 40: Synthesis of the Major Capsid Protein," *Proc. Natl. Acad. Sci. USA* 71(2):302–306 (1974).

Pushko, P., et al., "Replicon–Helper Systems from Attenuated Venezuelan Equine Encephalitis Virus: Expression of Heterologous Genes in Vitro and Immunization against Heterologous Pathogens in Vivo," *Virology* 239(2):389–401 (1997).

Rao, A. and Grantham, G., "Biological Significance of the Seven Amino–Terminal Basic Residues of Brome Mosaic Virus Coat Protein," *Virology* 211(1):42–52 (1995).

Rao, A. and Grantham, G., "Molecular Studies on Bromovirus Capsid Protein. II. Functional Analysis of the Amino–Terminal Arginine–Rich Motif and Its Role in Encapsidation, Movement, and Pathology," *Virology* 226(92):294–305 (1996).

Rao, A., "Molecular Studies on Bromovirus Capsid Protein III. Analysis of Cell–to–Cell Movement Competence of Coat Protein Defective Variants of Cowpea Chlorotic Mottle Virus," *Virology* 232(2):385–395 (1997).

Rachtchian, et al., "Uracil DNA Glycosylase–Mediated Cloning of Polymerase Chain Reaction—Amplified DNA: Application to Genomic and cDNA Cloning," *Anal. Biochem.* 206:91–97 (1992).

Rachtchian, "Novel Methods for cloning and engineering genes using the polymerase chain reaction," *Curr. Opin. Biotechnol.* 6(1):30–36 (1995).

Regad, et al., "cDNA cloning and expression of an Arabidopsis GTP–binding protein of the ARF family," *FEBS* 316(2):133–136 (1993).

*Rice Biotechnology Quarterly* 37:4 (1999).

Ryan, C., et al., "Systemin: A Polypeptide Signal for Plant Defensive Genes," *Ann. Rev. Cell Dev. Biol.* 14:1–17 (1998).

Sablowski, R.W.M., et al. ,"Expression of a flowers specific Myb protein in leaf cells using a viral vector causes ectopic activation of a target promoter," *Proc. Natl. Acad. Sci. USA* 92:6901–6905 (1995).

Saiki, et al., "Enzymatic Amplification of β–Globin Genomic Sequences and Restriction Site Analysis for Diagnosis of Sickle Cell Anemia," *Science* 230:1350–1354 (1985).

Sambrook, et al., *Molecular Cloning: A Laboratory Manual*, Second Edition, Cold Spring Harbor Laboratory Press, Plainview, NY (1982, 1989).

Sanger, et al., "DNA sequencing with chain–terminating inhibitors," *Proc. Natl. Acad. Sci. USA* 74(12):5463–5467 (1977).

Schena, et al., *TIBECH* 16:301–306 (1998).

Schmitz, I. & Rao, A., "Molecular Studies on Bromovirus Capsid Protein I. Characterization of Cell–to–Cell Movement–Defective TNA3 Variants of Brome Mosaic Virus" *Virology* 226(2)281–293 (1996).

Schneider, W., et al., "The Carboxyl–Terminal Two–Thirds of the Cowpea Chlorotic Mottle Bromovirus Capsid Protein Is Incapable of Virion Formation yet Supports Systemic Movement," *J. Virology* 71(6):4862–4865 (1977).

Schwechheimer, C., et al., "Plant Transcription Factor Studies," *Annu. Rev. Plant Physiol. Plant Mol. Biol.* 49:127–150 (1998).

*Science* 276:1268–1272 (1997).

Shao, et al., "Random–priming in vitro recombination: an effective tool for directed evolution," *Nucleic Acids Res* 26:681–683 (1998).

Shatkin, *Cell* 9:645 (1976).

Shivprasad, et al., "Heterologous Sequences Greatly Affect Foreign Gene Expression in Tobacco Mosaic Virus–Based Vectors," *Virology* 255:313–323 (1999).

Skern, et al., "Human rhinovirus 2: complete nucleotide sequence and proteolytic processing signals in the capsid protein region," *Nucleoc Acids Res.* 13(6):2111–2126 (1985).

Smith, et al., Transgenic Plant Virus Resistance Mediated by Untranslatable Sense RNAs: Expression, Regulation, and FAte of Nonessential RNAs, *Plant Cell* 6(10):1441–1453 (1994).

Soares, et al., "Construction and characterization of a normalized cDNA library," *Proc. Natl. Acad. Sci. USA* 91:9228–9232 (1994).

Solis, et al., "The Complete Nucleotide Sequence of the Genomic RNA of the tobamovirus tobacco mile green mosaic virus,".

Stemmer, "Rapid evolution of a protein in vitro by a DNA shuffling," Nature 370:389–391 (1994).

Stemmer, "DNA shuffling by random fragmentation and reassembly: In vitro recombination for molecular evolution," *Proc. Natl. Acad. Sci. USA* 91:10747–10751 (1994).

Stemmer, *Sexual PCR and Assembly PCR in the Encyclopedia of Molecular Biology*, VCH Publishers, New York, pp. 447–457 (1996).

Strauss, E. and Strauss, J., "Structure and Replication of the Alphavirus Genome," *The Togaviridae and Flaviviridael*, Plenum Press, New York, pp. 35–90 (1980).

Susek, et al., "Signal Transduction Mutants of Arabidopsis Uncouple Nuclear CAB and RBCS Gene Expression from Chloroplast Development," *Cell* 74:784–799 (1993).

Takamatsu, et al., "Expression of bacterial chloramphenicol acetyltransferase gene in tobacco plants mediated by TMV–RNA," *The EMBO J.* 6(2):307–311 (1987).

Takamatsu, et al., "Production of enkephalin in tobacco protoplasts using tobacco mosaic virus RNA vector," *FEBS Letters* 269(1):73–76 (1990).

Tooze, J., Ed., "Appendix A—The SV40 Nucleotide Sequence," *Molecular Biology of Tumor Viruses—DNA Tumor Viruses*, Cold Spring Harbor Laboratory, New York, pp. 799–829 (1980).

Toyoda, et al., "Complete Nucleotide Sequences of All Three Poliovirus Serotype Genomes," *J. Mol. Biol.* 174:561–585 (1984).

Turpen, et al., "Transfection of whole plants from wounds inoculated with *Agrobacterium tumefaciens* containing cDNA of tobacco mosiac virus," *J. Virol. Methods* 42:227–240 (1993).

van der Krol, A., et al., "Flavonoid Genes in Petunia: Addition of a Limited Number of Gene Copies May Lead to a Suppression of Gene Expression," *Plant Cell* 2(4):291–299 (1990).

Van Lijsebettens, M., et al., "An S18 ribosomal protein gene copy at the Arabidopsis PFL locus affects plant development by its specific expression in meristems," *EMBO J.* 13(14):3378–3388.

Velculescu, et al., *Cell* 88:243 (1997).

Verwoert, et al., "A *Zea mays* GTP–binding protein of the ARF family complements an *Escherichia coli* mutant with a temperature–sensitive malonyl–coenzyme A:acyl carrier protein transacylase," *Plant Molecular Biol.* 27:629–633 (1995).

Voinnet ,O. et al., "Systemic signalling in gene silencing" *Nature* 389:553 (1997).

Walkey, *Applied Plant Virology*, Chapman & Hall (1991).

Watanabe, et al., "Synthesis of TMV–Specific RNAs and Proteins at the Early Stage of Infection in Tobacco Protoplasts: Transient Expression of the 30K Protein and its mRNA," *Virology* 133:18–24 (1987).

Waterhouse, et al., "Virus resistance and gene silencing in plants can be induced by simultaneous expression of sense and antisense RNA," *Proc. Natl. Acad. Sci. USA* 95:13959–13964 (1998).

Waterhouse, et al., "Virus resistance and gene silencing in plants can be induced by simultaneous expression of sense and antisense RNA," *Proc. Natl. Acad. Sci. USA* 10:13959–64 (1998).

Weaver, S., et al., "Recombinatorial History and Molecular Evolution of Western Equine Encephalomyelitis Complex Alphaviruses," *J. Virol.* 71(1):613–623 (1997).

Wingate, et al., "Isolation and Characterization of a Novel, Developmentally Regulated Proteinase Inhibitor I Protein and cDNA from the Fruit of a Wild Species of Tomato," *J. Biol. Chem.* 264(30):17734–17738 (1989).

Wychowski, et al., "The Intranuclear Location of Simian Virus 40 Polypeptides VP2 and VP3 Depends on a Specific Amino Acid Sequence," *J. Virol.* 61(12):3862–3869 (1987).

Yang, et al., "Construction of recombinant DNA by exonuclease recession," *Nucleic Acids Res.* 21:1889–1893 (1993).

Yon, et al., *Nucleic Acids Res.* 17:4895 (1989).

You, et al., *Protein Eng.* 9:77–83 (1994).

Zhang, et al., "Gene Expression Profiles in Normal and Cancel Cells," *Science* 276:1268–1272 (1997).

Zhang, et al., "Directed evolution of a fucosidase from a galactosidase by DNA shuffling and screening," *Proc. Natl. Acad. Sci. USA* 94:4504–4509 (1997).

Zhao, et al., "Functional and nonfunctional mutations distinguished by random recombination of homologous genes," *Proc. Natl. Acad. Sci. USA* 94:797–8000 (1997).

Zhao, et al., "Molecular evolution by staggered extension process (StEP) in vitro recombination," *Nat. Biotechnol.* 16:258–261 (1998).

Zhao, et al., "Directed evolution converts subtilisin E into a functional equivalent of thermitase," *Protein Eng.* 12:47–53 (1999).

Zheng, et al., "PNZIP Is a Novel Mesophyll–Specific cDNA That Is Regulated by Phytochrome and a Circadian Rhythm and Encodes a Protein with a Leucine Zipper Motif," *Plant Physiol.* 116:27–35 (1998).

\* cited by examiner

Nucleotide sequence alignment of 740 AT #120 to AA042085

```
740 AT #120   TCCGAAACATTCTTCGTAGTGAAGCAAAATGGGGTTGAGTTTCGCCAAGCTGTTTAGCAG
              ||||||||||||||||||||||||||||||||||||||||||||||||||||||||||||
AA042085      TCCGAAACATTCTTCGTAGTGAAGCAAAATGGGGTTGAGTTTCGCCAAGCTGTTTAGCAG

740 AT #120   GCTTTTTGCCAAGAAGGAGATGCGAATTCTGATGGTTGGTCTTGATGCTGCTGGTAAGAC
              ||||||||||||||||||||||||||||||||||||||||||||||||||||||||||||
AA042085      GCTTTTTGCCAAGAAGGAGATGCGAATTCTGATGGTTGGTCTTGATGCTGCTGGTAAGAC

740 AT #120   CACAATCTTGTACAAGCTCAAGCTCGGAGAGATTGTCACCACCATCCCTACTATTGGTTT
              ||||||||||||||||||||||||||||||||||||||||||||||||||||||||||||
AA042085      CACAATCTTGTACAAGCTCAAGCTCGGAGAGATTGTCACCACCATCCCTACTATTGGTTT

740 AT #120   CAATGTGGAAACTGTGGAATACAAGAACATTAGTTTCACCGTGTGGGATGTCGGGGGTCA
              ||||||||||||||||||||||||||||||||||||||||||||||||||||||||||||
AA042085      CAATGTGGAAACTGTGGAATACAAGAACATTAGTTTCACCGTGTGGGATGTCGGGGGTCA

740 AT #120   GGACAAGATCCGTCCCTTGTGGAGACACTACTTCCAGAACACTCAAGGTCTAATCTTTGT
              ||||||||||||||||||||||||||||||||||||||||||||||||||||||||||||
AA042085      GGACAAGATCCGTCCCTTGTGGAGACACTACTTCCAGAACACTCAAGGTCTAATCTTTGT

740 AT #120   TGTTGATAGCAATGACAGAGACAGAGTTGTTGAGGCTCGAGATGAACTCCACAGGATGCT
              ||||||||||||||||||||||||||||||||||||||||||||||||||||||||||||
AA042085      TGTTGATAGCAATGACAGAGACAGAGTTGTTGAGGCTCGAGATGAACTCCACAGGATGCT

740 AT #120   GAATGAGGACGAGCTGCGTGATGCTGTGTTGCTTGTGTTT
              |  ||||| |||||||||||||||||||||||||||||||
AA042085      GNATGAGNACGAGCTGCGTGATGCTGTGTTGCTTGTGTTT
```

Figure 7

Nucleotide sequence alignment of 740 AT #120 to *Oryza sativa* D17760

```
740 AT 120   27 AAATGGGGTTGAGTTTCGCCAAGCTGTTTAGCAGGCTTTTTGCCAAGAAGGAGATGCGAA  86
                | ||||||   |   ||| | ||||||| ||| | || || |||||  ||||||  |
D17760      166 AGATGGGGCTCACGTTCACGAAGCTGTTCAGCCGCCTCTTCGCCAAGAAGGAGATGAGGA  225

740 AT 120   87 TTCTGATGGTTGGTCTTGATGCTGCTGGTAAGACCACAATCTTGTACAAGCTCAAGCTCG  146
                | || ||||| ||||| ||||| || |||| |||||||| || ||| ||||||||||||
D17760      226 TCCTCATGGTCGGTCTCGATGCGGCCGGTAAAACCACCATCCTCTACAAGCTCAAGCTCG  285

740AT 120   147 GAGAGATTGTCACCACCATCCCTACTATTGGTTTCAATGTGGAAACTGTGGAATACAAGA  206
                | |||||  |||||||||||| ||  |||||||| |||||| ||||| |||||||||||
D17760      286 GCGAGATCGTCACCACTATCCCCACCATCGGTTTTAATGTCGAAACTGTTGAGTACAAGA  345

740 AT 120  207 ACATTAGTTTCACCGTGTGGGATGTCGGGGGTCAGGACAAGATCCGTCCCTTGTGGAGAC  266
                |||||||  ||||||| |||||||| ||||||||||||||||||||  |   ||||| |
D17760      346 ACATTAGCTTCACCGTTTGGGATGTTGGTGGTCAGGACAAGATCAGGCCCCGTGGAGGC  405

740 AT 120  267 ACTACTTCCAGAACACTCAAGGTCTAATCTTTGTTGTTGATAGCAATGACAGAGACAGAG  326
                |||| |||||||||||  |||| || |  | ||||| ||| ||||||||||||||| |
D17760      406 ACTATTTCCAGAACACCCAGGGCCTCATTTTTGTTGTGGACAGCAATGACAGAGAGCGTG  465

740 AT 120  327 TTGTTGAGGCTCGAGATGAACTCCACAGGATGCTGAATGAGGACGAGCTGCGTGATGCTG  386
                |||||||||   |  ||||| ||||| | |||||||||||||||||| ||| |||||||
D17760      466 TTGTTGAGGCCAGGGATGAGCTCCACCGTATGCTGAATGAGGATGAGCTACGTGATGCTG  525

740 AT 120  387 TGTTGCTTGTGTTTGCCAACAAGCAAGATCTTCCAAATGCTATGAACGCTGCTGAAATCA  446
                || |||| |||||||| ||||| |||||||||||| ||||||||||||||||| || ||
D17760      526 TGCTGCTGGTGTTTGCAAACAAACAAGATCTTCCTAATGCCATGAACGCTGCTGAGATCA  585

740 AT 120  447 CAGATAAGCTTGGCCTTCACTCCCTCCGTCAGCGTCATTGGTATATCCAGAGCACATGTG  506
                | || ||||||||| || |||||| | || || || ||||| |||||||||||||||||
D17760      586 CCGACAAGCTTGGTCTGCACTCCTTGCGCCAGCGGCACTGGTACATCCAGAGCACATGTG  645

740 AT 120  507 CCACTTCAGGTGAAGGGCTTTATGAAGGTCTGGACTGGCTCTCCAACAACATCGCTGGCA  566
                | || || ||||  |  ||||| | |||| || || ||||||||||||||| | ||
D17760      646 CTACCTCTGGTGAGGGGTTGTATGAGGGGCTTGACTGGCTTTCCAACAACATTGCCAACA  705

740 AT 120  567 AGGCATGATG  576
                ||||  ||| |
D17760      706 AGGCTTGAAG  715
```

Figure 8

Nucleotide sequence alignment of 740 AT #120 to KS+ Nb ARF #3

```
740 AT #120   TGGTCTTGATGCTGCTGGTAAGACCACAATCTTGTACAAGCTCAAGCTCGGAGAGATTGT
              |||||||||||| |||||||| ||||| || ||||||||||||||||| ||||||||  |
Nb ARF #3     CGGTCTTGATGCAGCTGGTAAAACCACCATATTGTACAAGCTCAAGCTGGGAGAGATAGT

740 AT #120   CACCACCATCCCTACTATTGGTTTCAATGTGGAAACTGTGGAATACAAGAACATTAGTTT
              |||| || ||||| ||||| |||||||||||| ||||| ||||||||||||||| | ||
Nb ARF #3     TACCACTATTCCTACCATTGGATTCAATGTGGAGACTGTTGAATACAAGAACATAAGCTT

740 AT #120   CACCGTGTGGGATGTCGGGGGTCAGGACAAGATCCGTCCCTTGTGGAGACACTACTTCCA
              ||| || |||||||| || ||||||||||||||||| || |||||||||| ||||||||
Nb ARF #3     CACGGTCTGGGATGTTGGTGGTCAGGACAAGATCCGACCATTGTGGAGGCATTACTTCCA

740 AT #120   GAACACTCAAGGTCTAATCTTTGTTGTTGATAGCAATGACAGAGACAGAGTTGTTGAGGC
              |||| ||||||| || ||||||| || |||||| |||| ||| | |  | |||||||||
Nb ARF #3     AAACACACAAGGACTTATCTTTGTGGTCGATAGTAATGATCGTGATCGTGTTGTTGAGGC

740 AT #120   TCGAGATGAACTCCACAGGATGCTGAATGAGGACGAGCTGCGTGATGCTGTGTTGCTTGT
              | |||||| ||||| || ||||| |||||||| |||| |||||  | ||||||||||| 
Nb ARF #3     TAGAGATGAGCTGCACCGGATGTTGAATGAGGATGAACTGAGGGATGCTGTGCTGCTTGT

740 AT #120   GTTTGCCAACAAGCAAGATCTTCCAAATGCTATGAACGCTGCTGAAATCACAGATAAGCT
              |||||| |||||||||||||||||||||||||||||| ||||||| || || ||||||
Nb ARF #3     GTTTGCTAACAAGCAAGATCTTCCAAATGCTATGAATGCTGCTGAGATTACTGACAAGCT

740 AT #120   TGGCCTTCACTCCCTCCGTCAGCGTCATTGG
              ||| |||||  | ||||||||| |||| |||
Nb ARF #3     TGGTCTTCATTCTCTCCGTCAACGTCACTGG
```

Figure 10

```
CTTAAAAGCAATATGACAGTAGAGAAGATCTCTCACAAAAGACCCAAAATCGAGTCGTGC
AAAATTGTACGAACAACAAAATTTAAAATTCAGTCCTTATCAAAGATCCAATCCAGCTGC
AACTAGCAACATTGGCTTAACGCTTCTTAGACACACCAACAGTCTTTCCTCTGCGACCAG
TTGTCTTGGTGTGTTGTCCACGAACACGGAGACCCCAGTAATGTCTCAGACCACGATGGT
TTCTGATTTTCTTGAGACGCTCAAGATCATCCCTGAGCTTCATGTCAAGGGCATTGGAGA
CAACTTGAGAGTACTTCCCATCCTTGTAATCTTTCTGTCTGTTCAAAAACCAGTCTGGAA
TCTTGAACTGTCTTGGGTTTGCAACAATAGTCATGAGGTTGTCAATCTCAGCTGCAGATA
ACTCACCAGCCCTCTTGTTCATGTCGACATCGGCTTTCTTGCAGACAATGTTGGCCAATC
TCCTTCCAATACCTTTGATAGAGGTAAGGGCAAACATAATCTTTTGCTTACCATCAACGG
TAG
```

Figure 13

```
CTGACATAAGTTATGTTCTTTGCGAAAATAAAAGTTATTCCACAAACGCATTCGATAAAA
CATTCAAAACCTTCTTCAGAGTCTAATCCGTGAACTGATGATCGATATAGCTTCACACTA
TATATCCTCTTCACTTCTTAGACTTCTTCTTCGGTACAGCTGCAGTTGGAGCAGGTGTAG
CAGCAGGTGCTGGAGCAGCTACAGGCGCAACATCTCCACCGGGACCCTTAGCTAAACGCT
CCTCTCTCCTAGCATGCTTCCTTTCTCGGCTAGCCTTGTTCTTCGCCCTCTTAGCCTCAA
ACTGATCAAGACAGAGTCTTCTCCCTAGCCTTCTCAAGCCTTTGACTTGTGGATACTCTC
CATCAAGACACGCTTGTTCTTGAACACATTTACCCTTAACACGCATGTACATGGTCATGG
TACATGTGCTTGTCAATCTTCTTTCGTCTCTCTGGATTTCTTCAAACAGACGCCTAAGAA
ACACGCCTTCCTACGCATTCCACAGTACCTTTGGTTGGGAACCTAACTTACGGGTACCCC
TTCCTTTTAACCGATTCCAGAGTGGCGACCCTTTATCTTGGCAATCTTCATTTTGCGAGC
TTGGAACAAGAGTGAATCTTGGGTGGCTTCTGATGATGAAACCTCTTTAAACTTTCTGAG
GTTTTGGCGGAAATGGCTGAAACGGATTTGTGGGACCAACCAAATTGCCTTTCGGCTTAA
TACTGATGCGACCGTTTGAGTAAAAACCGCCTTCAGG
```

Figure 15

METHOD OF COMPILING A FUNCTIONAL GENE PROFILE IN A PLANT BY TRANSFECTING A NUCLEIC ACID SEQUENCE OF A DONOR PLANT INTO A DIFFERENT HOST PLANT IN AN ANTI-SENSE ORIENTATION

This application is a Continuation-In-Part application of U.S. patent application Ser. No. 09/232,170, filed on Jan. 15, 1999, which is a Continuation-In-Part application of U.S. patent application, Ser. No. 09/008,186, filed on Jan. 16, 1998. All the above applications are incorporated herein by reference.

FIELD OF THE INVENTION

The present invention relates generally to the field of molecular biology and plant genetics. Specifically, the present invention relates to a method for determining the presence of a trait in a plant and a method of changing the phenotype or biochemistry of a plant, by expressing transiently a nucleic acid sequence in an antisense orientation in a host plant. This invention is exemplified by a nucleic acid sequence comprising a GTP binding protein open reading frame having an antisense orientation.

BACKGROUND OF THE INVENTION

Great interest exists in launching genome projects in plants comparable to the human genome project. Valuable and basic agricultural plants, including by way of example but without limitation, corn, soybeans and rice are targets for such projects because the information obtained thereby may prove very beneficial for increasing world food production and improving the quality and value of agricultural products. The United States Congress is considering launching a corn genome project. By helping to unravel the genetics hidden in the corn genome, the project could aid in understanding and combating common diseases of grain crops. It could also provide a big boost for efforts to engineer plants to improve grain yields and resist drought, pests, salt, and other extreme environmental conditions. Such advances are critical for a world population expected to double by 2050. Currently, there are four species which provide 60% of all human food: wheat, rice, corn, and potatoes, and the strategies for increasing the productivity of these plants is dependent on rapid discovery of the presence of a trait in these plants, and the function of unknown gene sequences in these plants.

One strategy that has been proposed to assist in such efforts is to create a database of expressed sequence tags (ESTs) that can be used to identify expressed genes. Accumulation and analysis of expressed sequence tags (ESTs) have become an important component of genome research. EST data may be used to identify gene products and thereby accelerate gene cloning. Various sequence databases have been established in an effort to store and relate the tremendous amount of sequence information being generated by the ongoing sequencing efforts. Some have suggested sequencing 500,000 ESTs for corn and 100,000 ESTs each for rice, wheat, oats, barley, and sorghum. Efforts at sequencing the genomes of plant species will undoubtedly rely upon these computer databases to share the sequence data as it is generated. *Arabidopsis thaliana* may be an attractive target discovery of a trait and for gene function discovery because a very large set of ESTs have already been produced in this organism, and these sequences tag more than 50% of the expected Arabidopsis genes.

Potential use of the sequence information so generated is enormous if gene function can be determined. It may become possible to engineer commercial seeds for agricultural use to convey any number of desirable traits to food and fiber crops and thereby increase agricultural production and the world food supply. Research and development of commercial seeds has so far focused primarily on traditional plant breeding, however there has been increased interest in biotechnology as it relates to plant characteristics. Knowledge of the genomes involved and the function of genes contained therein for both monocotyledonous and dicotyledonous plants is essential to realize positive effects from such technology.

The impact of genomic research in seeds is potentially far reaching. For example, gene profiling in cotton can lead to an understanding of the types of genes being expressed primarily in fiber cells. The genes or promoters derived from these genes may be important in genetic engineering of cotton fiber for increased strength or for "built-in" fiber color. In plant breeding, gene profiling coupled to physiological trait analysis can lead to the identification of predictive markers that will be increasingly important in marker assisted breeding programs. Mining the DNA sequence of a particular crop for genes important for yield, quality, health, appearance, color, taste, etc., are applications of obvious importance for crop improvement.

Work has been conducted in the area of developing suitable vectors for expressing foreign DNA and RNA in plant hosts. Ahlquist, U.S. Pat. Nos. 4,885,248 and 5,173,410 describes preliminary work done in devising transfer vectors which might be useful in transferring foreign genetic material into a plant host for the purpose of expression therein. All patent references cited herein are hereby incorporated by reference. Additional aspects of hybrid RNA viruses and RNA transformation vectors are described by Ahlquist et al. in U.S. Pat. Nos. 5,466,788, 5,602,242, 5,627,060 and 5,500,360, all of which are incorporated herein by reference. Donson et al, U.S. Pat. Nos. 5,316,931, 5,589,367 and 5,866,785, incorporated herein by reference, demonstrate for the first time plant viral vectors suitable for the systemic expression of foreign genetic material in plants. Donson et al. describe plant viral vectors having heterologous subgenomic promoters for the systemic expression of foreign genes. Carrington et al., U.S. Pat. No. 5,491,076, describe particular potyvirus vectors also useful for expressing foreign genes in plants. The expression vectors described by Carrington et al. are characterized by utilizing the unique ability of viral polyprotein proteases to cleave heterologous proteins from viral polyproteins. These include Potyviruses such as Tobacco Etch Virus. Additional suitable vectors are described in U.S. Pat. No. No. 5,811,653 and U.S. patent application Ser. No. 08/324,003, both of which are incorporated herein by reference.

Construction of plant RNA viruses for the introduction and expression of non-viral foreign genes in plants has also been demonstrated by Brisson et al., *Methods in Enzymology* 118:659 (1986), Guzman et al., Communications in Molecular Biology: Viral Vectors, Cold Spring Harbor Laboratory, pp. 172–189 (1988), Dawson et al., *Virology* 172:285–292 (1989), Takamatsu et al., *EMBO J.* 6:307–311 (1987), French et al., *Science* 231:1294–1297 (1986), and Takamatsu et al., *FEBS Letters* 269:73–76 (1990). However, these viral vectors have not been shown capable of systemic spread in the plant and expression of the non-viral foreign genes in the majority of plant cells in the whole plant. Moreover, many of these viral vectors have not proven stable for the maintenance of non-viral foreign genes. However, the viral vectors described by Donson et al., in U.S. Pat. Nos. 5,316,931, 5,589,367, and 5,866,785, Turpen in U.S. Pat. No. 5,811,653, Carrington et al. in U.S. Pat. No. 5,491,076, and in co-pending U.S. patent application Ser. No. 08/324,003, have proven capable of infecting plant cells with foreign genetic material and systemically spreading in the plant and expressing the non-viral foreign genes contained therein in plant cells locally or systemically. All patents, patent applications, and references cited in the instant application are hereby incorporated by reference.

With the recent advent of technology for cloning, genes can be selectively turned off. One method is to create antisense RNA or DNA molecules that bind specifically with a targeted gene's RNA message, thereby interrupting the precise molecular mechanism that expresses a gene as a protein. The antisense technology which deactivates specific genes provides a different approach from a classical genetics approach. Classical genetics usually studies the random mutations of all genes in an organism and selects the mutations responsible for specific characteristics. Antisense approach starts with a cloned gene of interest and manipulates it to elicit information about its function.

Post-transcriptional gene silencing (PTGS) in transgenic plants is the manifestation of a mechanism that suppresses RNA accumulation in a sequence-specific manner. There are three models to account for the mechanism of PTGS: direct transcription of an antisense RNA from the transgene, an antisense RNA produced in response to over expression of the transgene, or an antisense RNA produced in response to the production of an aberrant sense RNA product of the transgene (Baulcombe, *Plant Mol. Biol.* 32:79–88 (1996)). The PTGS mechanism is typified by the highly specific degradation of both the transgene mRNA and the target RNA, which contains either the same or complementary nucleotide sequences (Waterhouse et al *Proc. Natl. Acad. Sci. USA* 10: 13959–64 (1998)). Antisense RNA has been used to down regulate gene expression in transgenic and transfected plants. The effectiveness of antisense on the inhibition of eukaryotic gene expression was first demonstrated by Izant et al. (*Cell* 36(4):1007–1015 (1984)). Since then, the down-regulation of different genes from transgenic plants has been reported. Kumagai et al (*Proc. Natl. Acad. Sci. USA* 92:1679 (1995)) report that gene expression in transfected *Nicotiana benthamiana* was cytoplasmic inhibited by viral delivery of a RNA of a known sequence derived from cDNA encoding tomato phytoene desaturase in a positive sense or an antisense orientation. The host plant, *Nicotiana benthamiana*, and the donor plant, tomato (*Lycopersicon esculentum*), belong to the same family. There is also evidence that inhibition of endogenous genes occurs in transgenic plants containing sense RNA (Van der Krol et al., *Plant Cell* 2(4):291–299 (1990), Napoli et al., *Plant Cell* 2:279–289 (1990) and Fray et al., *Plant Mol. Biol.* 22:589–602 (1993)).

The antisense technology can be used to develop a functional genomic screening of a plant of interest. The antisense technology is applied in this invention to provide a method of discovering the presence of a trait in a plant and to determine the function and sequence of a nucleic acid of a plant by expressing the nucleic acid sequence that has not been identified in a different host plant. GTP-binding proteins exemplify this invention. In eukaryotic cells, GTP-binding proteins function in a variety of cellular processes, including signal transduction, cytoskeletal organization, and protein transport. The heterotrimeric and monomeric GTP-binding proteins that may be involved in secretion and intracellular transport are divided into two structural classes: the rab and the ARF families. The ARFs are highly conserved and found in all eukaryotic cells including human, yeast, plants, and slime mold. The cDNAs encoding GTP binding proteins have been isolated from a variety of plants including rice, barley, corn, tobacco, and *A. thaliana*. For example, Verwoert et al. (*Plant Molecular Biol.* 27:629–633 (1995)) report the isolation of a *Zea mays* cDNA clone encoding a GTP-binding protein of the ARF family by direct genetic selection in an *E. coli* fabD mutant with a maize cDNA expression library. Regad et al. (*FEBS* 2:133–136 (1993)) isolated a cDNA clone encoding the ARF from a cDNA library of *Arabidopsis thaliana* cultured cells by randomly selecting and sequencing cDNA clones. Dallmann et al. (*Plant Molecular Biol.* 19:847–857 (1992)) isolated two cDNAs encoding small GTP-binding proteins from leaf cDNA libraries using a PCR approach. Dallmann et al. prepared leaf cDNAs and use them as templates in PCR amplifications with degenerated oligonucleotides corresponding to the highly conserved motifs, found in members of the ras superfamily, as primers. The present invention provides advantages over the above isolation methods in that it only sequences clones that have a function and does not randomly sequence clones. Haizel et al., *Plant J.*, 11:92–103 (1997)) isolated cDNA and genomic clones encoding Ran-like small GTP binding proteins from Arabidopsis cDNA and genomic libraries using a full-length tobacco Nt Ran1 cDNA as a probe.

The present invention provides a method for discovering the presence of a trait in a plant by expressing a nucleic acid sequence in an antisense orientation in a host plant. Once the presence of a trait is identified by phenotypic changes, the nucleic acid insert in the cDNA clone or in the vector is then sequenced. The present method provides a rapid method for determining the presence of a trait and identifying a nucleic acid sequence and its function in a plant by screening a transfected host plant for its change of function.

SUMMARY OF THE INVENTION

The present invention is directed to a method of making a functional gene profile in a host plant by transiently expressing a nucleic acid sequence library in a host plant, determining the phenotypic or biochemical changes in the host plant, identifying a trait associated with the change, identifying the donor gene associated with the trait, and identifying the homologous host gene, if any. The invention is also directed to a method of changing the phenotype or biochemistry of a plant, a method of determining a change in phenotype or biochemistry in a plant, and a method of determining the presence of a trait in a plant. The method comprising the steps of expressing transiently an unidentified RNA or DNA sequence of a donor plant in an antisense orientation in a host plant, identifying changes in the host plant, and correlating the expression with the phenotypic changes. Alternatively, the method comprises the steps of expressing transiently a nucleic acid sequence of a donor plant in an antisense orientation in a host plant, identifying changes in the host plant, and correlating the expression with the phenotypic changes, wherein the donor plant and the host plant belong to different genus, family, order, class, subdivision, or division. The present invention is also directed to a method of determining the function of a nucleic acid sequence, including a gene, in a donor plant, by transfecting the nucleic acid sequence into a host plant in a manner so as to affect phenotypic changes in the host plant. In one embodiment, recombinant viral nucleic acids are prepared to include the nucleic acid insert of a donor. The recombinant viral nucleic acids infect a host plant and produce antisense RNAs in the cytoplasm which result in reduced expression of endogenous cellular genes in the host plant. Once the presence of a trait is identified by phenotypic changes, the function of the nucleic acid is determined. The nucleic acid insert in a cDNA clone or in a vector is then sequenced. The nucleic acid sequence is determined by a standard sequence analysis. This invention is exemplified by a nucleic acid sequence comprising a GTP binding protein open reading frame having an antisense orientation.

The present invention is also directed to a method of increasing yield of a grain crop. The method comprises expressing transiently a nucleic acid sequence of a donor plant in an antisense orientation in a grain crop, wherein said expressing results in stunted growth and increased seed production of the grain crop. A preferred method comprises the steps of cloning the nucleic acid sequence into a plant viral vector and infecting the grain crop with a recombinant viral nucleic acid comprising said nucleic acid sequence.

One aspect of the invention is a method of identifying and determining a nucleic acid sequence in a plant of interest, whose function is to silence endogenous genes in a host plant, by introducing the nucleic acid into the host plant by way of a viral nucleic acid such as a plant viral nucleic acid suitable to produce expression of the nucleic acid in the transfected host. This method utilizes the principle of post-transcription gene silencing of the endogenous host gene homolog, for example, antisense RNAs. Particularly, this silencing function is useful for silencing a multigene family frequently found in plants.

Another aspect of the invention is to discover genes having the same function in different plants. The method starts with a library of cDNAs, genomic DNAs, or a pool of RNAs of a first plant. Then, a recombinant viral nucleic acid comprising a nucleic acid insert derived from the library is prepared and is used to infect a different host plant. The infected host plant is inspected for phenotypic changes. The recombinant viral nucleic acid that results in phenotypic changes in the host plant is identified and the sequence of the nucleic acid insert is determined by a standard method. Such nucleic acid sequence in the first plant has substantial sequence homology as that in the host plant: the nucleic acid sequences are conserved between the two plants. This invention provides a rapid means for elucidating the function and sequence of nucleic acids of interest; such rapidly expanding information can be subsequently utilized in the field of genomics.

In one embodiment, a nucleic acid is introduced into a plant host wherein the plant host may be a monocotyledonous or dicotyledonous plant, plant tissue or plant cell. Preferably, the nucleic acid is introduced by way of a recombinant plant viral nucleic acid. Preferred recombinant plant viral nucleic acids useful in the present invention comprise a native plant viral subgenomic promoter, a plant viral coat protein coding sequence, and at least one non-native nucleic acid sequence. Some viral vectors used in accordance with the present invention may be encapsidated by the coat proteins encoded by the recombinant plant virus. Recombinant plant viral nucleic acids or recombinant plant viruses are used to infect a plant host. The recombinant plant viral nucleic acid is capable of replication in the host, localized or systemic spread in the host, and transcription or expression of the non-native nucleic acid in the host to produce a phenotypic or biochemical change. Any suitable vector constructs useful to produce localized or systemic expression of nucleic acids in host plants are within the scope of the present invention.

BRIEF DESCRIPTION OF THE FIGURES

FIG. 7 shows the nucleotide sequence comparison of *A. thaliana* 740 AT #120 and *A. thaliana* est AA042085

FIG. 8 shows the nucleotide sequence alignment of 740 AT #120 to rice D17760 (*Oryza sativa*) ADP-ribosylation factor.

FIG. 10 shows the nucleotide sequence comparison of *A. thaliana* 740 AT #120 and *N. benthamiana* KS+Nb ARF#3.

FIG. 13 shows the nucleotide sequence of 740 AT #377 (SEQ ID NO:31).

FIG. 15 shows the nucleotide sequence of 740 AT #2483 (SEQ ID NO:32).

DETAILED DESCRIPTION OF THE INVENTION

Figure 1:
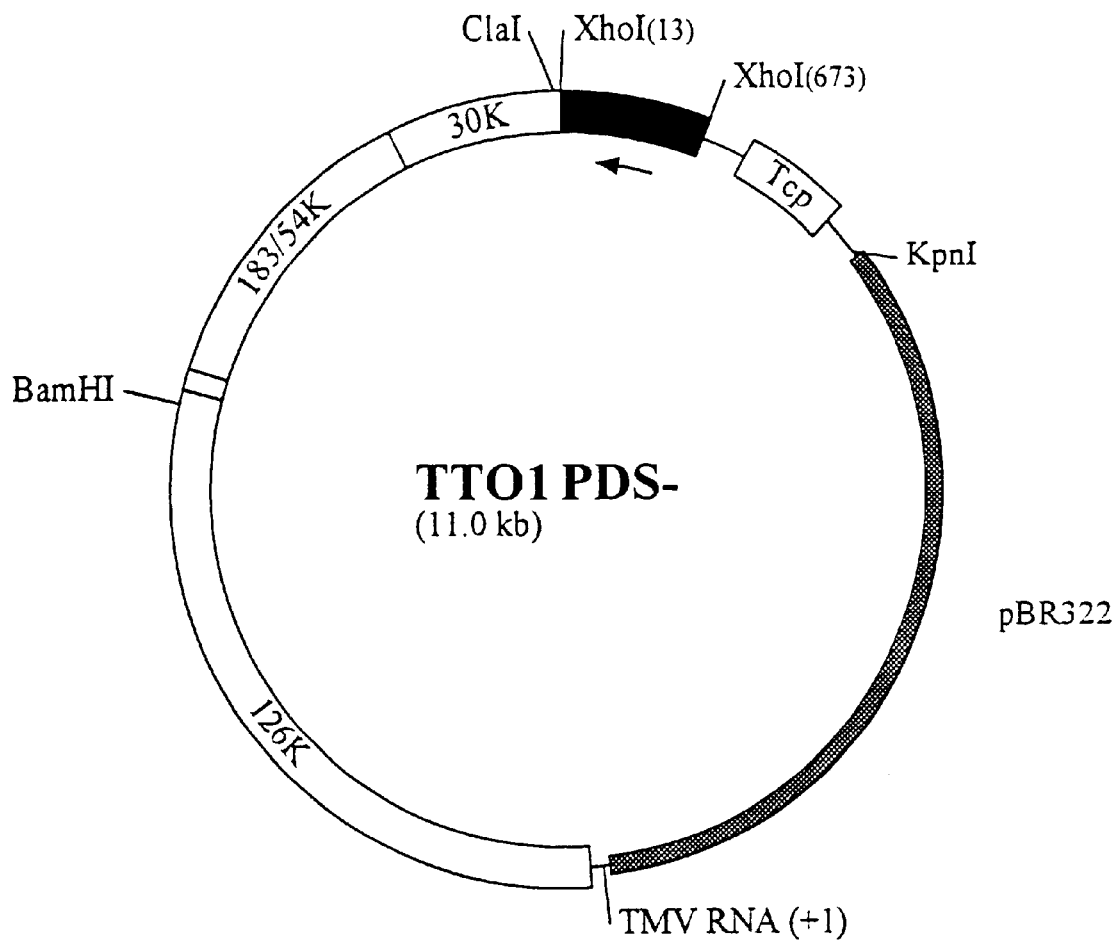
FIG. 1 depicts the vector TT01/PDS-.

The present invention is directed to a method of changing the phenotype or biochemistry of a plant, a method of determining a change in phenotype or biochemistry in a plant, a method of determining the presence of a trait in a plant, and a method of determining the function of a nucleic acid sequence. The methods comprise the steps of expressing transiently a nucleic acid sequence in an antisense orientation in a host organism such as a plant, a plant tissue or a plant cell, identifying changes in the host organism and correlating the expression and the changes. The presence of a trait is identified either in the infected host plant or in an uninfected host plant. The nucleic acid sequence, which is expressed in the host plant, does not need to be identified, isolated, or characterized prior to the expression. The donor plant and the host plant can belong to different genus, family, order, class, subdivision, or division. In one preferred embodiment, the method comprising the steps of (a) preparing a library of cDNAs, genomic DNAs, or a pool of RNAs of a donor plant, (b) constructing recombinant viral nucleic acids comprising a nucleic acid insert derived from said library, (c) infecting each said host plant with one of said recombinant viral nucleic acids, (d) growing said infected host plant, and (e) determining changes in said host plant.

The invention is directed to a method of compiling a plant antisense functional gene profile. The method comprises (a) preparing a vector library of DNA or RNA sequences from a donor plant, each sequence being in an antisense orientation; (b) infecting a plant host with a vector; (c) transiently expressing the donor plant DNA or RNA sequence in the growing plant host; (d) determining one or more phenotypic or biochemical changes in the plant host, if any; (e) identifying an associated trait where a phenotypic or biochemical change occurs; (f) identifying a donor plant gene associated with the trait; (g) identifying a plant host gene, if any, associated with the trait; and (h) repeating steps (b)–(g) until an antisense functional gene profile of the plant host and/or of the donor plant is compiled.

The invention is also directed to a method of compiling a plant functional gene profile. The method comprises (a) preparing a vector library of DNA or RNA sequences from a donor plant, each sequence being in either an antisense or a positive orientation; (b) infecting a plant host with a vector; (c) transiently expressing the donor plant DNA or RNA sequence in the growing plant host; (d) determining one or more phenotypic or biochemical changes in the plant host, if any; (e) identifying an associated trait where a phenotypic or biochemical change occurs; (f) identifying a donor plant gene associated with the trait; (g) identifying a plant host gene, if any, associated with the trait; and (h) repeating steps (b)–(g) until a functional gene profile of the plant host and/or of the donor plant is compiled. A detailed discussion of positive sense expression of nucleic acids is presented in a co-pending and co-owned U.S. patent application Ser. No. 09/359,305, the entire disclosure of which is incorporated herein by reference.

The present method has the advantages that the nucleic acid sequence does not need to be known, identified, isolated, or characterized prior to infecting a host plant with a recombinant viral nucleic acid comprising the nucleic acid sequence. Once changes in the host plant is observed, the nucleic acid sequence can be determined by further identifying the recombinant viral nucleic acid that results in changes in the host, and analyzing the sequence of the nucleic acid insert in the recombinant viral nucleic acid that results in changes in the host.

The present invention provides a method of infecting a host plant by a recombinant plant viral nucleic acid which contains one or more non-native nucleic acid sequences, or by a recombinant plant virus containing a recombinant plant viral nucleic acid. The non-native nucleic acids are subsequently transcribed or expressed in the infected host plant. The products of the non-native nucleic acid sequences result in changing phenotypic traits in the host plant, affecting biochemical pathways within the plant, or affecting endogenous gene expression within the plant.

In one embodiment, a nucleic acid is introduced into a plant host by way of a recombinant viral nucleic acid. Such recombinant viral nucleic acids are stable for the maintenance and transcription or expression of non-native nucleic acid sequences and are capable of systemically transcribing or expressing such non-native sequences in the plant host. Preferred recombinant plant viral nucleic acids useful in the present invention comprise a native plant viral subgenomic promoter, a plant viral coat protein coding sequence, and at least one non-native nucleic acid sequence.

In a second embodiment, plant viral nucleic acid sequences are characterized by the deletion of a native coat protein coding sequence. The plant viral nucleic acid sequence comprises a non-native plant viral coat protein coding sequence and a non-native promoter, preferably the subgenomic promoter of the non-native coat protein coding sequence. Such plant viral nucleic acid sequence is capable of expressing in a plant host, packaging the recombinant plant viral nucleic acid, and ensuring a systemic infection of the host by the recombinant plant viral nucleic acid. The recombinant plant viral nucleic acid may contain one or more additional native or non-native subgenomic promoters. Each non-native subgenomic promoter is capable of transcribing or expressing adjacent genes or nucleic acid sequences in the plant host and incapable of recombination with each other and with native subgenomic promoters. One or more non-native nucleic acids may be inserted adjacent to the native plant viral subgenomic promoter or the native and non-native plant viral subgenomic promoters if more than one nucleic acid sequence is included. Moreover, two or more heterologous non-native subgenomic promoters may be used. The non-native nucleic acid sequences may be transcribed or expressed in the host plant under the control of the subgenomic promoter to produce the products of the nucleic acids of interest.

In a third embodiment, plant recombinant viral nucleic acids comprise a native coat protein coding sequence instead of a non-native coat protein coding sequence, placed adjacent one of the non-native coat protein subgenomic promoters.

In a fourth embodiment, plant recombinant viral nucleic acids comprise a native coat protein gene adjacent its native subgenomic promoter, one or more non-native subgenomic promoters, and at least one non-native nucleic acid sequence. The native plant viral subgenomic promoter initiates transcription of the plant viral coat protein sequence. The non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that the sequences are transcribed or expressed in the host plant under control of the subgenomic promoters to produce a product of the non-native nucleic acid. Alternatively, the native coat protein coding sequence may be replaced by a non-native coat protein coding sequence.

The viral vectors used in accordance with the present invention may be encapsidated by the coat proteins encoded by the recombinant plant virus. The recombinant plant viral nucleic acid or recombinant plant virus is used to infect a host plant. The recombinant plant viral nucleic acid is capable of replication in the host, localized or systemic spread in the host, and transcription or expression of the non-native nucleic acid in the host to affect a phenotypic or biochemical change in the host.

In one embodiment, recombinant plant viruses are used which encode for the expression of a fusion between a plant viral coat protein and the amino acid product of the nucleic acid of interest. Such a recombinant plant virus provides for high level expression of a nucleic acid of interest. The location or locations where the viral coat protein is joined to the amino acid product of the nucleic acid of interest may be referred to as the fusion joint. A given product of such a construct may have one or more fusion joints. The fusion joint may be located at the carboxyl terminus of the viral coat protein or the fusion joint may be located at the amino terminus of the coat protein portion of the construct. In instances where the nucleic acid of interest is located internal with respect to the 5' and 3' residues of the nucleic acid sequence encoding for the viral coat protein, there are two fusion joints. That is, the nucleic acid of interest may be located 5', 3', upstream, downstream or within the coat protein. In some embodiments of such recombinant plant viruses, a "leaky" start or stop codon may occur at a fusion joint which sometimes does not result in translational termination. A more detailed description of some recombinant plant viruses according to this embodiment of the invention may be found in co-pending U.S. patent application Ser. No. 08/324,003 the disclosure of which is incorporated herein by reference.

The present invention is not intended to be limited to any particular viral constructs, but rather to include all operable constructs. Specifically, those skilled in the art may choose to transfer DNA or RNA of any size up to and including an entire genome in a plant into a host organism in order to determine the presence of a trait in the plant. Those skilled in the art will understand that the recited embodiments are representative only. All operable constructs useful to produce localized or systemic expression of nucleic acids in a plant are within the scope of the present invention.

The chimeric genes and vectors and recombinant plant viral nucleic acids used in this invention are constructed using techniques well known in the art. Suitable techniques have been described in Sambrook et al. (2nd ed.), Cold Spring Harbor Laboratory, Cold Spring Harbor (1982, 1989); *Methods in Enzymol.* (Vols. 68, 100, 101, 118, and 152–155) (1979, 1983, 1986 and 1987); and *DNA Cloning*, D. M. Clover, Ed., IRL Press, Oxford (1985). Medium compositions have been described by Miller, J., *Experiments in Molecular Genetics*, Cold Spring Harbor Laboratory, New York (1972), as well as the references previously identified, all of which are incorporated herein by reference. DNA manipulations and enzyme treatments are carried out in accordance with manufacturers' recommended procedures in making such constructs.

The first step in producing recombinant plant viral nucleic acids is to modify the nucleotide sequences of the plant viral nucleotide sequence by known conventional techniques such that one or more non-native subgenomic promoters are inserted into the plant viral nucleic acid without destroying the biological function of the plant viral nucleic acid. The subgenomic promoters are capable of transcribing or expressing adjacent nucleic acid sequences in a plant host infected by the recombination plant viral nucleic acid or recombinant plant virus. The native coat protein coding sequence may be deleted in some embodiments, placed under the control of a non-native subgenomic promoter in other embodiments, or retained in a further embodiment. If it is deleted or otherwise inactivated, a non-native coat protein gene is inserted under control of one of the non-native subgenomic promoters, or optionally under control of the native coat protein gene subgenomic promoter. The non-native coat protein is capable of encapsidating the recombinant plant viral nucleic acid to produce a recombinant plant virus. Thus, the recombinant plant viral nucleic acid contains a coat protein coding sequence, which may be native or a nonnative coat protein coding sequence, under control of one of the native or non-native subgenomic promoters. The coat protein is involved in the systemic infection of the plant host.

Viruses suitable for use according to the methods of the present invention include viruses from the tobamovirus group such as Tobacco Mosaic virus (TMV), Ribgrass Mosaic Virus (RGM), Cowpea Mosaic virus (CMV), Alfalfa Mosaic virus (AMV), Cucumber Green Mottle Mosaic virus watermelon strain (CGMMV-W) and Oat Mosaic virus (OMV) and viruses from the brome mosaic virus group such as Brome Mosaic virus (BMV), broad bean mottle virus and cowpea chlorotic mottle virus. Additional suitable viruses include Rice Necrosis virus (RNV), and geminiviruses such as Tomato Golden Mosaic virus (TGMV), Cassava Latent virus (CLV) and Maize Streak virus (MSV). Each of these groups of suitable viruses is characterized below. However, the invention should not be construed as limited to using these particular viruses, but rather the present invention is contemplated to include all plant viruses at a minimum.

TOBAMOVIRUS GROUP

The tobacco mosaic virus (TMV) is of particular interest to the instant invention because of its ability to express genes at high levels in plants. TMV is a member of the tobamovirus group. The TMV virion is a tubular filament, and comprises coat protein sub-units arranged in a single right-handed helix with the single-stranded RNA intercalated between the turns of the helix. TMV infects tobacco as well as other plants. TMV virions are 300 nm×18 nm tubes with a 4 nm-diameter hollow canal, and consist of 2140 units of a single structural protein helically wound around a single RNA molecule. The genome is a 6395 base plus-sense RNA. The 5'-end is capped and the 3'-end contains a series of pseudoknots and a tRNA-like structure that will specifically accept histidine. The genomic RNA functions as mRNA for the production of proteins involved in viral replication: a 126-kDa protein that initiates 68 nucleotides from the 5'-terminus, and a 183-kDa protein synthesized by read through of an amber termination codon approximately 10% of the time. Only the 183-kDa and 126-kDa viral proteins are required for the TMV replication in trans. (Ogawa et al., Virology 185:580–584 (1991)). Additional proteins are translated from subgenomic size mRNA produced during replication (Dawson, Adv. *Virus Res*., 38:307–342 (1990)). The 30-kDa protein is required for cell-to-cell movement; the 17.5-kDa capsid protein is the single viral structural protein. The function of the predicted 54-kDa protein is unknown.

TMV assembly apparently occurs in plant cell cytoplasm, although it has been suggested that some TMV assembly may occur in chloroplasts since transcripts of ctDNA have been detected in purified TMV virions. Initiation of TMV assembly occurs by interaction between ring-shaped aggregates ("discs") of coat protein (each disc consisting of two layers of 17 subunits) and a unique internal nucleation site in the RNA; a hairpin region about 900 nucleotides from the 3'-end in the common strain of TMV. Any RNA, including subgenomic RNAs containing this site, may be packaged into virions. The discs apparently assume a helical form on interaction with the RNA, and assembly (elongation) then proceeds in both directions (but much more rapidly in the 3'- to 5'-direction from the nucleation site).

Another member of the Tobamoviruses, the Cucumber Green Mottle Mosaic virus watermelon strain (CGMMV-W) is related to the cucumber virus. Nozu et al., *Virology* 45:577 (1971). The coat protein of CGMMV-W interacts with RNA of both TMV and CGMMV to assemble viral particles in vitro. Kurisu et al., *Virology* 70:214 (1976).

Several strains of the tobamovirus group are divided into two subgroups, on the basis of the location of the assembly of origin. Subgroup I, which includes the vulgare, OM, and tomato strain, has an origin of assembly about 800–1000 nucleotides from the 3'-end of the RNA genome, and outside the coat protein cistron. Lebeurier et al., *Proc. Natl. Acad. Sci*. USA 74:149 (1977); and Fukuda et al., *Virology* 101:493 (1980). Subgroup II, which includes CGMMV-W and corupea strain (Cc) has an origin of assembly about 300–500 nucleotides from the 3'-end of the RNA genome and within the coat-protein cistron. The coat protein cistron of CGMMV-W is located at nucleotides 176–661 from the 3'-end. The 3' noncoding region is 175 nucleotides long. The origin of assembly is positioned within the coat protein cistron. Meshi et al., *Virology* 127:54 (1983).

BROME MOSAIC VIRUS GROUP

Brome Mosaic virus (BMV) is a member of a group of tripartite, single-stranded, RNA-containing plant viruses commonly referred to as the bromoviruses. Each member of the bromoviruses infects a narrow range of plants. Mechanical transmission of bromoviruses occurs readily, and some members are transmitted by beetles. In addition to BV, other bromoviruses include broad bean mottle virus and cowpea chlorotic mottle virus.

Typically, a bromovirus virion is icosahedral, with a diameter of about 26 μm, containing a single species of coat protein. The bromovirus genome has three molecules of linear, positive-sense, single-stranded RNA, and the coat protein mRNA is also encapsidating. The RNAs each have a capped 5'-end, and a tRNA-like structure (which accepts tyrosine) at the 3'-end. Virus assembly occurs in the cytoplasm. The complete nucleotide sequence of BMV has been identified and characterized as described by Ahlquist et al., *J. Mol. Biol.* 153:23 (1981).

RICE NECROSIS VIRUS

Rice Necrosis virus is a member of the Potato Virus Y Group or Potyviruses. The Rice Necrosis virion is a flexuous filament comprising one type of coat protein (molecular weight about 32,000 to about 36,000) and one molecule of linear positive-sense single-stranded RNA. The Rice Necrosis virus is transmitted by *Polymyxa oraminis* (a eukaryotic intracellular parasite found in plants, algae and fungi).

GEMINIVIRUSES

Geminiviruses are a group of small, single-stranded DNA-containing plant viruses with virions of unique morphology. Each virion consists of a pair of isometric particles (incomplete icosahedral), composed of a single type of protein (with a molecular weight of about $2.7–3.4\times10^4$). Each geminivirus virion contains one molecule of circular, positive-sense, single-stranded DNA. In some geminiviruses (i.e., Cassava latent virus and bean golden mosaic virus) the genome appears to be bipartite, containing two single-stranded DNA molecules.

POTYVIRUSES

Potyviruses are a group of plant viruses which produce polyprotein. A particularly preferred potyvirus is tobacco etch virus (TEV). TEV is a well characterized potyvirus and contains a positive-strand RNA genome of 9.5 kilobases encoding for a single, large polyprotein that is processed by three virus-specific proteinases. The nuclear inclusion protein "a" proteinase is involved in the maturation of several replication-associated proteins and capsid protein. The helper component-proteinase (HC-Pro) and 35-kDa proteinase both catalyze cleavage only at their respective C-termini. The proteolytic domain in each of these proteins is located near the C-terminus. The 35-kDa proteinase and HC-Pro derive from the N-terminal region of the TEV polyprotein.

The nucleic acid of any suitable plant virus can be utilized to prepare a recombinant plant viral nucleic acid for use in the present invention, and the foregoing are only exemplary of such suitable plant viruses. The nucleotide sequence of the plant virus can be modified, using conventional techniques, by insertion of one or more subgenomic promoters into the plant viral nucleic acid. The subgenomic promoters are capable of functioning in a specific host plant. For example, if the host is a tobacco plant, TMV, TEV, or other viruses containing suitable subgenomic promoter may be utilized. The inserted subgenomic promoters should be compatible with the viral nucleic acid and capable of directing transcription or expression of adjacent nucleic acid sequences in tobacco.

The native or non-native coat protein gene is included in the recombinant plant viral nucleic acid. When non-native nucleic acid is utilized, it may be positioned adjacent its natural subgenomic promoter or adjacent one of the other available subgenomic promoters. The non-native coat protein, as is the case for the native coat protein, is capable of encapsidating the recombinant plant viral nucleic acid and providing for systemic spread of the recombinant plant viral nucleic acid in a host plant. The coat protein is selected to provide a systemic infection in the plant host of interest. For example, the TMV-O coat protein provides systemic infection in *N. benthamiana*, whereas TMV-U1 coat protein provides systemic infection in *N. tabacum.*

The recombinant plant viral nucleic acid is prepared by cloning a viral nucleic acid. If the viral nucleic acid is DNA, it can be cloned directly into a suitable vector using conventional techniques. One technique is to attach an origin of replication to the viral DNA which is compatible with the cell to be transfected. If the viral nucleic acid is RNA, a full-length DNA copy of the viral genome is first prepared by well-known procedures. For example, the viral RNA is transcribed into DNA using reverse transcriptase to produce subgenomic DNA pieces, and a double-stranded DNA made using DNA polymerases. The cDNA is then cloned into appropriate vectors and cloned into a cell to be transfected. Alternatively, the cDNA is ligated into the vector and is directly transcribed into infectious RNA in vitro, the infectious RNA is then inoculated onto the plant host. The cDNA pieces are mapped and combined in a proper sequence to produce a full-length DNA copy of the viral RNA genome, if necessary. DNA sequences for the subgenomic promoters, with or without a coat protein gene, are then inserted into the nucleic acid at non-essential sites, according to the particular embodiment of the invention utilized. Non-essential sites are those that do not affect the biological properties of the plant viral nucleic acids. Since the RNA genome is the infective agent, the cDNA is positioned adjacent a suitable promoter so that the RNA is produced in the production cell. The RNA can be capped by the addition of a nucleotide in a 5'—5' linkage using conventional techniques (Dawson et al., *Proc. Natl. Acad. Sci.* USA, 83:1832 (1986). One or more nucleotides may be added between the transcription start site of the promoter and the start of the cDNA of a viral nucleic acid to construct an infectious viral vector. In a preferred embodiment of the present invention, the inserted nucleotide sequence contains a G at the 5'-end. In one embodiment, the inserted nucleotide sequence is GNN, GTN, or their multiples, $(GNN)_x$ or $(GTN)_x$. The capped RNA can be packaged in vitro with added coat protein from TMV to make assembled virions. These assembled virions can then be used to inoculate plants or plant tissues.

Alternatively, an uncapped RNA may be employed in the embodiments of the present invention. Contrary to the practiced art in scientific literature and in an issued patent (Ahlquist et al., U.S. Pat. No. 5,466,788), uncapped transcripts for virus expression vectors are infective on both plants and in plant cells. Capping is not a prerequisite for establishing an infection of a virus expression vector in plants, although capping increases the efficiency of infection.

One feature of the recombinant plant viral nucleic acids useful in the present invention is that they further comprise one or more non-native nucleic acid sequences capable of being transcribed in a host plant. These nucleic acid sequences may be native nucleic acid sequences that occur in a host plant. Preferably, these nucleic acid sequences are non-native nucleic acid sequences that do not normally occur in a host plant. These nucleic acid sequences are derived from a donor plant, which is preferably genetically different from the host plant. The donor plant and the host plant may be genetically remote or unrelated: they may belong to different genus, family, order, class, subdivision, or division. Donor plants and host plants include plants of commercial interest, such as food crops, seed crops, oil crops, ornamental crops and forestry crops. For example, wheat, rice, corn, potatoes, barley, tobaccos, soybean canola, maize, oilseed rape, Arabidopsis, Nicotiana can be selected as a donor plant or a host plant. Host plants include those capable of being infected by an infectious RNA or a virus containing a recombinant viral nucleic acid. Preferred host plants include Nicotiana, preferably, *Nicotiana benthamiana*, or *Nicotiana cleavlandii*. Plant are grown from seed in a mixture of "Peat-Lite Mix™" (Speedling, Inc. Sun City, Fla.) and Nutricote™ controlled release fertilizer 14-14-14 (Chiss-Asahi Fertilizer Co., Tokyo, Japan). Plants are grown in a controlled environment provided 16 hours of light and 8 hours of darkness. Sylvania "Gro-Lux/Aquarium" wide spectrum 40 watt flourescent grow lights. (Osram Sylvania Products, Inc. Danvers, Mass.) are used. Temperatures are kept at around 80° F. during light hours and 70° F. during dark hours. Humidity is between 60 and 85%.

To prepare a DNA insert comprising a nucleic acid sequence of a donor plant, the first step is to construct a library of cDNAs, genomic DNAs, or a pool of RNAs of the plant of interest. Full-length cDNAs can be obtained from public or private repositories, for example, cDNA library of *Arabidopsis thaliana* can be obtained from the Arabidopsis Biological Resource Center. Alternatively, cDNA library can be prepared from a field sample by methods known to a person of ordinary skill, for example, isolating mRNAs and transcribing mRNAs into cDNAs by reverse transcriptase (see, e.g., Sambrook et al, *Molecular Cloning: A Laboratory Manual* (2nd ed.), Vols. 1–3, Cold Spring Harbor Laboratory, (1989), or *Current Protocols in Molecular Biology*, F. Ausubel et al., ed. Greene Publishing and Wiley-Interscience, New York (1987)). Genomic DNAs represented in BAC (bacterial artificial chromosome), YAC (yeast artificial chromosome), or TAC (transformation-competent artificial chromosome, Liu et al., *Proc. Natl. Acad. Sci. USA*, 96:6535–6540 (1999)) libraries can be obtained from public or private repositories, for example, the Arabidopsis Biological Resource Center. The BAC/YAC/TAC DNAs or cDNAs can be mechanically size-fractionated or digested by an enzyme to smaller fragments. The fragments are ligated to adapters with cohesive ends, and shotgun-cloned into recombinant viral nucleic acid vectors. Alternatively, the fragments can be blunt-end ligated into recombinant viral nucleic acid vectors. Recombinant plant viral nucleic acids containing a nucleic acid sequence derived from the CDNA library or genomic DNA library is then constructed using conventional techniques. The recombinant viral nucleic acid vectors produced comprise the nucleic acid insert derived from the donor plant. The nucleic acid sequence of the recombinant viral nucleic acid is transcribed as RNA in a host plant; the RNA is capable of regulating the expression of a phenotypic trait by an antisense mechanism. The nucleic acid sequence may also code for the expression of more than one phenotypic trait. Sequences from wheat, rice, corn, potato, barley, tobacco, soybean, canola, maize, oilseed rape, Arabidopsis, and other crop species may be used to assemble the DNA libraries. This method may thus be used to search for useful dominant gene phenotypes from DNA libraries through the gene expression.

A further alternative when creating the recombinant plant viral nucleic acid is to prepare more than one nucleic acid (i.e., to prepare the nucleic acids necessary for a multipartite viral vector construct). In this case, each nucleic acid would require its own origin of assembly. Each nucleic acid could be prepared to contain a subgenomic promoter and a non-native nucleic acid.

In some embodiments of the instant invention, methods to increase the representation of gene sequences in virus expression libraries may also be achieved by bypassing the genetic bottleneck of propagation in bacterial cells. For example, cell-free methods may be used to assemble sequence libraries or individual arrayed sequences into virus expression vectors and reconstruct an infectious virus, such that the final ligation product can be transcribed and the resulting RNA can be used for plant, plant tissue or plant cell inoculation/infection. A more detailed discussion is presented in a co-pending/co-owned U.S. patent application Ser. No. 09/359,303, incorporated herein by reference.

The host can be infected with a recombinant viral nucleic acid or a recombinant plant virus by conventional techniques. Suitable techniques include, but are not limited to, leaf abrasion, abrasion in solution, high velocity water spray, and other injury of a host as well as imbibing host seeds with water containing the recombinant viral RNA or recombinant plant virus. More specifically, suitable techniques include:

(a) Hand Inoculations. Hand inoculations are performed using a neutral pH, low molarity phosphate buffer, with the addition of celite or carborundum (usually about 1%). One to four drops of the preparation is put onto the upper surface of a leaf and gently rubbed.

(b) Mechanized Inoculations of Plant Beds. Plant bed inoculations are performed by spraying (gas-propelled) the vector solution into a tractor-driven mower while cutting the leaves. Alternatively, the plant bed is mowed and the vector solution sprayed immediately onto the cut leaves.

(c) Vacuum Infiltration. Inoculations may be accomplished by subjecting a host organism to a substantially vacuum pressure environment in order to facilitate infection.

(d) High Speed Robotics Inoculation. Especially applicable when the organism is a plant, individual organisms may be grown in mass array such as in microtiter plates. Machinery such as robotics may then be used to transfer the nucleic acid of interest.

(e) High Pressure Spray of Single Leaves. Single plant inoculations can also be performed by spraying the leaves with a narrow, directed spray (50 psi, 6–12 inches from the leaf) containing approximately 1% carborundum in the buffered vector solution.

(f) Ballistics (High Pressure Gun) Inoculation. Single plant inoculations can also be performed by particle bombardment. A ballistics particle delivery system (BioRad Laboratories, Hercules, (A) can be used to transfect plants such as *N. benthamiana* as described previously (Nagar et al, *Plant Cell*, 7:705–719 (1995)).

An alternative method for introducing a recombinant plant viral nucleic acid into a plant host is a technique known as agroinfection or Agrobacterium-mediated transformation (sometimes called Agro-infection) as described by Grimsley et al., *Nature* 325:177 (1987). This technique makes use of a common feature of Agrobacterium which colonizes plants by transferring a portion of their DNA (the T-DNA) into a host cell, where it becomes integrated into nuclear DNA. The T-DNA is defined by border sequences which are 25 base pairs long, and any DNA between these border sequences is transferred to the plant cells as well. The insertion of a recombinant plant viral nucleic acid between the T-DNA border sequences results in transfer of the recombinant plant viral nucleic acid to the plant cells, where the recombinant plant viral nucleic acid is replicated, and then spreads systemically through the plant. Agro-infection has been accomplished with potato spindle tuber viroid (PSTV) (Gardner et al., *Plant Mol. Biol.* 6:221 (1986); CaV (Grimsley et al., *Proc. Natl. Acad. Sci.* USA 83:3282 (1986)); MSV (Grimsley et al., *Nature* 325:177 (1987)), and Lazarowitz, S., *Nucl. Acids Res.* 16:229 (1988)) digitaria streak virus (Donson et al., *Virology* 162:248 (1988)), wheat dwarf virus (Hayes et al., *J. Gen. Virol.* 69:891 (1988)) and tomato golden mosaic virus (TGMV) (Elmer et al, *Plant Mol. Biol.* 10:225 (1988) and Gardiner et al., *EMBO J.* 7:899 (1988)). Therefore, agro-infection of a susceptible plant could be accomplished with a virion containing a recombinant plant viral nucleic acid based on the nucleotide sequence of any of the above viruses. Particle bombardment or electrosporation or any other methods known in the art may also be used.

Infection may also be attained by placing a selected nucleic acid sequence into an organism such as *E. coli*, or yeast, either integrated into the genome of such organism or not, and then applying the organism to the surface of the host organism. Such a mechanism may thereby produce secondary transfer of the selected nucleic acid sequence into a host organism. This is a particularly practical embodiment when the host organism is a plant. Likewise, infection may be attained by first packaging a selected nucleic acid sequence in a pseudovirus. Such a method is described in WO 4/10329, the teachings of which are incorporated herein by reference. Though the teachings of this reference may be specific for bacteria, those of skill in the art will readily appreciate that the same procedures could easily be adapted to other organisms.

After a host is infected with a recombinant viral nucleic acid comprising a nucleic acid insert derived from a cDNA library or a genomic library, one or more biochemical or phenotypic changes in a host plant is determined. The biochemical or phenotypic changes in the infected host plant is correlated to the biochemistry or phenotype of a host plant that is uninfected. Optionally, the biochemical or phenotypic changes in the infected host plant is further correlated to a host plant that is infected with a viral vector that contains a control nucleic acid of a known sequence in an antisense orientation; the control nucleic acid has similar size but is different in sequence from the nucleic acid insert derived from the library. For example, if the nucleic acid insert derived from the library is identified as encoding a GTP binding protein in an antisense orientation, a nucleic acid derived from a gene encoding green fluorescent protein can be used as a control nucleic acid. Green fluorescent protein is known not be have the same effect as the GTP binding protein when expressed in plants.

Those of skill in the art will readily understand that there are many methods to determine phenotypic or biochemical change in a plant and to determine the function of a nucleic acid, once the nucleic acid is localized or systemic expressed in a host plant. In a preferred embodiment, the phenotypic or biochemical trait may be determined by observing phenotypic changes in a host by methods including visual, morphological, macroscopic or microscopic analysis. For example, growth change such as stunting, hyperbranching, and necrosis; structure change such as vein banding, ring spot, etching; color change such as bleaching, chlorosis, or other color; and other changes such as marginal, mottled, patterening, punctate, and reticulate are easily detected. In another embodiment, the phenotypic or biochemical trait may be determined by complementation analysis, that is, by observing the endogenous gene or genes whose function is replaced or augmented by introducing the nucleic acid of interest. A discussion of such phenomenon is provided by Napoli et al., *The Plant Cell* 2:279–289 (1990). In a third embodiment, the phenotypic or biochemical trait may be determined by analyzing the biochemical alterations in the accumulation of substrates or products from enzymatic reactions according to any means known by those skilled in the art. In a fourth embodiment, the phenotypic or biochemical trait may be determined by observing any changes in biochemical pathways which may be modified in a host organism as a result of expression of the nucleic acid. In a fifth embodiment, the phenotypic or biochemical trait may be determined utilizing techniques known by those skilled in the art to observe inhibition of endogenous gene expression in the cytoplasm of cells as a result of expression of the nucleic acid. In a sixth embodiment, the phenotypic or biochemical trait may be determined utilizing techniques known by those skilled in the art to observe changes in the RNA or protein profile as a result of expression of the nucleic acid. In a seventh embodiment, the phenotypic or biochemical trait may be determined by selection of organisms such as plants capable of growing or maintaining viability in the presence of noxious or toxic substances, such as, for example herbicides and pharmaceutical ingredients.

Phenotypic traits in plant cells, which may be observed microscopically, macroscopically or by other methods, include improved tolerance to herbicides, improved tolerance to extremes of heat or cold, drought, salinity or osmotic stress; improved resistance to pests (insects, nematodes or arachnids) or diseases (fungal, bacterial or viral), production of enzymes or secondary metabolites; male or female sterility; dwarfness; early maturity; improved yield, vigor, heterosis, nutritional qualities, flavor or processing properties, and the like. Other examples include the production of important proteins or other products for commercial use, such as lipase, melanin, pigments, alkaloids, antibodies, hormones, pharmaceuticals, antibiotics and the like. Another useful phenotypic trait is the production of degradative or inhibitory enzymes, for example, enzymes preventing or inhibiting the root development in malting barley, or enzymes determining response or non-response to a systemically administered drug in a human. The phenotypic trait may also be a secondary metabolite whose production is desired in a bioreactor.

Biochemical changes can also be determined by analytical methods, for example, in a high-throughput, fully automated fashion using robotics. Suitable biochemical analysis may include MALDI-TOF, LC/MS, GC/MS, two-dimensional IEF/SDS-PAGE, ELISA or other methods of analyses. The clones in the plant viral vector library may then be functionally classified based on metabolic pathway affected or visual/selectable phenotype produced in the plant. This process enables the rapid determination of gene function for unknown nucleic acid sequences of a plant origin. Furthermore, this process can be used to rapidly confirm function of full-length DNA's of unknown gene function. Functional identification of unknown nucleic acid sequences in a plant library may then rapidly lead to identification of similar unknown sequences in expression libraries for other crop species based on sequence homology.

One useful means to determine the function of nucleic acids transfected into a host is to observe the effects of gene silencing. Traditionally, functional gene knockout has been achieved following inactivation due to insertion of transposable elements or random integration of T-DNA into the chromosome, followed by characterization of conditional, homozygous-recessive mutants obtained upon backcrossing. Some teachings in these regards are provided by WO 97/42210 which is herein incorporated by reference. As an alternative to traditional knockout analysis, an EST/DNA library from an organism, for example *Arabidopsis thaliana*, may be assembled into a plant viral transcription plasmid. The nucleic acid sequences in the transcription plasmid library may then be introduced into plant cells as part of a functional RNA virus which post-transcriptionally silences the homologous target gene. The EST/DNA sequences may be introduced into a plant viral vector in either the plus or minus sense orientation, and the orientation can be either directed or random based on the cloning strategy. A high-throughput, automated cloning scheme based on robotics may be used to assemble and characterize the library. In addition, double stranded RNA may also be an effective stimulator of gene silencing in transgenic plant. Gene silencing of plant genes may be induced by delivering an RNA capable of base pairing with itself to form double stranded regions. This approach could be used with any plant gene to assist in the identification of the function of a particular gene sequence.

The present invention provides a method to produce transfected plants containing viral-derived antisense RNA in the cytoplasm. Such method is much faster than the time required to obtain genetically engineered antisense transgenic plants. Systemic infection and expression of viral antisense RNA occurs as short as four days post inoculation, whereas it takes several months or longer to create a single transgenic plant. The invention provides a method to identify genes involved in the regulation of plant growth by inhibiting the expression of specific endogenous genes using viral vectors, which replicate solely in the cytoplasm. This invention provides a method to characterize specific genes and biochemical pathways in donor plants or in host plants using an RNA viral vector.

The invention is also directed to a method of determining a nucleic acid sequence in a donor plant, which has the same function as that in a genetically different host plant, by transfecting a nucleic acid sequence derived from a donor plant into a plant host. In one preferred embodiment, the method comprising the steps of (a) preparing a library of cDNAs, genomic DNAs, or a pool of RNAs of the donor plant, (b) constructing recombinant viral nucleic acids comprising a nucleic acid insert derived from the library, (c) infecting each host plant with the one of the recombinant viral nucleic acids, (d) growing the infected host plant, (e) determining one or more changes in the host plant, (f) identifying the recombinant viral nucleic acid that results in changes in the host, (g) determining the sequence of the nucleic acid insert in the recombinant viral nucleic acid that results in changes in the host, and (h) determining the sequence of an entire open reading frame of the donor from which the nucleic acid insert is derived.

The invention is further directed to a method of determining a nucleic acid sequence in a host plant, which has the same function as that in a genetically different donor plant, by transfecting a nucleic acid sequence derived from a donor plant into a host plant. In one preferred embodiment, the method comprising the steps of (a) preparing a library of cDNAs, genomic DNAs, or a pool of RNAs of the donor plant, (b) constructing recombinant viral nucleic acids comprising a nucleic acid insert derived from the library, (c) infecting each host plant with one of said recombinant viral nucleic acids, (d) growing the infected host plant, (e) determining one or more changes in the host plant, (f) identifying the recombinant viral nucleic acid that results in changes in the host, (g) determining the sequence of the nucleic acid insert in the recombinant viral nucleic acid that results in changes in the host, and (h) determining the sequence of an entire open reading frame of a gene in the host plant, the expression of which is affected by the insert. The sequence of the nucleic acid insert in the cDNA clone or in the viral vector can be determined by a standard method, for example, by dideoxy termination using double stranded templates (Sanger et al., *Proc., Natl. Acad. Sci.* USA 74:5463–5467 (1977)). Once the sequence of the nucleic acid insert is obtained, the sequence of also encapsidating. The RNAs each have a capped 5'-end, and a tRNA-like structure full-length cDNAs from the cDNA library with the nucleic acid insert labeled with radioactive, fluorescent, or enzyme molecules. The sequence of an entire open reading frame of a gene can also be determined by RT-PCR (*Methods Mol. Biol.*, 89:333–358 (1998)).

The present invention is also directed to a method of changing the phenotype or biochemistry of a plant by expressing transiently a nucleic acid sequence from a donor plant in an antisense orientation in a host plant, which inhibits an endogenous gene expression in the meristem of the host plant. The one or more phenotypic or biochemical changes in the host plant are detected by methods as describes previously. Transient expressing a nucleic acid sequence in a host plant can affect the gene expression in meristem. Meristems are of interest in plant development because plant growth is driven by the formation and activity of meristems throughout the entire life cycle. This invention is exemplified by a nucleic acid sequence encoding ribosomal protein S18. The activity of S18 promoter is restricted to meristems (Lijsebettesn et al., *EMBO J.* 13: 3378–3388). Transient expression of a nucleic acid sequence in a host plant can trigger a signal transmitting to meristems and affect the gene expression in meristem.

One problem with gene silencing in a plant host is that many plant genes exist in multigene families. Therefore, effective silencing of a gene function may be especially problematic. According to the present invention, however, nucleic acids may be inserted into the viral genome to effectively silence a particular gene function or to silence the function of a multigene family. It is presently believed that about 20% of plant genes exist in multigene families.

A detailed discussion of some aspects of the "gene silencing" effect is provided in the co-pending patent application, U.S. patent application Ser. No. 08/260,546 (WO95/34668 published Dec. 21, 1995) the disclosure of which is incorporated herein by reference. RNA can reduce the expression of a target gene through inhibitory RNA interactions with target mRNA that occur in the cytoplasm and/or the nucleus of a cell.

An EST/cDNA library from a plant such as *Arabidopsis thaliana* may be assembled into a plant viral transcription plasmid background. The cDNA sequences in the transcription plasmid library can then be introduced into plant cells as cytoplasmic RNA in order to post-transcriptionally silence the endogenous genes. The EST/cDNA sequences may be introduced into the plant viral transcription plasmid in either the plus or anti-sense orientation (or both), and the orientation can be either directed or random based on the cloning strategy. A high-throughput, automated cloning strategy using robotics can be used to assemble the library. The EST clones can be inserted behind a duplicated subgenomic promoter such that they are represented as subgenomic transcripts during viral replication in plant cells.

Alternatively, the EST/cDNA sequences can be inserted into the genomic RNA of a plant viral vector such that they are represented as genomic RNA during the viral replication in plant cells. The library of EST clones is then transcribed into infectious RNAs and inoculated onto a host plant susceptible to viral infection. The viral RNAs containing the EST/cDNA sequences contributed from the original library are now present in a sufficiently high concentration in the cytoplasm of host plant cells such that they cause post-transcriptional gene silencing of the endogenous gene in a host plant. Since the replication mechanism of the virus produces both sense and antisense RNA sequences, the orientation of the EST/cDNA insert is normally irrelevant in terms of producing the desired phenotype in the host plant.

It is known that silencing of endogenous genes can be achieved with homologous sequences from the same family. For example, Kumagai et al., (*Proc. Natl. Acad. Sci.* USA 92:1679 (1995)) report that the *Nicotiana benthamiana* gene for phytoene desaturase (PDS) was silenced by transfection with a viral RNA derived from a clone containing a partial tomato (*Lycopersicon esculentum*) cDNA encoding PDS being in an antisense orientation. This paper is incorporated here by reference. Kumagai et al. demonstrate that gene encoding PDS from one plant can be silenced by transfection a host plant with a nucleic acid of a known sequence, namely, a PDS gene, from a donor plant of the same family. The present invention provides a method of silencing a gene in a host plant by transfecting the host plant with a viral nucleic acid comprising a nucleic acid insert derived from a CDNA library, a genomic DNA library, or a pool of RNA. Different from Kumagai et al, the sequence of the nucleic acid insert in the present invention is not identified or isolated prior to the transfection. Another feature of the present invention is that it provides a method to silence a gene of a different family; the antisense transcript of one plant results in reducing expression of the endogenous gene or multigene family of a plant of a different genus, family, order, class, subdivision, division, or subkingdom. The invention is exemplified by GTP cellular processes, including signal transduction, cytoskeletal organization, and protein transport. Low molecular weight (20–25 K Daltons) of GTP-binding proteins include ras and its close relatives (for example, Ran), rho and its close close relatives, the rab invention, the inserted nucleotide sequence contains a G at the 5'-end. In one monomeric GTP-binding proteins that may be involved in secretion and intracellular transport are divided into two structural classes: the rab and the ARF families. The ARFs from many organisms have been isolated and characterized. The ARFs share structural features with both the ras and trimeric GTP-binding protein families. The present invention demonstrates that genes of one plant, such as Nicotiana, which encode GTP binding proteins, can be silenced by transfection with infectious RNA from a clone containing GTP binding protein open reading frame in an antisense orientation, derived from a plant of a different family, such as Arabidopsis.

The present invention also provides a method of isolating a conserved gene such as a gene encoding a GTP binding protein, from rice, barley, corn, soybean, maize, oilseed, and other plant of commercial interest, using another gene having homology with gene being isolated. Libraries containing full-length cDNAs from a donor plant such as rice, barley, corn, soybean and other important crops can be obtained from public and private sources or can be prepared from plant mRNAs. The cDNAs are inserted in viral vectors or in small subcloning vectors such as pBluescript (Strategene), pUC18, M13, or pBR322. Transformed bacteria are then plated and individual clones selected by a standard method. The bacteria transformants or DNAs are rearrayed at high density onto membrane filters or glass slides. Full-length cDNAs encoding GTP binding proteins can be identified by probing filters or slides with labeled nucleic acid inserts which result in changes in a host plant, or labeled probes prepared from DNAs encoding GTP binding proteins from Arabidopsis. Useful labels include radioactive, fluorescent, or chemiluminecent molecules, enzymes, etc.

Alternatively, genomic libraries containing sequences from rice, barley, corn, soybean and other important crops can be obtained from public and private sources, or be prepared from plant genomic DNAs. BAC clones containing entire plant genomes have been constructed and organized in a minimal overlapping order. Individual BACs are sheared to fragments and directly cloned into viral vectors. Clones that completely cover an entire BAC form a BAC viral vector sublibrary. Genomic clones can be identified by probing filters containing BACs with labeled nucleic acid inserts which result in changes in a host plant, or with labeled probes prepared from DNAs encoding GTP binding proteins from Arabidopsis. Useful labels include radioactive, fluorescent, or chemiluminecent molecules, enzymes, etc. BACs that hybridize to the probe are selected and their corresponding BAC viral vectors are used to produce infectious RNAs. Plants that are transfected with the BAC sublibrary are screened for change of function, for example, change of growth rate or change of color. Once the change of function is observed, the inserts from these clones or their corresponding plasmid DNAs are characterized by dideoxy sequencing. This provides a rapid method to obtain the genomic sequence for a plant protein, for example, a GTP binding protein. Using this method, once the DNA sequence in one plant such as *Arabidopsis thaliana* is identified, it can be used to identify conserved sequences of similar function that exist in other plant libraries.

Large amounts of DNA sequence information are being generated in the public domain and may be entered into a relational database. Links may be made between sequences from various species predicted to carry out similar biochemical or regulatory unctions. Links may also be generated between predicted enzymatic activities and visually displayed biochemical and regulatory pathways. Likewise, links may be generated between predicted enzymatic or regulatory activity and known small molecule inhibitors, activators, substrates or substrate analogs. Phenotypic data from expression libraries expressed in transfected hosts may be automatically linked within such a relational database. Genes with similar predicted roles of interest in other crop plants may be rapidly discovered.

A functional genomics screen is set up using a tobacco mosaic virus TMV-O coat protein capsid for infection of *Nicotiana benthamiana*, a plant related to the common tobacco plant. For *Arabidopsis thaliana* cDNA librariers are obtained from the Arabidopsis Biological Resource Center, Bluescript® phagemid vectors are recovered by Not 1 digestion. cDNA is transformed into a plasmid. The plasmid is transcribed into viral vector RNA. The inserts are in the antisense orientation as in Figure until all of the cDNA from each cDNA library is represented on viral vectors. Each viral vector is sprayed onto the leaf of a two-week old *N. benthamiana* plant host with sufficient force to cause tissue injury and localized viral infection. Each infected plant is grown side by side with an uninfected plant and a plant infected with a null insert vector as controls. All plants are grown in an artificial environment having 16 hours of light and 8 hours of dark. Lumens are approximately equal on each plant. At intervals of 2 days a visual and photographic observation of phenotype is made and recorded for each infected plant and each of its controls and a comparison is made. Data is entered into a Laboratory Information Management System database. At the end of the observation period stunted plants are grouped for analysis. The nucleic acid insert contained in the viral vector clone 740AT#120 is responsible for severe stunting of one of the plants. Clone 740AT #120 is sequenced. The homolog from the plant host is also sequenced. The 740AT #120 clone is found to have 80% hemology to plant host nucleic acid sequence. The amino acid sequence of hemology is 96%. The entire cDNA sequence of the insert is obtained by sequencing and found to code for a GTP binding protein. The host plant homolog is selected and sequenced. It also codes for a GTP binding protein. We conclude that this GTP binding protein coding sequence is highly conserved in nature. This information is useful in pharmaceutical development as well as in toxicology studies.

A complete classification scheme of gene functionality for a fully sequenced eukaryotic organism has been established for yeast. This classification scheme may be modified for plants and divided into the appropriate categories. Such organizational structure may be utilized to rapidly identify herbicide target loci which may confer dominant lethal phenotypes, and thereby is useful in helping to design rational herbicide programs.

The present invention is also directed to a method of increasing yield of a grain crop. In Rice *Biotechnology Quarterly* (37:4, (1999)), it is reported that a transgenic rice plant transformed with a rgpl gene, which encodes a small GTP binding protein from rice, was shorter than a control plant, but it produced more seeds than the control plant. To increase the yield of a grain crop, the present method comprises expressing transiently a nucleic acid sequence of a donor plant in an antisense orientation in the grain crop, wherein said expressing results in stunted growth and increased seed production of said grain crop. A preferred method comprises the steps of cloning the nucleic acid sequence into a plant viral vector and infecting the grain crop with a recombinant viral nucleic acid comprising said nucleic acid sequence. Preferred plant viral vector is derived from a Brome Mosaic virus, a Rice Necrosis virus, or a geminivirus. Preferred grain crops include rice, wheat, and barley. The nucleic acid expressed in the host plant, for example, comprises a GTP binding protein open reading frame having an antisense orientation. The present method provides a transiently expression of a gene to obtain a stunted plant. Because less energy is put into plant growth, more energy is available for production of seed, which results in increase yield of a grain crop. The present method has an advantage over other method using a trangenic plant, because it does not have an effect on the genome of a host plant.

In order to provide an even clearer and more consistent understanding of the specification and the claims, including the scope given herein to such terms, the following definitions are provided:

Adjacent: A position in a nucleotide sequence proximate to and 5' or 3' to a defined sequence. Generally, adjacent means within 2 or 3 nucleotides of the site of reference.

Anti-Sense Inhibition: A type of gene regulation based on cytoplasmic, nuclear or organelle inhibition of gene expression due to the presence in a cell of an RNA molecule complementary to at least a portion of the mRNA being translated. It is specifically contemplated that RNA molecules may be from either an RNA virus or mRNA from the host cells genome or from a DNA virus.

Cell Culture: A proliferating group of cells which may be in either an undifferentiated or differentiated state, growing contiguously or non-contiguously.

Chimeric Sequence or Gene: A nucleotide sequence derived from at least two heterologous parts. The sequence may comprise DNA or RNA.

Coding Sequence: A deoxyribonucleotide or ribonucleotide sequence which, when either transcribed and translated or simply translated, results in the formation of a cellular polypeptide or a ribonucleotide sequence which, when translated, results in the formation of a cellular polypeptide.

Compatible: The capability of operating with other components of a system. A vector or plant or animal viral nucleic acid which is compatible with a host is one which is capable of replicating in that host. A coat protein which is compatible with a viral nucleotide sequence is one capable of encapsidating that viral sequence.

Complementation Analysis: As used herein, this term refers to observing the changes produced in an organism when a nucleic acid sequence is introduced into that organism after a selected gene has been deleted or mutated so that it no longer functions fully in its normal role. A complementary gene to the deleted or mutated gene can restore the genetic phenotype of the selected gene.

Dual Heterologous Subgenomic Promoter Expression System (DHSPES): a plus stranded RNA vector having a dual heterologous subgenomic promoter expression system to increase, decrease, or change the expression of proteins, peptides or RNAs, preferably those described in U.S. Pat. Nos. 5,316,931, 5,811,653, 5,589,367, and 5,866,785, the disclosure of which is incorporated herein by reference.

Expressed sequence tags (ESTs): Relatively short single-pass DNA sequences obtained from one or more ends of cDNA clones and RNA derived therefrom. They may be present in either the 5' or the 3' orientation. ESTs have been shown useful for identifying particular genes.

Expression: The term as used herein is meant to incorporate one or more of transcription, reverse transcription and translation.

A functional Gene Profile: The collection of genes of an organism which code for a biochemical or phenotypic trait. The functional gene profile of an organism is found by screening nucleic acid sequences from a donor organism by over expression or suppression of a gene in a host organism. A functional gene profile requires a collection or library of nucleic acid sequences from a donor organism. A functional gene profile will depend on the ability of the collection or library of donor nucleic acids to cause over-expression or suppression in the host organism. Therefore, a functional gene profile will depend upon the quantity of donor genes capable of causing over-expression or suppression of host genes or of being expressed in the host organism in the absence of a homologous host gene.

Gene: A discrete nucleic acid sequence responsible for producing one or more cellular products and/or performing one or more intercellular or intracellular functions.

Gene silencing: A reduction in gene expression. A viral vector expressing gene sequences from a host may induce gene silencing of homologous gene sequences.

Homology: A high degree of nucleic acid similarity in all or some portions of a gene sequence sufficient to result in gene suppression if the nucleic acid sequence is delivered in the antisense orientation.

Host: A cell, tissue or organism capable of replicating a nucleic acid such as a vector or plant viral nucleic acid and which is capable of being infected by a virus containing the viral vector or viral nucleic acid. This term is intended to include prokaryotic and eukaryotic cells, organs, tissues or organisms, where appropriate. Bacteria, fungi, yeast, animal (cell, tissues, or organisms), and plant (cell, tissues, or organisms) are examples of a host.

Infection: The ability of a virus to transfer its nucleic acid to a host or introduce a viral nucleic acid into a host, wherein the viral nucleic acid is replicated, viral proteins are synthesized, and new viral particles assembled. In this context, the terms "transmissible" and "infective" are used interchangeably herein. The term is also meant to include the ability of a selected nucleic acid sequence to integrate into a genome, chromosome or gene of a target organism.

Multigene family: A set of genes descended by duplication and variation from some ancestral gene. Such genes may be clustered together on the same chromosome or dispersed on different chromosomes. Examples of multigene families include those which encode the histones, hemoglobins, immunoglobulins, histocompatibility antigens, actins, tubulins, keratins, collagens, heat shock proteins, salivary glue proteins, chorion proteins, cuticle proteins, yolk proteins, and phaseolins.

Non-Native: Any RNA or DNA sequence that does not normally occur in the cell or organism in which it is placed. Examples include recombinant plant viral nucleic acids and genes or ESTs contained therein. That is, an RNA or DNA sequence may be non-native with respect to a viral nucleic acid. Such an RNA or DNA sequence would not naturally occur in the viral nucleic acid. Also, an RNA or DNA sequence may be non-native with respect to a host organism. That is, such a RNA or DNA sequence would not naturally occur in the host organism.

Nucleic acid: As used herein the term is meant to include any DNA or RNA sequence from the size of one or more nucleotides up to and including a complete gene sequence. The term is intended to encompass all nucleic acids whether naturally occurring in a particular cell or organism or non-naturally occurring in a particular cell or organism.

Nucleic acid of interest: The term is intended to refer to the nucleic acid sequence whose function is to be determined. The sequence will normally be non-native to a viral vector but may be native or non-native to a host organism.

Phenotypic Trait: An observable, measurable or detectable property resulting from the expression or suppression of a gene or genes.

Plant Cell: The structural and physiological unit of plants, consisting of a protoplast and the cell wall.

Plant Organ: A distinct and visibly differentiated part of a plant, such as root, stem, leaf or embryo.

Plant Tissue: Any tissue of a plant in planta or in culture. This term is intended to include a whole plant, plant cell, plant organ, protoplast, cell culture, or any group of plant cells organized into a structural and functional unit.

Positive-sense inhibition: A type of gene regulation based on cytoplasmic inhibition of gene expression due to the presence in a cell of an RNA molecule substantially homologous to at least a portion of the mRNA being translated.

Promoter: The 5'-flanking, non-coding sequence substantially adjacent a coding sequence which is involved in the initiation of transcription of the coding sequence.

Protoplast: An isolated plant or bacterial cell without some or all of its cell wall.

Recombinant Plant Viral Nucleic Acid: Plant viral nucleic acid which has been modified to contain non-native nucleic acid sequences. These non-native nucleic acid sequences may be from any organism or purely synthetic, however, they may also include nucleic acid sequences naturally occurring in the organism into which the recombinant plant viral nucleic acid is to be introduced.

Recombinant Plant Virus: A plant virus containing the recombinant plant viral nucleic acid.

Subgenomic Promoter: A promoter of a subgenomic mRNA of a viral nucleic acid.

Substantial Sequence Homology: Denotes nucleotide sequences that are substantially functionally equivalent to one another. Nucleotide differences between such sequences having substantial sequence homology are insignificant in affecting function of the gene products or an RNA coded for by such sequence.

Systemic Infection: Denotes infection throughout a substantial part of an organism including mechanisms of spread other than mere direct cell inoculation but rather including transport from one infected cell to additional cells either nearby or distant.

Transposon: A nucleotide sequence such as a DNA or RNA sequence which is capable of transferring location or moving within a gene, a chromosome or a genome.

Transgenic plant: A plant which contains a foreign nucleotide sequence inserted into either its nuclear genome or organellar genome.

Transcription: Production of an RNA molecule by RNA polymerase as a complementary copy of a DNA sequence or subgenomic mRNA.

Transient Expression: expression of a nucleic acid sequence in a host without insertionof the nucleic acid sequence into the host genome, such as by way of a viral vector.

Vector: A self-replicating RNA or DNA molecule which transfers an RNA or DNA segment between cells, such as bacteria, yeast, plant, or animal cells.

Virus: An infectious agent composed of a nucleic acid which may or may not be encapsidated in a protein. A virus may be a mono-, di-, tri-, or multi-partite virus, as described above.

EXAMPLES

The following examples further illustrate the present invention. These examples are intended merely to be illustrative of the present invention and are not to be construed as being limiting.

Example 1

Gene Silencing/co-supression of Genes Induced by Delivering an RNA Capable of Base Pairing with Itself to form Double Stranded Regions Gene silencing has been used to down regulate gene expression in transgenic plants. Recent experimental evidence suggests that double stranded RNA may be an effective stimulator of gene silencing/co-suppression phenomenon in transgenic plant. For example, Waterhouse et al. (*Proc. Natl. Acad. Sci.* USA 95:13959–13964 (1998), incorporated herein by reference) described that virus resistance and gene silencing in plants could be induced by simultaneous expression of sense and antisense RNA. Gene silencing/co-suppression of plant genes may be induced by delivering an RNA capable of base pairing with itself to form double stranded regions.

This example shows: (1) a novel method for generating an RNA virus vector capable of producing an RNA capable of forming double stranded regions, and (2) a process to silence plant genes by using such a viral vector.

Step 1: Construction of a DNA sequence which after it is transcribed would generate an RNA molecule capable of base pairing with itself. Two identical, or nearly identical, ds DNA sequences are ligated together in an inverted orientation to each other (i.e., in either a head to tail or tail to head orientation) with or without a linking nucleotide sequence between the homologous sequences. The resulting DNA sequence is then be cloned into a cDNA copy of a plant viral vector genome.

Step 2: Cloning, screening, transcription of clones of interest using known methods in the art.

Step 3: Infect plant cells with transcripts from clones.

As virus expresses foreign gene sequence, RNA from foreign gene forms base pair upon itself, forming double-stranded RNA regions. This approach is used with any plant or non-plant gene and used to silence plant gene homologous to assist in identification of the function of a particular gene sequence.

Example 2

Cytolasmic Inhibition of Phytoene Desaturase in Transfected Plant Confirms that the Partial Tomato PDS Sequence Encodes Phytoene Desaturase Isolation of tomato mosaic virus cDNA. An 861 base pair fragment (5524–6384) from the tomato mosaic virus (fruit necrosis strain F; tom-F) containing the putative coat protein subgenomic promoter, coat protein gene, and the 3'-end was isolated by PCR using primers 5'-CTCGCAAAGTTTCGAACCAAATCCTC-3' (upstream) (SEQ ID NO: 1) and 5'-CGGGGTACCTGGGCCCCAACCGGGGGTTCCGGG GG-3' (downstream) (SEQ ID NO: 2) and subcloned into the HincII site of pBluescript KS-. A hybrid virus consisting of TMV-U1 and ToMV-F was constructed by swapping an 874-bp BamHI-KpnI ToMV fragment into pBGC152, creating plasmid TTO1. The inserted fragment was verified by dideoxynucleotide sequencing. A unique AvrII site was inserted downstream of the XhoI site in TTO1 by PCR mutagenesis, creating plasmid TTO1A, using the following oligonucleotides:
5'-TCCTCGAGCCTAGGCTCGCAAAGTTTCGAACCAA ATCCTCA-3' (upstream) (SEQ ID NO: 3), 5'-CGGGGTACCTGGGCCCCAACCGGGGGTTCCGGG GG-3' (downstream) (SEQ ID NO: 4).

Isolation of a partial cDNA encoding tomato phytoene desaturase. Partial cDNAs were isolated from ripening tomato fruit RNA by polymerase chain reaction (PCR) using the following oligonucleotides: PDS, 5'-TGCTCGAGTGTGTTCTTCAGTTTTCTGTCA-3' (SEQ ID NO: 5) (upstream), 5'-AACTCGAGCGCTTTGATTTCTCCGAAGCTT-3' (downstream) (SEQ ID NO: 6). Approximately 3×10⁴ colonies from a Lycopersicon esculentum cDNA library were screened by colony hybridization using a ³²p labeled tomato phytoene desaturase PCR product. Hybridization was carried out at 42° C. for 48 hours in 50% formamide, 5×SSC, 0.02 M phosphate buffer, 5×Denhart's solution, and 0.1 mg/ml sheared calf thymus DNA. Filters were washed at 65° C. in 0.1×SSC, 0.1% SDS prior to autoradiography. PCR products and the phytoene desaturase cDNA clones were verified by dideoxynucleotide sequencing.

DNA sequencing and computer analysis. A PstI, BamnHI fragment containing the phytoene synthase cDNA and the partial phytoene desaturase cDNA was subcloned into pBluescript® KS+(Stratagene, La Jolla, Calif.). The nucleotide sequencing of KS+/PDS #38 was carried out by dideoxy termination using single-stranded templates (Maniatis, *Molecular Cloning*, 1ˢᵗ Ed.) Nucleotide sequence analysis and amino acid sequence comparisons were performed using PCGENE® and DNA Inspector® IIE programs.

Construction of a viral vector containing a partial tomato phytoene desaturase cDNA. A XhoI fragment containing the partial tomato phytoene desaturase cDNA was subcloned into TTO1. The vector TTO1A/PDS+ (FIG. 1) contains the phytoene desaturase cDNA in the positive orientation under the control of the TMV-U1 coat protein subgenomic promoter; while the vector TTO1A/PDS—contains the phytoene desaturase cDNA in the antisense orientation.

Analysis of *N. benthamiana* transfected by TTO1/PDS+, and TTO1/PDS–. Infectious RNAs from TTO1/PDS+, TTO1/PDS+ were prepared by in vitro transcription using SP6 DNA-dependent RNA polymerase as described previously (Dawson et al., *Proc. Natl. Acad. Sci.* USA 83:1832 (1986)) and were used to mechanically inoculate *N. benthamiana*. The hybrid viruses spread throughout all the non-inoculated upper leaves as verified by transmission electron microscopy, local lesion infectivity assay, and polymerase chain reaction (PCR) amplification. The viral symptoms resulting from the infection consisted of distortion of systemic leaves and plant stunting with mild chlorosis. The leaves from plants transfected with TTO1/PDS+ and TTO1/PDS− turned white. Agarose gel eletrophoresis of PCR cDNA isolated from virion RNA and Northern blot analysis of virion RNA indicate that the vectors are maintained in an extrachromosomal state and have not undergone any detectable intramolecular rearrangements.

Purification and analysis of carotenoids from transfected plants. The carotenoids were isolated from systemically infected tissue and analyzed by HPLC chromatography. Carotenoids were extracted in ethanol and identified by their peak retention time and absorption spectra on a 25-cm Spherisorb® ODS-15-m column using acetonitrile/methanol/2-propanol (85:10:5) as a developing solvent at a flow rate of 1 ml/min. They had identical retention time to a synthetic phytoene standard and β-carotene standards from carrot and tomato. The expression of sense and antisense RNA to a partial phytoene desaturase in transfected plants inhibited the synthesis of colored carotenoids and caused the systemically infected leaves to turn white. HPLC analysis of these plants revealed that they also accumulated phytoene. The white leaf phenotype was also observed in plants treated with the herbicide norflurazon which specifically inhibits phytoene desaturase.

Our results that phytoene accumulated in plants transfected with antisense phytoene desaturase suggests that viral vectors can be used as a potent tool to manipulate pathways in the production of secondary metabolites through cytoplasmic antisense inhibition. Leaves from systemically infected TTO1A/PDS+ plants also accumulated phytoene and developed a bleaching white phenotype; the actual mechanism of inhibition is not clear. These data are presented by Kumagai et al., *Proc. Natl. Acad. Sci.* USA 92:1679–1683 (1995).

Example 3

Figure 2:
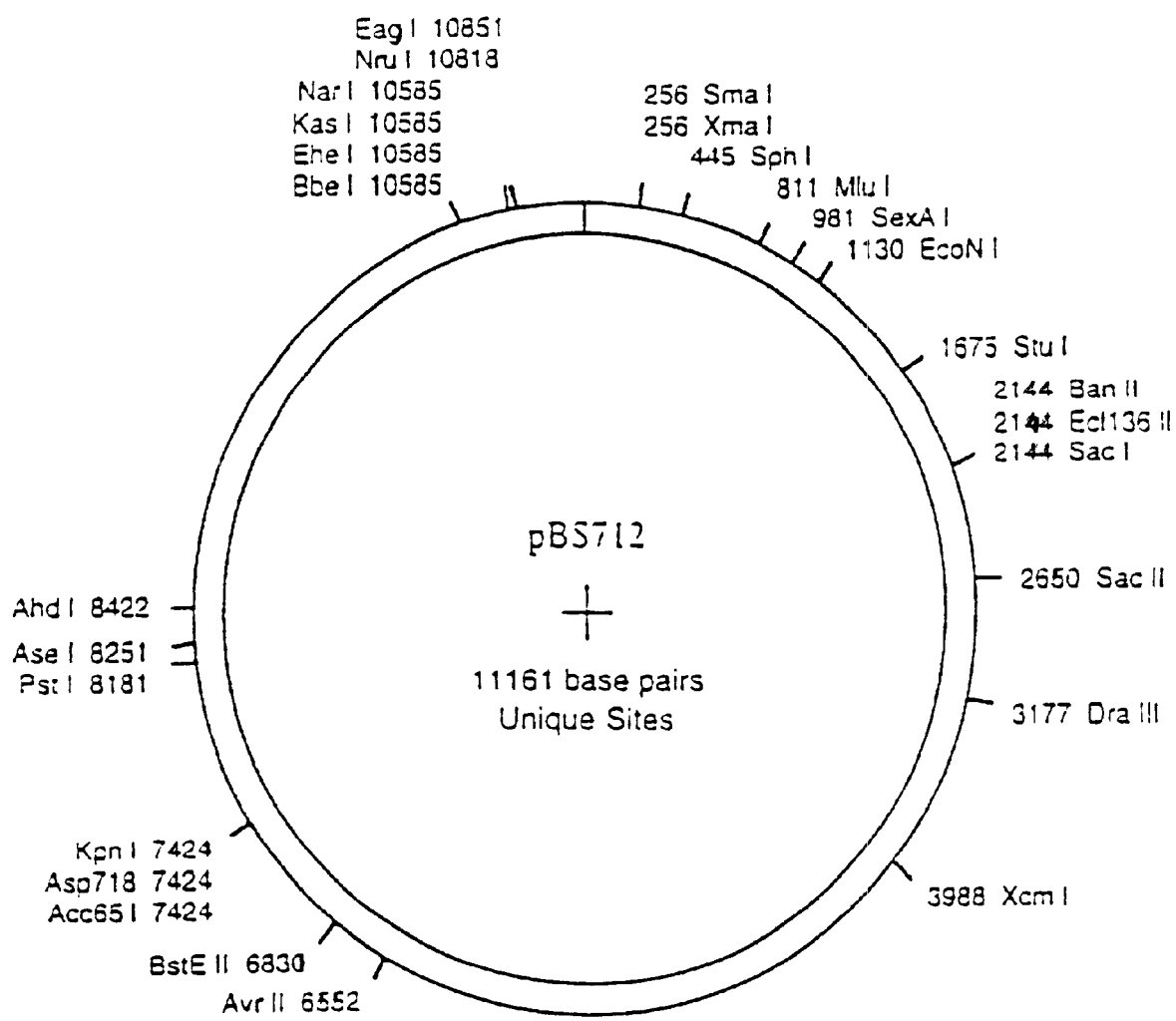
FIG. 2 depicts the plasmid pBS #712.

Cytoplasmic Inhibition of 5-enolpyruvylshikimate-3-phosphate Synthase (EPSPS) Genes in Plants Blocks Aromatic Amino Acid Biosynthesis Cytoplasmic inhibition of 5-enolpyruvylshikimate-3-phosphate synthase (EPSPS) genes in plants blocks aromatic amino acid biosynthesis and causes a systemic bleaching phenotype similar to Roundup® herbicide. See also della-Cioppa, et al., "Genetic Engineering of herbicide resistance in plants," *Frontiers of Chemistry: Biotechnology*, Chemical Abstract Service, ACS, Columbus, Ohio, pp. 665–70 (1989). A dual subgenomic promoter vector encoding 1097 base pairs of an antisense EPSPS gene from *Nicotiana tabacum* (Class I EPSPS) is shown in plasmid pBS712. FIG. 2 shows plasmid pBS712. Systemic expression of the *Nicotiana tabacum* Class I EPSPS gene in the antisense orientation causes a systemic bleaching phenotype similar to Roundup® herbicide.

Example 4

Exemplary Complementation Analysis.

A transgenic plant or naturally occurring plant mutant may have a non-functional gene such as the one which produces EPSPS. A plant deficient or lacking in the EPSPS gene could grow only in the presence of added aromatic amino acids. Transfection of plants with a viral vector containing a functional EPSPS gene or CDNA sequence encoding the same would cause the plant to produce a functional EPSPS gene product. A plant so transfected would then be able to grow normally without added aromatic amino acids to its environment. In this transfected plant, the EPSPS mutation in the plant would be complemented in trans by the viral nucleic acid sequence containing the native or foreign EPSPS cDNA sequence.

Example 5

Construction of a Tobamoviral Vector for Expression of Heterologous Genes in *A. thaliana*

Virions that were prepared as a crude aqueous extract of tissue from turnip infected with Ribgrass mosaic virus (RMV) were used to inoculate *N. benthamiana, N. tabacum, A. thaliana*, and oilseed rape (canola). Two to three weeks after transfection, systemically infected plants were analyzed by immunoblotting, using purified RMV as a standard. Total soluble plant protein concentrations were determined using bovine serum albumin as a standard. The proteins were analyzed on a 0.1% SDS/12.5% polyacrylamide gel and transferred by electroblotting for 1 hr to a nitrocellulose membrane. The blotted membrane was incubated for 1 hr with a 2000-fold dilution of anti-ribgrass mosaic virus coat antiserum. Using standard protocols, the antisera was raised in rabbits against purified RMV coat protein. The enhanced chemiluminescence horseradish peroxidase-linked, goat anti-rabbit IgG assay (Cappel Laboratories) was performed according to the manufacturer's (Amersham) specifications. The blotted membrane was subjected to film exposure times of up to 10 sec. No detectable cross-reacting protein was observed in the noninfected *N. benthamiana* control plant extracts. A 18 kDa protein cross-reacted to the anti-RMV coat antibody from systemically infected *N. benthamiana, N. tabacum, A. thaliana*, and oilseed rape (canola). This result demonstrates that RMV can systemically infect *N. benthamiana, N. tabacum, A. thaliana*, and oilseed rape (canola).

Plasmid Constructions.

Figure 3:
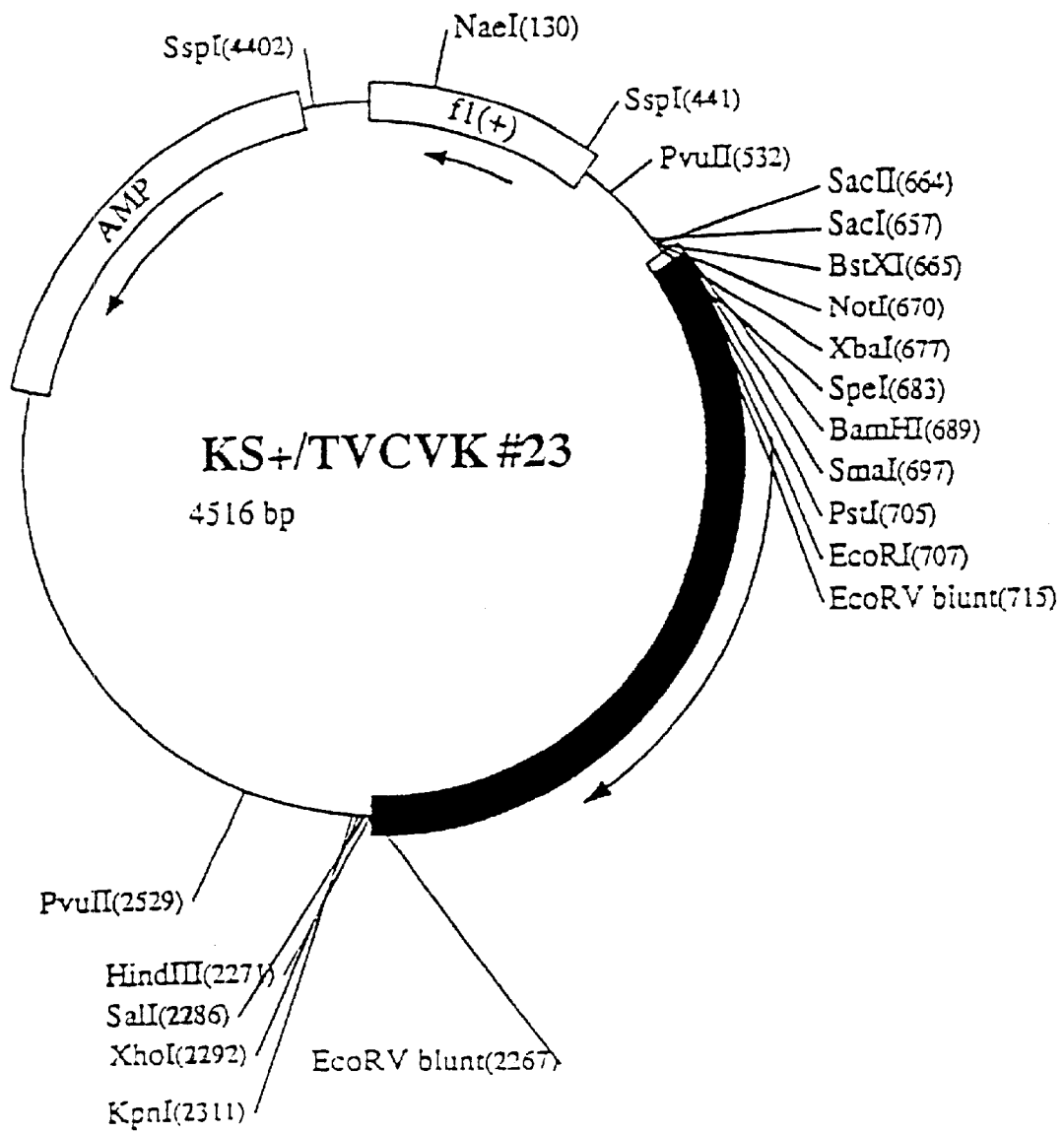
FIG. 3 depicts the plasmid KS+TVCVK #23.

Ribgrass mosaic virus (RMV) is a member of the tobamovirus group that infects crucifers. A partial RMV cDNA containing the 30K subgenomic promoter, 30K ORF, coat subgenomic promoter, coat ORF, and 3'-end was isolated by RT-PCR using by using oligonucleotides TVCV183x, 5'-TAC TCG AGG TTC ATA AGA CCG CGG TAG GCG G-3' (upstream) (SEQ ID NO: 7) and TVCV KpnI, 5'-CGG GGT ACC TGG GCC CCT ACC CGG GGT TTA GGG AGG-3' (downstream) (SEQ ID NO: 8), and subcloned into the EcoRV site of KS+, creating plasmid KS+ TVCV #23 (FIG. 3).

The RMV cDNA was characterized by restriction mapping and dideoxy nucleotide sequencing. The partial nucleotide sequence is as follows:

5-CTCGAGGTTCATAAGACCGCGGTAGGCGGAGC GTTTGTTTACTGTAGTATAA TTAAATATTTGT- CAGATAAAAGGTTGTTTAAA- GATTTGTTTTTTGTTTGACTG AGTCGATAAT- GTCTTACGAGCCTAAAGTTAGTGACTTCCTTGC TCTTACGAA AAAGGAGGAAATTTTACCCAAG- GCTTTGACGAGATTAAAGACTGTCTCTATT AGTACTAAGGATGTTATATCTGTTAAG- GAGTCTGAGTCCCTGTGTGATATTG ATTTGT- TAGTGAATGTGCCATTAGATAAGTATAG- GTATGTGGGTGTTTTGGG TGTTGTTTTCACCGGTGAATGGCTGG- TACCGGATTTCGTTAAAGGTGGGGTA ACAGT- GAGCGTGATTGACAAACGGCTTGAAAAT- TCCAGAGAGTGCATAATT GGTACGTACCGAGCTGCTGTAAAGGACA- GAAGGTTCCAGTTCAAGCTGGTT CCAAAT- TACTTCGTATCCATTGCGGATGCCAAGC- GAAAACCGTGGCAGGTT CATGTGCGAATTCAAAATCTGAAGATC- GAAGCTGGATGGCAACCTCTAGCT CTAGAG- GTGGTTTCTGTTGCCATGGTTAC- TAATAACGTGGTTGTTAAAGGTT TGAGGGAAAAGGTCATCGCAGTGAAT- GATCCGAACGTCGAAGGTTTCGAAG GTGTG- GTTGACGATTTCGTCGATTCGGTTGCTG- CATTCAAGGCGATTGACAG TTTCCGAAAGAAAAAGAAAAAGATTG- GAGGAAGGGATGTAAATAATAATA AGTATA- GATATAGACCGGAGAGATACGCCGGTC- CTGATTCGTTACAATATA AAGAAGAAAATGGTTTACAACATCAC- GAGCTCGAATCAGTACCAGTATTTC GCAGC- GATGTGGGCAGAGCCCACAGCGATGCT- TAACCAGTGCGTGTCTGCG TTGTCGCAATCGTATCAAACTCAGGCG- GCAAGAGATACTGTTAGACAGCAG TTCTCTAACCTTCTGAGTGCGATTGTGA- CACCGAACCAGCGGTTTCCAGAAA CAG- GATACCGGGTGTATATTAATTCAGCAGT- TCTAAAACCGTTGTACGAGTC TCTCATGAAGTCCTTTGATACTAGAAAT- AGGATCATTGAAACTGAAGAAGA GTCGCGTC- CATCGGCTTCCGAAGTATCTAATGCAA- CACAACGTGTTGATGAT GCGACCGTGGCCATCAGGAGTCAAAT- TCAGCTTTTGCTGAACGAGCTCTCCA ACGGA- CATGGTCTGATGAACAGGGCAGAGTTC- GAGGTTTTATTACCTTGGG CTACTGCGCCAGCTACATAGGCGTGGTG- CACACGATAGTGCATAGTGTTTTT CTCTC- CACTTAAATCGAAGAGATATACTTACG- GTGTAATTCCGCAAGGGTGG CGTAAACCAAATTACGCAATGTTTTAG- GTTCCATTTAAATCGAAACCTGTTA TTTCCTG- GATCACCTGTTAACGTACGCGTGGCG- TATATTACAGTGGGAATAA CTAAAAGTGAGAGGTTCGAATCCTC- CCTAACCC CGGGTAGGGGCCCA-3'(SEQ ID NO: 9).

The 1543 base pair from the partial RMV cDNA was compared (PCGENE) to oilseed rape mosaic virus (ORMV). The nucleotide sequence identity was 97.8%. The RMV 30K and coat ORF were compared to ORMV and the amino acid identity was 98.11% (30K) and 98.73% (coat), respectively. A partial RMV cDNA containing the 5'-end and part of the replicase was isolated by RT-PCR from RMV RNA using oligonucleotides RGMV1 5'-GAT GGC GCC TTA ATA CGA CTC ACT ATA GTT TTA TTT TTG TTG CAA CAA CAA CAA C-3' (upstream) (SEQ ID NO: 10) and RGR 132 5'-CTT GTG CCC TTC ATG ACG AGC TAT ATC ACG-3' (downstream) (SEQ ID NO: 11). The RMV cDNA was characterized by dideoxy nucleotide sequencing. The partial nucleotide sequence containing the T7 RNA polymerase nromoter and part of the RMV cDNA is as follows:

5'-ccttaatacgactcactataGTTTTATTTTTGTTGCAACAAC AACAACAAATTACAATAA CAACAAAA- CAAATACAAACAACAACAACATGGCA- CAATTTCAACAAACAG TAAACATGCAAACAT- TGCAGGCTGCCGCAGGGCGCAACAGCCTGGTG AATG ATTTAGCCTCACGACGTGTTTATGA- CAATGCTGTCGAGGAGCTAAATGCACG CTC- GAGACGCCCTAAGGTTCATTACTC- CAAATCAGTGTCTACGGAACAGAC GCTGTTAGCTTCAAACGCTTATCCG- GAGTTTGAGATTTCCTTTACTCATACCC AACAT- GCCGTACACTCCCTTGCGGGTGGC- CTAAGGACTCTTGAGTTAGAGTA TCTCATGATGCAAGTTCCGTTCGGT- TCTCTGACGTACGACATCGGTGGTAAC TTTG- CAGCGCACCTTTTCAAAGGACGCGAC- TACGTTCACTGCTGTATGCCAA ACTTGGATGT ACGTGATATAGCT-3' (SEQ ID NO: 12). The uppercase letters are nucieotide sequences from RMV cDNA. The lower case letters are nucleotide sequences from T7 RNA polymerase promoter. The nucleotide sequences from the 5' and 3' oligonucleotides are underlined.

Full length infectious RMV cDNA clones were obtained by RT-PCR from RMV RNA using oligonucleotides RGMV1, 5'-GAT GGC GCC TTA ATA CGA CTC ACT ATA GTT TTA TTT TTG TTG CAA CAA CAA CAA C-3' (upstream) (SEQ ID NO: 13) and RG1 APE, 5'-ATC GTT TAA ACT GGG CCC CTA CCC GGG GTT AGG GAG G-3' (downstream) (SEQ ID NO: 14). The RMV cDNA was characterized by dideoxy nucleotide sequencing. The partial nucleotide sequence containing the T7 RNA polymerase promoter and part of the RMV cDNA is as follows:

5'-CCTTAATACGACTCACTATAGTTTTATTTTTGTT GCAACAACAACAACAAAT TACAATAACAA- CAAAACAAATACAAACAACAACAACATG- GCACAATTTCAA CAAACAGTAAACATGCAAA- CATTCCAGGCTGCCGCAGGGCGCAACAGCCTG GTGAATGATTTAGCCTCACGACGTGTT- TATGACAATGCTGTCGAGGAGCTAA ATG- CACGCTCGAGACGCCCTAAGGTTCAT- TACTCCAAATCAGTGTCTACGGA ACAGACGCTGTTAGCTTCAAACGCT- TATCCGGAGTTTGAGATTTCCTTTACT CATAC- CCAAACATGCCGTACACTCCCT- TGCGGGTGGCCTAAGGACTCTTGAG TTAGAGTATCTCATGATGCAAGTTCCGT- TCGGTTCTCTGACGTACGACATCG GTGG- TAACTTTGCAGCGCACCTTTTCAAAG- GACGCGACTACGTTCACTGCTG TATGCCAAACTTGGATGTACGTGATATAGCT-3'

(SEQ ID NO: 15). The uppercase letters are nucleotide sequences from RMV CDNA. The nucleotide sequences from the 5' and 3' oligonucleotides are underlined. Full length infectious RMV CDNA clones were obtained by RT-PCR from RMV RNA using oligonucleotides RGMV1, 5'-gat ggc gcc tta ata cga ctc act ata gtt tta ttt ttg ttg caa caa caa caa c-3' (upstream) (SEQ ID NO: 16) and RG1 APE, 5'-ATC GTT TAA ACT GGG CCC CTA CCC GGG GTT AGG GAG G-3' (downstream) (SEQ ID NO: 17).

Example 6

*Arabidopsis thaliana* cDNA Library Construction in a Dual Subgenomic Promoter Vector

*Arabidopsis thaliana* cDNA libraries obtained from the Arabidopsis Biological Resource Center (ABRC). The four libraries from ABRC were size-fractionated with inserts of 0.5–1 kb (CD4-13), 1–2 kb (CD4-14), 2–3 kb (CD4-15), and 3–6 kb (CD4-16). All libraries are of high quality and have been used by several dozen groups to isolate genes. The pBluescript® phagemids from the Lambda ZAP II vector were subjected to mass excision and the libraries were recovered as plasmids according to standard procedures.

Figure 4:
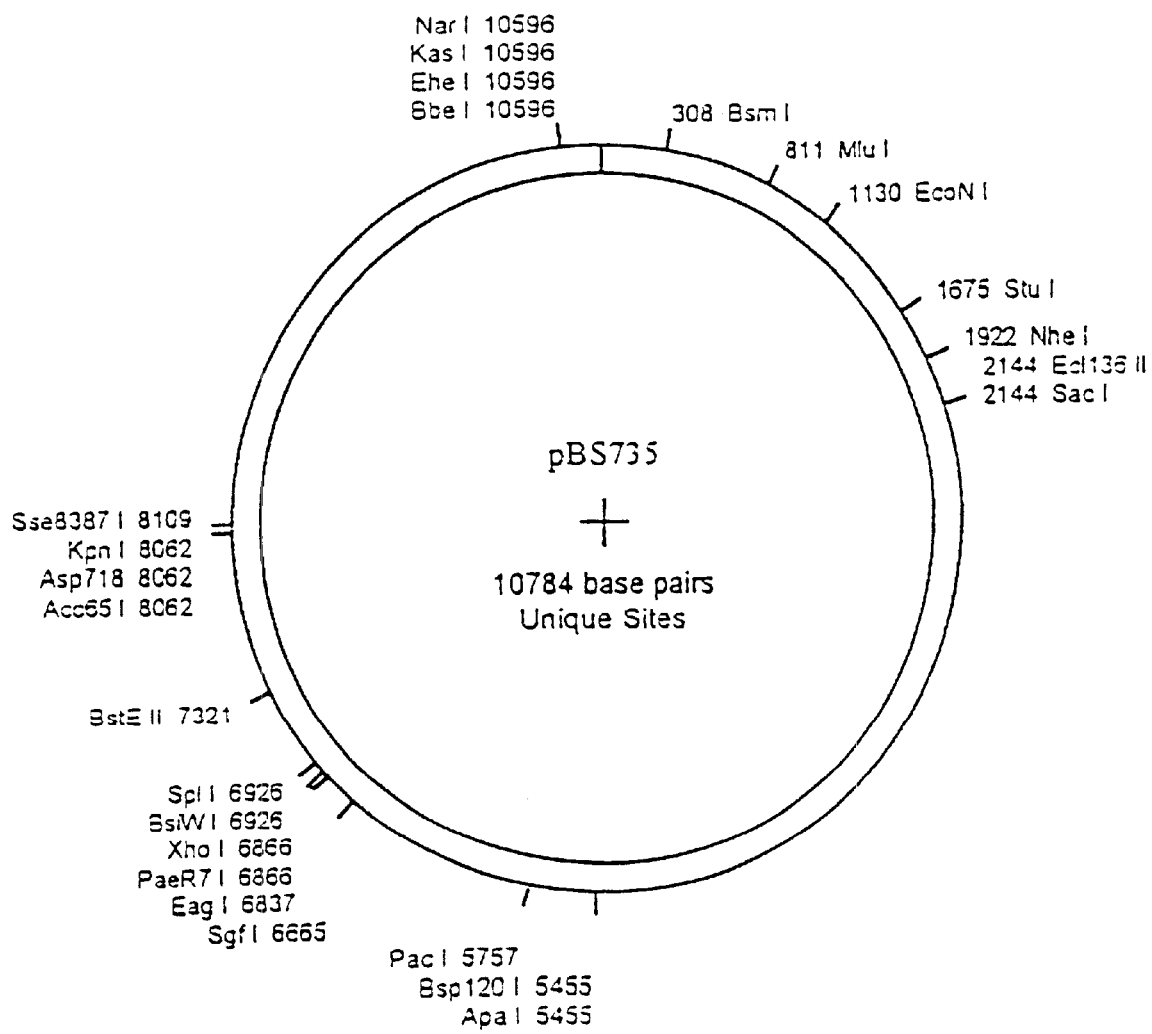
FIG. 4 depicts the plasmid pBS #735.
Figure 5:
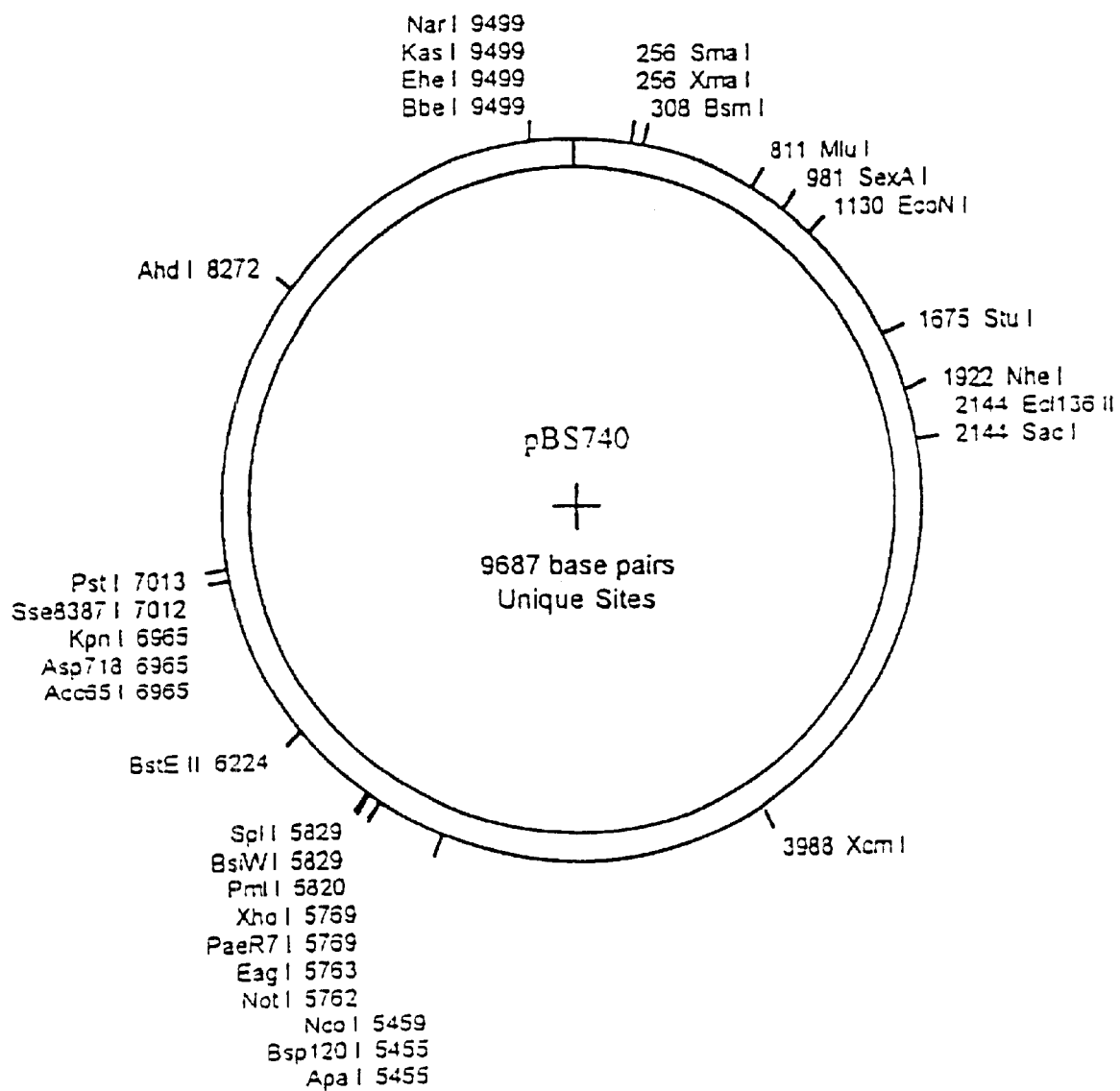
FIG. 5 depicts the plasmid pBS #740.

Alternatively, the CDNA inserts in the CD4-13 (Lambda ZAP II vector) were recovered by digestion with NotI. Digestion with NotI in most cases liberated the entire *Arabidopsis thaliana* cDNA insert because the original library was assembled with NotI adapters. NotI is an 8-base cutter that infrequently cleaves plant DNA. In order to insert the NotI fragments into a transcription plasmid, the pBS735 transcription plasmid (FIG. 4) was digested with PacI/XhoI and ligated to an adapter DNA sequence created from the oligonucleotides 5'-TCGAGCGGCCGCAT-3' (SEQ ID NO: 18) and 5'-GCGGCCGC-3' (SEQ ID NO: 19). The resulting plasmid pBS740 (FIG. 5) contains a unique NotI restriction site for bidirectional insertion of NotI fragments from the CD4-13 library. Recovered colonies were prepared from these for plasmid minipreps with a Qiagen BioRobot9600®. The plasmid DNA preps performed on the BioRobot9600® are done in 96-well format and yield transcription quality DNA. An Arabidopsis cDNA library was transformed into the plasmid and analyzed by agarose gel electrophoresis to identify clones with inserts. Clones with inserts are transcribed in vitro and inoculated onto *N. benthamiana* or *Arabidopsis thaliana*. Selected leaf disks from transfected plants are then taken for biochemical analysis.

Example 7

High Throughput Robotics.

The efficiency of inoculation of subject organisms such as plants is improved by using means of high throughput robotics. For example, host plants such as *Arabidopsis thaliana* were grown in microtiter plates such as the standard 96-well and 384-well microtiter plates. A robotic handling arm then moved the plates containing the organism to a colony picker or other robot that delivered inoculations to each plant in the well. By this procedure, inoculation was performed in a very high speed and high throughput manner. It is preferable that the plant is a germinating seed or at least in the development cycle to enable access to the cells to be transfected. Equipment used for automated robotic production line include, but not be limited to, robots of these types: electronic multichannel pipetmen, Qiagen BioRobot9600®, Robbins Hydra liquid handler, Flexys Colony Picker, New Brunswick automated plate pourer, GeneMachines HiGro shaker incubator, New Brunswick floor shaker, three Qiagen BioRobots, MJ Research PCR machines (PTC-200, Tetrad), ABI 377 sequencer and Tecan Genesis RSP200 liquid handler.

Example 8

Genomic DNA Library Construction in a Recombinant Viral Nucleic Acid Vector Genomic DNAs represented in BAC (bacterial artificial chromosome) or YAC (yeast artificial chromosome) libraries are obtained from the Arabidopsis Biological Resource Center (ABRC). The BAC/YAC DNAs are mechanically size-fractionated, ligated to adapters with cohesive ends, and shotgun-cloned into recombinant viral nucleic acid vectors. Alternatively, mechanically size-fractionated genomic DNAs are blunt-end ligated into a recombinant viral nucleic acid vector. Recovered colonies are prepared for plasmid minipreps with a Qiagen BioRobot9600®. The plasmid DNA preps done on the BioRobot9600® are assembled in 96-well format and yield transcription quality DNA. The recombinant viral nucleic acid/Arabidopsis genomic DNA library is analyzed by agarose gel electrophoresis (template quality control step) to identify clones with inserts. Clones with inserts are then transcribed in vitro and inoculated onto *N. benthamiana* and/or *Arabidopsis thaliana*. Selected leaf disks from transfected plants are then be taken for biochemical analysis.

Genomic DNA from Arabidopsis typically contains a gene every 2.5 kb (kilobases) on average. Genomic DNA fragments of 0.5 to 2.5 kb obtained by random shearing of DNA were shotgun assembled in a recombinant viral nucleic acid expression/knockout vector library. Given a genome size of Arabidopsis of approximately 120,000 kb, a random recombinant viral nucleic acid genomic DNA library would need to contain minimally 48,000 independent inserts of 2.5 kb in size to achieve 1X coverage of the Arabidopsis genome. Alternatively, a random recombinant viral nucleic acid genomic DNA library would need to contain minimally 240,000 independent inserts of 0.5 kb in size to achieve 1X coverage of the Arabidopsis genome. Assembling recombinant viral nucleic acid expression/knockout vector libraries from genomic DNA rather than cDNA has the potential to overcome known difficulties encountered when attempting to clone rare, low-abundance mRNA's in a cDNA library. A recombinant viral nucleic acid expression/knockout vector library made with genomic DNA would be especially useful as a gene silencing knockout library. In addition, the Dual Heterologous Subgenomic Promoter Expression System (DHSPES) expression/knockout vector library made with genomic DNA would be especially useful for expression of genes lacking introns. Furthermore, other plant species with moderate to small genomes (e.g. rose, approximately 80,000 kb) would be especially useful for recombinant viral nucleic acid expression/knockout vector libraries made with genomic DNA. A recombinant viral nucleic acid expression/knockout vector library can be made from existing BAC/YAC genomic DNA or from newly-prepared genomic DNAs for any plant species.

Example 9

Genomic DNA or cDNA Library Construction in a DHSPES Vector, and Transfection of Individual Clones from said Vector Library onto T-DNA Tagged or Transposon Tagged or Mutated Plants Genomic DNA or cDNA library construction in a recombinant viral nucleic acid vector, and transfection of individual clones from the vector library onto T-DNA tagged or transposon tagged or mutated plants may be performed according to the procedure set forth in Example 7. Such a protocol may be easily designed to complement mutations introduced by random insertional mutagenesis of T-DNA sequences or transposon sequences.

Example 10

Identification of Nucleotide Sequences Involved in the Regulation of Plant Growth by Cytoplasmic Inhibition of Gene Expression using Viral Derived RNA (GTP binding proteins)

In the following examples, we show: (1) a method for producing antisense RNA using an RNA viral vector, (2) a method to produce viral-derived antisense RNA in the cytoplasm, (3) a method to inhibit the expression of endogenous plant proteins in the cytoplasm by viral antisense RNA, and (4) a method to produce transfected plants containing viral antisense RNA, such method is much faster than the time required to obtain genetically engineered antisense transgenic plants. Systemic infection and expression of viral antisense RNA occurs as short as four days post inoculation, whereas it takes several months or longer to create a single transgenic plant. These examples demonstrates that novel positive strand viral vectors, which replicate solely in the cytoplasm, can be used to identify genes involved in the regulation of plant growth by inhibiting the expression of specific endogenous genes. These examples enable one to characterize specific genes and biochemical pathways in transfected plants using an RNA viral vector.

Tobamoviral vectors have been developed for the heterologous expression of uncharacterized nucleotide sequences in transfected plants. A partial *Arabidopsis thaliana* cDNA library was placed under the transcriptional control of a tobamovirus subgenomic promoter in a RNA viral vector. Colonies from transformed *E. coli* were automatically picked using a Flexys robot and transferred to a 96 well flat bottom block containing terrific broth (TB) Amp 50 ug/ml. Approximately 2000 plasmid DNAs were isolated from overnight cultures using a BioRobot and infectious RNAs from 430 independent clones were directly applied to plants. One to two weeks after inoculation, transfected *Nicotiana benthamiana* plants were visually monitored for changes in growth rates, morphology, and color. One set of plants transfected with 740 AT #120 were severely stunted. DNA sequence analysis revealed that this clone contained an Arabidopsis GTP binding protein open reading frame (ORF) in the antisense orientation. This demonstrates that an episomal RNA viral vector can be used to deliberately alter the metabolic pathway and cause plant stunting. In addition, our results suggest that the Arabidopsis antisense transcript can turn off the expression of the *N. benthamiana* gene.

Construction of an *Arabidopsis thaliana* cDNA Library in an RNA Viral Vector An *Arabidopsis thaliana* CD4-13 cDNA library was digested with NotI. DNA fragments between 500 and 1000 bp were isolated by trough elution and subcloned into the NotI site of pBS740. *E. coli* C600 competent cells were transformed with the pBS740 AT library and colonies containing Arabidopsis cDNA sequences were selected on LB Amp 50 ug/ml. Recombinant C600 cells were automatically picked using a Flexys robot and then transferred to a 96 well flat bottom block containing terrific broth (TB) Amp 50 ug/ml. Approximately 2000 plasmid DNAs were isolated from overnight cultures using a BioRobot (Qiagen) and infectious RNAs from 430 independent clones were directly applied to plants.

Isolation of a Gene Encoding a GTP Binding Protein

Figure 6:
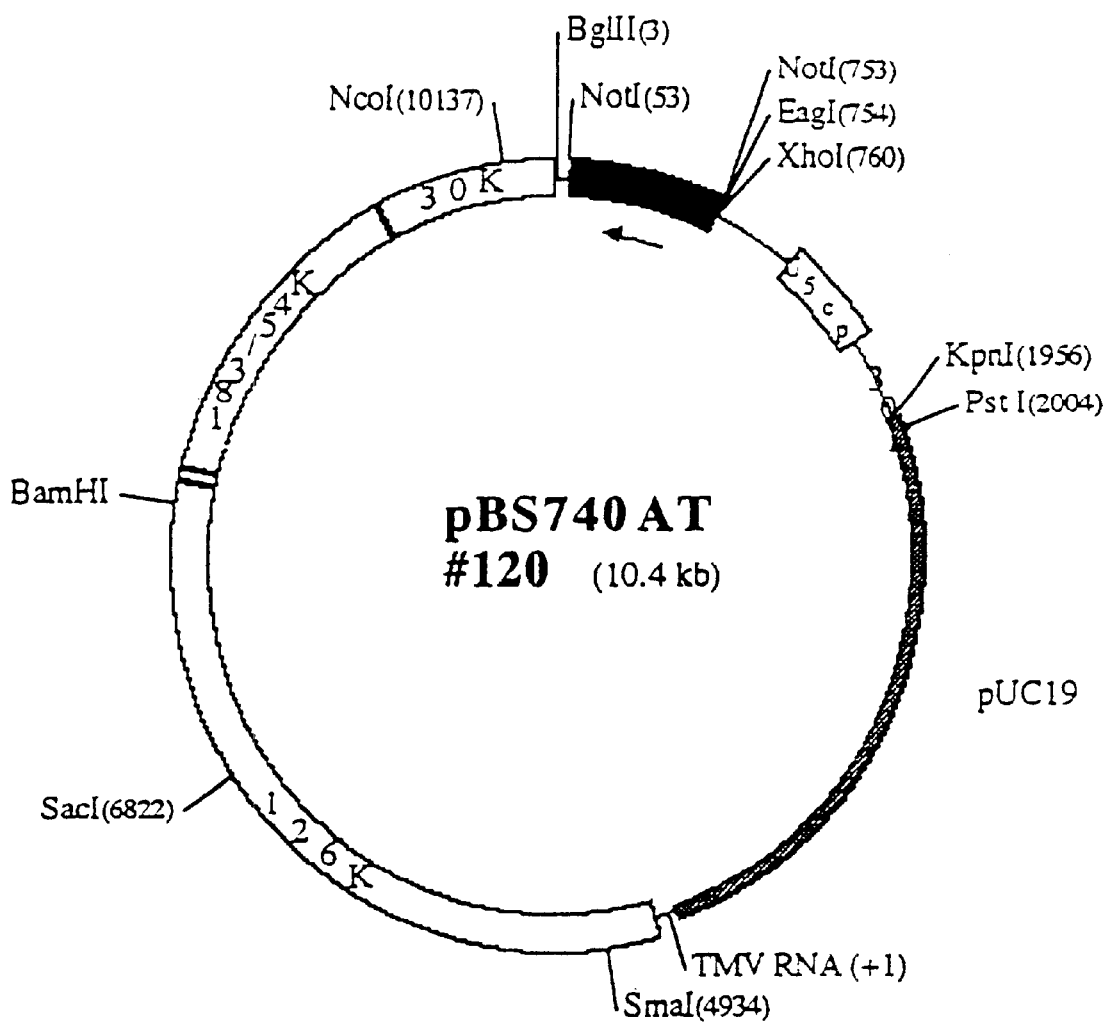
FIG. 6 depicts the plasmid pBS #740 AT #120 (ATCC No.: PTA-325).

One to two weeks after inoculation, transfected *Nicotiana benthamiana* plants were visually monitored for changes in growth rates, morphology, and color. Plants transfected with 740 AT #120 (ATCC No: PTA-325, deposit date Jul. 1999) (FIG. 6) were severely stunted. Plasmid 740 AT #120 contains the TMV-U1 126-, 183-, and 30-kDa ORFs, the TMV-U5 coat protein gene (U5 cp), the T7 promoter, an *Arabidopsis thaliana* CD4-13 NotI fragment, and part of the pUC 19 plasmid. The TMV-U1 subgenomic promoter located within the minus strand of the 30-kDa ORF controls the synthesis of the CD4-13 antisense subgenomic RNA.

DNA Sequencing and Computer Analysis.

A 782 bp NotI fragment of 740 AT #120 containing the ADP-ribosylation factor (ARF) cDNA was characterized. DNA sequence of NotI fragment of 740 AT #120 (774 base pairs) is as follows: 5'-CCGAAACATTCTTCGTAGTGAAGCAAAATGGGGT TGAGTTTCGCCAAGCTGT TTAGCAGGCTTTTTGC-CAAGAAGGAGATGCGAATTCTGATGGT-TGGTCTTGA TGCTGCTGGTAAGACCACAATCTTG-TACAAGCTCAAGCTCGGAGAGATTGT CACCACCATCCCTACTATTGGTTTCAAT-GTGGAAACTGTGGAATACAAGAAC ATT-AGTTTCACCGTGTGGGATGTCGGGGGT-CAGGACAAGATCCGTCCTTGT GAGACACTACTTCCAGAACACTCAAG-GTCTAATCTTTGTTGTTGATAGCAAT GACAGAGA-CAGAGTTGTTGAGGCTCGAGATGAACTC-CACAGGATGCTGAAT GAGGACGAGCTGCGTGATGCTGTGT-TGCTTGTGTTTGCCAACAAGCAAGATC TTCCAAAT-GCTATGAACGCTGCTGAAATCACA-GATAAGCTTGGCCTTCACTC CCTCCGTCAGCGTCATTGGTATATCCA-GAGCACATGTGCCACTTCAGGTGAA GGGCTTTAT-GAAGGTCTGGACTGGCTCTCCAACAA-CATCGCTGGCAAGGCA TGATGAGGGAGAAATTGCGTTGCATC-GAGATGATTCTGTCTGCTGTGTTGGG ATCTCTCTCT-GTCTTGATGCAAGAGAGATTATAAATAT-TATCTGAACCTTTTT GCTTTTTTGGGTATGTGAATGTTTCT-TATTGTGCAAGTAGATGGTCTTGTACC TAAAAATT-TACTAGAAGAACCCTTTTAAATAGCTTT CGTGTATTGT-3' (SEQ ID NO: 20).

The nucleotide sequencing of 740 AT #120 was carried out by dideoxy termination using double stranded templates (Sanger et al. 1977). Nucleotide sequence analysis and amino acid sequence comparisons were performed using DNA Strider, PCGENE and NCBI Blast programs. 740 AT #120 contained an open reading frame (ORF) in the antisense orientation that encodes a protein of 181 amino acids with an apparent molecular weight of 20,579 Daltons. FIG. 7 shows a nucleotide sequence comparison of *A. thalana* 740 AT #120 and *A. thaliana* est AA042085, SEQ ID NO: 21 and SEQ ID NO:22. The nucleotide sequence from 740 AT #120 compared with a rice (Oryza sativa) ADP ribosylation factor AF012896, SEQ ID NOs: 22 and 23 (FIG. 8); which shows 82% (456/550) positives and identities. The nucleotide sequence from 740 AT #120 exhibits a high degree of homology (81–84% identity and positive) to rice, barley, carrot, corn and *A. thaliana* DNA encoding ARFs (Table 1). The amino acid sequence derived from 740 AT #120 exhibits an even higher degree of homology (96–98% identity and 97–98% positive) to ARFs from rice, carrot, corn and *A. thaliana*. (Table 2).

The protein encoded by 740 AT #120, 120P, contained three conserved domains: the phosphate binding loop motif, GLDAAGKT, SEQ ID NO:25 (consensus GXXXXGKS/T); the G' motif, DVGGQ, SEQ ID NO:25 (consensus DXXGQ), a sequence which interacts with the gamma-phosphate of GTP; and the G motif NKQD, (consensus NKXD), which is specific for guanidinyl binding. The 120P contains a putative glycine-myristoylation site at position 2, a potential N-glycosylation site (NXS) at position 60, and several putative serine/threonine phosphorylations sites.

TABLE 1

740 AT #120 Nucleotide sequence comparison

| | Score | Expect | Identities | Positives |
|---|---|---|---|---|
| barley E10542 | 540.8 bits (1957) | 1.4e-157 | 461/548 (84%) | 461/548 (84%) |
| A. thaliana M95166 | 538.5 bits (1949) | 7.4e-157 | 461/550 (83%) | 461/550 (83%) |
| rice AF012896 | 537.7 bits (1946) | 1.3e-156 | 462/553 (83%) | 462/553 (83%) |
| carrot D45420 | 531.4 bits (1923) | 9.8e-155 | 471/579 (81%) | 471/579 (81%) |
| com X80042 | 512.3 bits (1854) | 6.8e-149 | 450/549 (81%) | 450/549 (81%) |

TABLE 2

Amino acid sequence comparison of 740 AT #120 with ARFs from other organisms.

| | Score | Expect | Identities | Positives |
|---|---|---|---|---|
| A. thaliana ARF1 g543841 | 365 bits (928) | e-101 | 179/181 (98%) | 179/181 (98%) |
| rice g1703380 | 363 bits (921) | e-100 | 177/181 (97%) | 179/181 (98%) |
| corn g1351974 | 356 bits (905) | 3e-98 | 174/181 (96%) | 179/181 (98%) |
| carrot g1703375 | 362 bits (919) | e-100 | 177/181 (97%) | 178/181 (97%) |

Example 11

Isolation of an *Arabidopsis thaliana* ARF Genomic Clone

A genomic clone encoding *A. thaliana* ARF can be isolated by probing filters containing *A. thaliana* BAC clones using a $^{32}$P labeled 740 AT #120 NotI insert. Other members of the *A. thaliana* ARF multigene family have been identified using programs of the University of Wisconsin Genetic Computer Group. The BAC clone T08I13 located on chromosome II has a high degree of homology to 740 AT #120 (78% to 86% identity).

Example 12

Construction of a *Nicotiana benthamiana* cDNA Library.

Vegetative *N. benthamiana* plants were harvested 3.3 weeks after sowing and sliced up into three groups of tissue: leaves, stems and roots. Each group of tissue was flash frozen in liquid nitrogen and total RNA was isolated from each group separately using the following hot borate method (Larry Smart and Thea Wilkins, 1995). Frozen tissue was ground to a fine powder with a pre-chilled mortar and pestle, and then further homogenized in pre-chilled glass tissue grinder. Immediately thereafter, 2.5 ml/g tissue hot (~82° C.) XT Buffer (0.2 M borate decahydrate, 30 mM EGTA, 1% (w/v) SDS. Adjusted pH to 9.0 with 5 N NaOH, treated with 0.1% DEPC and autoclaved. Before use, added 1% deoxycholate (sodium salt), 10 mM dithiothreitol, 15 Nonidet P-40 (NP-40) and 2% (w/v) polyvinylpyrrilidone, MW 40,000 (PVP-40)) was added to the ground tissue. The tissue was homogenized 1–2 minutes and quickly decanted to a pre-chilled Oak Ridge centrifuge tube containing 105 μl of 20 mg/ml proteinase K in DEPC treated water. The tissue grinder was rinsed with an additional 1 ml hot XT Buffer per g tissue, which was then added to rest of the homogenate. The homogenate was incubated at 42° C. at 100 rpm for 1.5 h. 2 M KCl was added to the homogenate to a final concentration of 160 mM, and the mixture was incubated on ice for 1 h to precipitate out proteins. The homogenate was centrifuged at 12,000×g for 20 min at 4° C., and the supernatant was filtered through sterile miracloth into a clean 50 ml Oak Ridge centrifuge tube. 8 M LiCl was added to a final concentration of 2 M LiCl and incubated on ice overnight. Precipitated RNA was collected by centrifugation at 12,000×g for 20 min at 4° C. The pellet was washed three times in 3–5 ml 4° C. 2 M LiCl. Each time the pellet was resuspended with a glass rod and then spun at 12,000×g for 20 min at 4° C. The RNA pellet was suspended in 2 ml 10 mM Tris-HCl (pH 7.5), and purified from insoluble cellular components by spinning at 12,000×g for 20 min at 4° C. The RNA containing supernatant was transferred to a 15 ml Corex tube and precipitated overnight at −20° C. with 2.5 volumes of 100% ethanol. The RNA was pelleted by centrifugation at 9,800×g for 30 min at 4° C. The RNA pellet was washed in 1–2 ml cold 70° C. ethanol and centrifuged at 9,800×g for 5 min at 4° C. Residual ethanol was removed from the RNA pellet under vacuum, and the RNA was resuspended in 200 μl DEPC treated dd-water and transferred to a 1.5 ml microfuge tube. The Corex tube was rinsed in 100 μl DEPC-treated dd-water, which was then added to the rest of the RNA. The RNA was then precipitated with 1/10 volume of 3 M sodium acetate, pH 6.0 and 2.5 volumes of cold 100% ethanol at −20° C. for 1–2 h. The tube was centrifuged for 20 min at 16,000×g, and the RNA pellet washed with cold 70% ethanol, and centrifuged for 5 min at 16,000×g. After drying the pellet under vacuum, the RNA was resuspended in DEPC-treated water. This is the total RNA.

Messenger RNA was purified from total RNA using an Poly(A)Pure kit (Ambion, Austin Tex.), following the manufacturer's instructions. A reverse transcription reaction was used to synthesize cDNA from the mRNA template, using the Stratagene kit. The cDNA was subcloned into the bacteriophage at EcoRI/XhoI by ligating to arms using the Gigapack III Gold kit (Stratagene, La Jolla, Calif.), following the manufacturer's instructions.

Example 13

Figure 9:
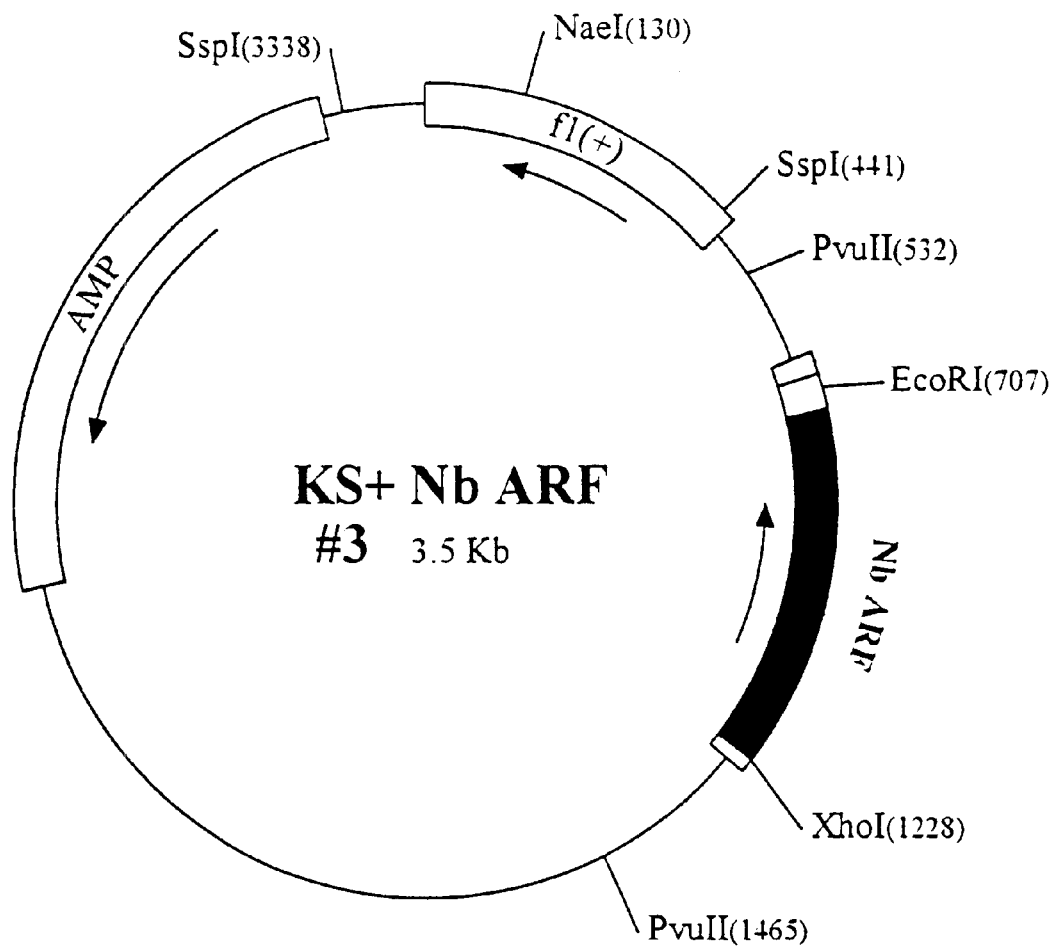
FIG. 9 shows the KS+Nb ARF #3 plasmid (ATCC No.: PTA-324) map.

Isolation and Characterization of a cDNA Encoding *Nicotiana benthamiana* ADP-ribosylation Factor A 488 bp cDNA from *N. benthamiana* stem cDNA library was isolated by polymerase chain reaction (PCR) using the following oligonucleotides: ATARFK15, 5' AAG AAG GAG ATG CGA ATT CTG ATG GT 3' (upstream)(SEQ ID NO:27), ATARFN176, 5' ATG TTG TTG GAG AGC CAG TCC AGA CC 3' (downstream)(SEQ ID NO: 28). The vent polymerase in the reaction was inactivated using phenol/chloroform, and the PCR product was directly cloned into the HincII site in Bluescript KS+ (Strategene). The plasmid map of KS+ Nb ARF #3, which contains the *N. benthamiaca* ARF ORF in pBluescript KS+ is shown in FIG. 9. The nucleotide sequence of *N. benthamiana* KS+Nb ARF#3 (ATCC No: PTA-324, deposit date: Jul. 12, 1999) which contains partial ADP-ribosylation factor ORF, was determined by dideoxynucleotide sequencing. The nucleotide sequence from KS+ Nb ARF#3, SEQ ID NO: 29, had a strong similarity to other plant ADP-ribosylation factor sequences (82 to 87% identity at the nucleotide level). The nucleotide sequence comparison of *N. benthamiana* KS+Nb ARF#3 and *A. thaliana* 740 AT #120 is shown in FIG. 10 and SEQ ID NOS:26 and 27.

A full-length cDNA encoding ARF is isolated by screening the *N. benthamiana* cDNA library by colony hybridization using a $^{32}$P-labeled *N. benthamiana* KS+/Nb ARF #3 probe. Hybridization is carried out at 42° C. for 48 hours in 50% formamide, 5×SSC, 0.02 M phosphate buffer, 5×Denhart's solution, and 0.1 mg/ml sheared calf thymus DNA. Filters are washed at 65° C. in 0.1×SSC, 0.1% SDS prior to autoradiography.

Example 14

Rapid Isolation of cDNAs Encoding Rice, Barley, Corn, Soybean, and other ADP-ribosylation Factor Libraries containing full-length cDNAs from rice, barley, corn, soybean and other important crops are obtained from public and private sources or can be prepared from plant mRNAs. The cDNAs are inserted in viral vectors or in small subcloning vectors such as pBluescript (Strategene), pUC18, M13, or pBR322. Transformed bacteria (*E. coli*) are then plated on large petri plates or bioassay plates containing the appropriate media and antibiotic. Individual clones are selected using a robotic colony picker and arrayed into 96 well microtiter plates. The cultures are incubated at 37° C. until the transformed cells reach log phase. Aliquots are removed to prepare glycerol stocks for long term storage at −80° C. The remainder of the culture is used to inoculate an additional 96 well microtiter plate containing selective media and grown overnight. DNAs are isolated from the cultures and stored at −20° C. Using a robotic unit such as the Qbot (Genetix), the *E. coli* transformants or DNAs are rearrayed at high density on nylon filters or glass slides. Full-length cDNAs encoding ARFs from rice, barley, corn, soybean and other important crops are isolated by screening the various filters of slides by hybridization using a $^{32}$P-labeled or fluorescent *N. benthamiana* KS+/Nb ARF #3 probe, or $^{32}$P-labeled Arabidopsis 740 AT #120 NotI insert.

Example 15

Rapid Isolation of Genomic Clones Encoding ADP Ribosylation Factor from Rice, Barley, Corn, Soybean, and other Plant Genomic libraries containing sequences from rice, barley, corn, soybean and other important crops are obtained from public and private sources, or are prepared from plant genomic DNAs. BAC clones containing entire plant genomes have been constructed and organized in minimal overlapping order. Individual BACs are sheared to 500–1000 bp fragments and directly cloned into viral vectors. Approximate 200–500 clones that completely cover an entire BAC will form a BAC viral vector sublibrary. These libraries can be stored as bacterial glycerol stocks at −80C and as DNA at −20C. Genomic clones are identified by first probing filters of BACs with a $^{32}$P-labeled or fluorescent *N. benthamiana* KS+/Nb ARF #3 probe, or $^{32}$P-labeled Arabidopsis 740 AT #120 NotI insert. BACs that hybridize to the probe are selected and their corresponding BAC viral vector sublibrary is used to produce infectious RNA. Plants that are transfected with the BAC sublibrary are screened for loss of function (for example, stunted plants). The inserts from these clones or their corresponding plasmid DNAs are characterized by dideoxy sequencing. This provides a rapid method to obtain the genomic sequence for the plant ARFs.

Example 16

Identification of Nucleotide Sequences Involved in the Regulation of Plant Development by Cytoplasmic Inhibition of Gene Expression using Viral Derived RNA (G-protein coupled receptor)

This example again demonstrates that an episomal RNA viral vector can be used to deliberately manipulate a signal transduction pathway in plants. In addition, our results suggest that the Arabidopsis antisense transcript can turn off the expression of the *N. benthamiana* gene.

Figure 11:
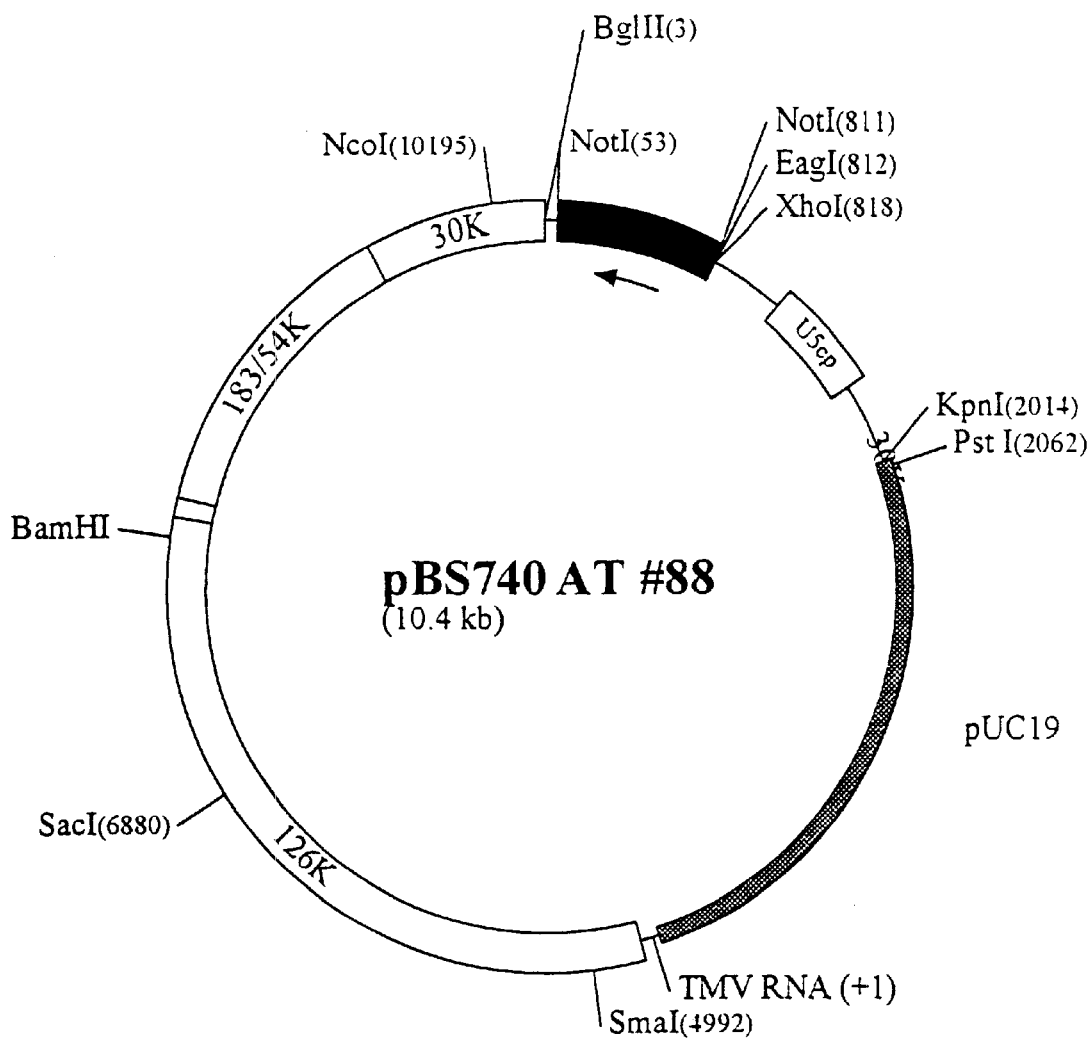
FIG. 11 shows the plasmid pBS #740 AT #88 (ATCC No.: PTA-331).

A partial *Arabidopsis thaliana* cDNA library was placed under the transcriptional control of a tobamovirus subgenomic promoter in a RNA viral vector. (see EXAMPLE 9). Colonies from transformed *E. coli* were automatically picked using a Flexys robot and transferred to a 96 well flat bottom block containing terrific broth (TB) Amp 50 ug/ml. Approximately 2000 plasmid DNAs were isolated from overnight cultures using a BioRobot and infectious RNAs from 430 independent clones were directly applied to plants. One to two weeks after inoculation, transfected *Nicotiana benthamiana* plants were visually monitored for changes in growth rates, morphology, and color. One set of plants transfected with 740 AT #88 (ATCC No: PTA-331, deposit date: Jul. 12, 1999) (FIG. 11) developed a white phenotype on the infected leaf tissue. DNA sequence analysis revealed that this clone contained an Arabidopsis G-protein coupled receptor open reading frame (ORF) in the antisense orientation.

DNA Sequencing and Computer Analysis.

A 750 bp NotI fragment of 740 AT #88 containing the G-protein coupled receptor cDNA was characterized. DNA sequence of NotI fragment of 740 AT #88 (750 bp) is as follows:
5'-TTTCGATCTAAGGTTCGTGATCTCCTTCTTCTCTA CGAAGTTTACACTTTTTC TTCAAAGGAAACAAT-GAGCCAGTACAATCAACCTCCCGTTGGT-GTTCCTCCT CCTCAAGGTTATCCACCGGAGG-GATATCCAAAAGATGCTTATCCACCACAA GGATATCCTCCTCAGGGATATCCTCAG-CAAGGCTATCCACCTCAGGGATATC CTCAACAAG-GTTATCCTCAGCAAGGATATCCTCCAC-CGTACGCGCCTCAATA TCCTCCACCACCGCAAGCATCAGCAA-CAACAGAGCAAGTCCTGGCTTTCTA GAAGGAT-GTCTTGCTGCTGTGTTGTTGCT-GTCTCTTGGATGCTTGCTTCTG ATTGGAGTCTCTCTCTCTGCAT-AAAGCTTCGGGATTTATTTGTAAGAGGG TTTTTGGGTTAAACAAAAACCTTAAT-TGATTTGTGGGCATTAAAAATGAAT CTCTCGAT-GATTCTCTTCGTTTATGTGGTAATGT-TCTTCGGTTATAACATTTA ACATTGCTATCGACGTTCTGCCTAGTTG-GATTTGATTATTGGGAATGTAAAT TGGTTGGGAA-GACACCGGGCCGTTAATGACAGAAC-CCGAACTGAGATGGAG TATGATCTGAAATATTTAAAACAATC-CTCGCGACATAGCCTCCAATCTCATC GTAAATAT-TCTTTTTAAACTATTCCCAATCT-TAACTTTTATAGTCTGGTCGAC TGACCACTACTCTTTTTCCTT-3' (SEQ ID NO: 30) The nucleotide sequencing of 740 AT #88 was carried out by dideoxy termination using double stranded templates (Sanger et al., *Proc. Natl. Acad. Sci.* USA 74(12):5463–5467 (1977)). Nucleotide sequence analysis and amino acid sequence comparisons were performed using DNA Strider, PCGENE and NCBI Blast programs.

Example 17

Figure 12:
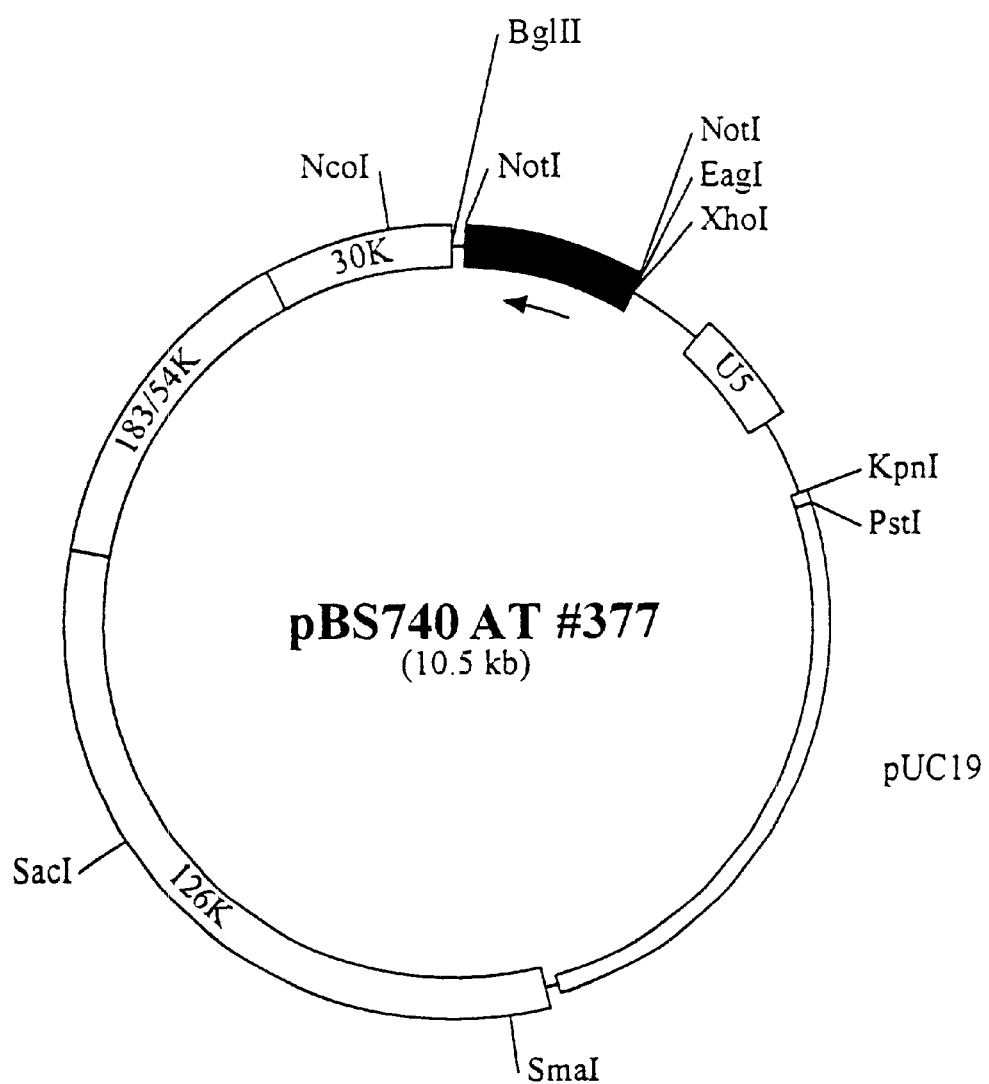
FIG. 12 shows the plasmid pBS #377 (ATCC No.: PTA-334).

Identification of Nucleotide Sequences Containing an Arabidopsis S18 Ribosomal Protein Open Reading Frame One to two weeks after inoculation, transfected *Nicotiana benthamiana* plants were visually monitored for changes in growth rates, morphology, and color. one set of plants transfected with 740 AT #377 (FIG. 12) were severely stunted. DNA sequence analysis (FIG. 13, SEQ ID NO: 31) revealed that this clone contained an Arabidopsis S18 ribosomal protein open reading frame (ORF) in the antisense orientation.

Example 18

Figure 14:
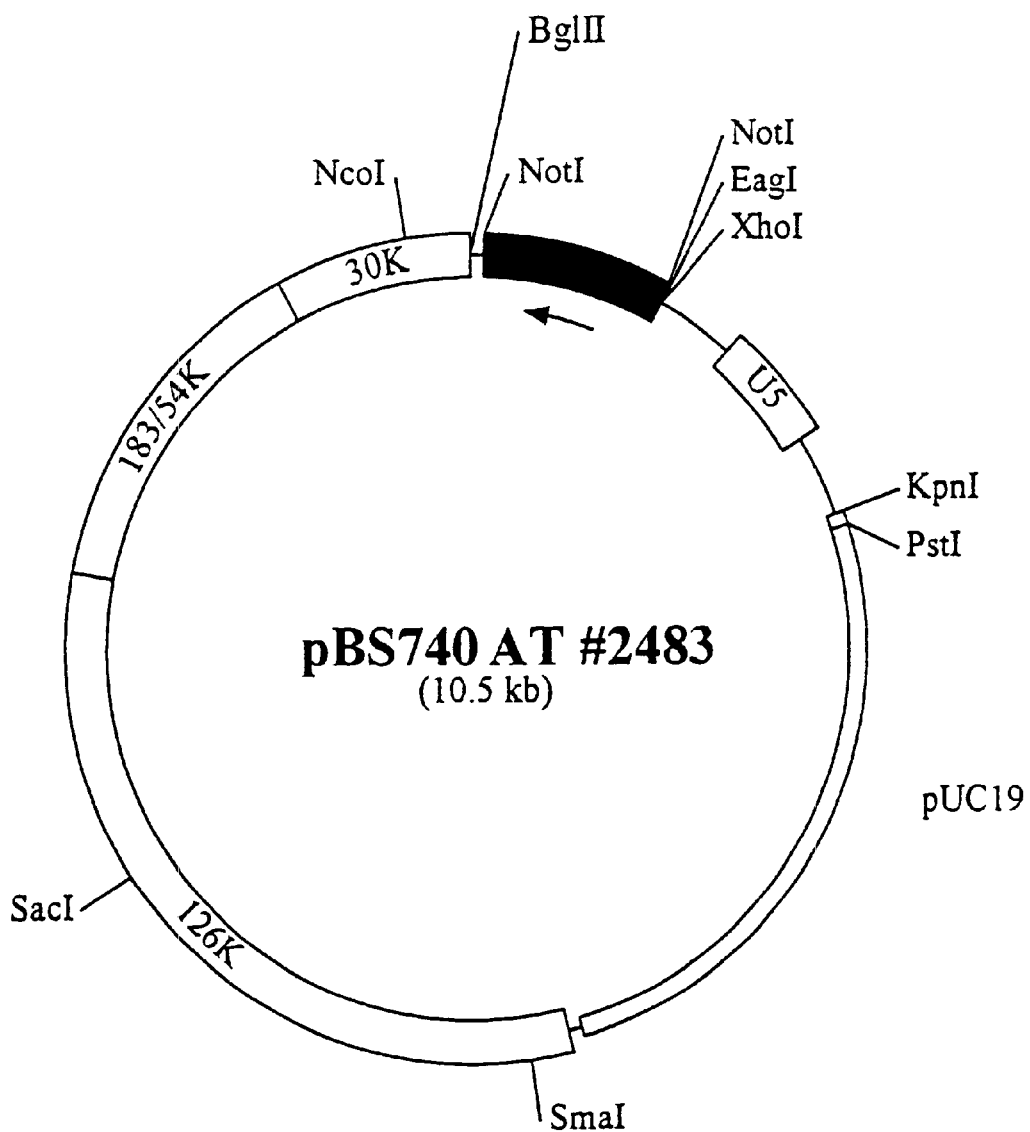
FIG. 14 shows the plasmid pBS #2483 (ATCC No.: PTA-328).

Identification of L19 Ribosomal Protein Gene Involved in the Regulation of Plant Growth by Cytoplasmic Inhibition of Gene Expression using Viral Derived RNA One to two weeks after inoculation, transfected *Nicotiana benthamiana* plants were visually monitored for changes in growth rates, morphology, and color. One set of plants transfected with 740 AT #2483 (FIG. 14) were severely stunted. DNA sequence analysis (FIG. 15, SEQ ID NO: 32) revealed that this clone contained an Arabidopsis L19 ribosomal protein open reading frame (ORF) in the antisense orientation. The 740 AT #2483 nucleotide sequence exhibited a high degree of homology (77–78% identities and positives) to plant, L19 ribosomal proteins genes (Table 3).

TABLE 3

| 740 AT #2483 Nucleotide sequence comparison | | | | |
|---|---|---|---|---|
| Clone | Score | pValue | Identities | Positives |
| A. thaliana AF075597 | 389 (107.5 bits) | 2.60E-38 | 101/130 (77%) | 101/130 (77%) |
| Rice mRNA for ribosomal protein L19 D21304 | 198 (54.7 bits) | 2.20E-10 | 50/64 (78%) | 50/64 (78%) |
| N. tabacum L19 mRNA Z31720 | 194 (53.6 bits) | 3.50E-05 | 50/64 (78%) | 50/64 (78%) |

Example 19

Novel Requirements for Production of Infectious Viral Vector in Vitro Derived RNA Transcripts This example demonstrates the production of highly infectious viral vector transcripts containing 5' nucleotides with reference to the virus vector.

Construction of a library of subgenomic cDNA clones of TMV and BMV has been described in Dawson et al., *Proc. Natl. Acad. Sci.* USA 83:1832–1836 (1986) and Ahlquist et al., *Proc. Natl. Acad. Sci.* USA 81:7066–7070 (1984). Nucleotides were added between the transcriptional start site of the promoter for in vitro transcription, in this case T7, and the start of the cDNA of TMV in order to maximize transcription product yield and possibly obviate the need to cap virus transcripts to insure infectivity. The relevant sequence is the T7 promoter . . . TATAG^TATTTT . . . (SEQ ID NO: 33) where the ^indicates the base preceding is the start site for transcription and the bold letter is the first base of the TMV cDNA. Three approaches were taken: 1) addition of G, GG or GGG between the start site of transcription and the TMV cDNA ( . . . TATAGGTATTT, (SEQ ID NO: 34), . . . and associated sequences); 2) addition of G and a random base (GN or N2) or a G and two random bases (GNN or N3) between the start site of transcription and the TMV cDNA ( . . . TATAGNTATTT (SEQ ID NO: 35), . . . and associated sequences), and the addition of a GT and a single random base between the start site of transcription and the TMV cDNA ( . . . TATAGTNGTATTT (SEQ ID NO: 36), . . . and associated sequences). The use of random bases was based on the hypothesis that a particular base may be best suited for an additional nucleotide attached to the cDNA, since it will be complementary to the normal non-templated base incorporated at the 3'-end of the TMV (−) strand RNA. This allows for more ready mis-initiation and restoration of wild type sequence. The GTN would allow the mimicking of two potential sites for initiation, the added and the native sequence, and facilitate more ready mis-initiation of transcription in vivo to restore the native TMV cDNA sequence. Approaches included cloning GFP expressing TMV vector sequences into vectors containing extra G, GG or GGG bases using standard molecular biology techniques. Likewise, full length PCR of TMV expression clone 1056 was done to add N2, N3 and GTN bases between the T7 promoter and the TMV cDNA. Subsequently, these PCR products were cloned into pUC based vectors. Capped and uncapped transcripts were made in vitro and inoculated to tobacco protoplasts or *Nicotiana benthamiana* plants, wild type and 30k expressing transgenics. The results are that an extra G, . . . TATAGGTATTTT (SEQ ID NO: 37), . . . , or a GTC, . . . TATAGTCGTATTTT (SEQ ID NO: 38), . . . , were found to be well tolerated as additional 5' nucleotides on the 5' of TMV vector RNA transcripts and were quite infectious on both plant types and protoplasts as capped or non-capped transcripts.

Other sequences may be screened to find other options. Clearly, infectious transcripts may be derived with extra 5' nucleotides.

Other derivatives based on the putative mechanistic function of the GTN strategy that yielded the GTC functional vector are to use multiple GTN motifs preceeding the 5' most nt of the virus cDNA or the duplication of larger regions of the 5'-end of the TMV genome. For example: TATA^GTNGTNGTATT, (SEQ ID NO: 39), . . . or TAT-A^GTNGTNGTNGTNGTATT (SEQ ID NO: 40), . . . or TATA^GTATTTGTATTT (SEQ ID NO: 41), . . . In this manner the replication mediated repair mechanism may be potentiated by the use of multiple recognition sequences at the 5'-end of transcribed RNA. The replicated progeny may exhibit the results of reversion events that would yield the wild type virus 5' virus sequence, but may include portions or entire sets of introduced additional base sequences. This strategy can be applied to a range of RNA viruses or RNA viral vectors of various genetic arrangements derived from wild type virus genome. This would require the use of sequences particular to that of the virus used as a vector.

Example 20

Infectivity of Uncaped Transcripts.

Two TMV-based virus expression vectors were initially used in these studies pBTI 1056 which contains the T7 promoter followed directly by the virus cDNA sequence ( . . . TATAGTATT . . . ), and pBTI SBS60-29 which contains the T7 promoter (underlined) followed by an extra guanine residue then the virus cDNA sequence ( . . . TATAGGTATT . . . ). Both expression vectors express the cycle 3 shuffled green fluorescent protein (GFPc3) in localized infection sites and systemically infected tissue of infected plants. Transcriptions of each plasmid were carried out in the absence of cap analogue (uncapped) or in the presence of 8-fold greater concentration of RNA cap analogue than rGTP (capped). Transcriptions were mixed with abrasive and inoculated on expanded older leaves of a wild type *Nicotiana benthamiana* (Nb) plant and a Nb plant expressing aTMV U1 30k movement protein transgene (Nb 30K). Four days post inoculation (dpi), long wave UV light was used to judge the number of infection sites on the inoculated leaves of the plants. Systemic, noninoculated tissues, were monitored from 4 dpi on for appearance of systemic infection indicating vascular movement of the inoculated virus. Table 4 shows data from one representative experiment.

TABLE 4

| Construct | Local infection sites | | Systemic Infection | |
| --- | --- | --- | --- | --- |
| | Nb | Nb 30K | Nb | Nb 30K |
| pBTI1056 | | | | |
| Capped | 5 | 6 | yes | yes |
| Uncapped | 0 | 5 | no | yes |
| PBTI SBS60-29 | | | | |
| Capped | 6 | 6 | yes | yes |
| Uncapped | 1 | 5 | yes | yes |

*Nicotiana tabacum* protoplasts were infected with either capped or uncapped transcriptions (as described above) of pBTI SBS60 which contains the T7 promoter followed directly by the virus cDNA sequence (TATAGTATT . . . ). This expression vector also expresses the GFPc3 gene in infected cells and tissues. *Nicotiana tabacum* protoplasts were transfected with 1 mcl of each transcriptions. Approximately 36 hours post infection transfected protoplasts were viewed under UV illumination and cells showing GFPc3 expression. Approximately 80% cells transfected with the capped PBTI SBS60 transcripts showed GFP expression while 5% of cells transfected with uncapped transcripts showed GFP expression. These experiments were repeated with higher amounts of uncapped inoculum. In this case a higher proportion of cells, >30% were found to be infected at this time with uncapped transcripts, where >90% of cells infected with greater amounts of capped transcripts were scored infected.

These results indicate that, contrary to the practiced art in scientific literature and in issued patents (Ahlquist et al., U.S. Pat. No. 5,466,788), uncapped transcripts for virus expression vectors are infective on both plants and in plant cells, however with much lower specific infectivity. Therefore, capping is not a prerequisite for establishing an infection of a virus expression vector in plants; capping just increases the efficiency of infection. This reduced efficiency can be overcome, to some extent, by providing excess in vitro transcription product in an infection reaction for plants or plant cells.

The expression of the 30K movement protein of TMV in transgenic plants also has the unexpected effect of equalizing the relative specific infectivity of uncapped verses capped transcripts. The mechanism behind this effect is not fully understood, but could arise from the RNA binding activity of the movement protein stabilizing the uncapped transcript in infected cells from prereplication cytosolic degradation.

Extra guanine residues located between the T7 promoter and the first base of a virus cDNA lead to increased amount of RNA transcript as predicted by previous work with phage polymerases. These polymerases tend to initiate more efficiently at . . . TATAGG or . . . TATAGGG than . . . TATAG. This has an indirect effect on the relative infectivity of uncapped transcripts in that greater amounts are synthesized per reaction resulting in enhanced infectivity.

Data Concerning Cap Dependent Transcription of pBTI1056 GTN#28.

TMV-based virus expression vector pBTI 1056 GTN#28 which contains the T7 promoter (underlined) followed GTC bases (bold) then the virus cDNA sequence ( . . . TATAGTCGTATT SEQ ID NO: 42, . . . ). This expression vector expresses the cycle 3 shuffled green fluorescent protein (GFPc3) in localized infection sites and systemically infected tissue of infected plants. This vector was transcribed in vitro in the presence (capped) and absence (uncapped) of cap analogue. Transcriptions were mixed with abrasive and inoculated on expanded older leaves of a wild type Nicotiana benthamiana (Nb) plant and a Nb plant expressing a TMV U1 30k movement protein transgene (Nb 30K). Four days post inoculation (dpi) long wave WV light was used to judge the number of infection sites on the inoculated leaves of the plants. Systemic, non-inoculated tissues, were monitored from 4 dpi on for appearance of systemic infection indicating vascular movement of the inoculated virus. Table 5 shows data from two representative experiments at 11 dpi.

TABLE 5

| Construct | Local infection sites | | Systemic Infection | |
| --- | --- | --- | --- | --- |
| | Nb | Nb 30K | Nb | Nb 30K |
| Experiment 1 pBTI1056 GTN#28 | | | | |
| Capped | 18 | 25 | yes | yes |
| Uncapped | 2 | 4 | yes | yes |
| Experiment 2 pBTI1056 GTN#28 | | | | |
| Capped | 8 | 12 | yes | yes |
| Uncapped | 3 | 7 | yes | yes |

These data further support the claims concerning the utility of uncapped transcripts to initiate infections by plant virus expression vectors and further demonstrates that the introduction of extra, non-viral nucleotides at the 5'-end of in vitro transcripts does not preclude infectivity of uncapped transcripts.

Although the invention has been described with reference to the presently preferred embodiments, it should be understood that various modifications can be made without departing from the spirit of the invention.

What is claimed is:

1. A method of compiling a plant antisense functional gene profile comprising:
   a) preparing a library of DNA or RNA sequences from a donor plant, and constucting recombinant viral nucleic acids obtained from a tobamo virus comprising an unidentified nucleic acid insert obtained from said library in an antsense orientation relative to said DNA or RNA sequence of said donor plant;

b) infecting a plant host with one or more said recombinant viral nucleic acids;

c) transiently expressing said unidentified nucleic acid in the plant host;

d) determining one or more phenotypic or biochemical changes in the plant host, if any;

e) identifying an associated trait where a phenotypic or biochemical change occurs;

f) identifying said recombinant viral nucleic acid that results in said one or more changes in the plant host;

g) identifying a plant host gene, if any, associated with the trait, and h) repeating steps b)–g) until at least one nucleic acid is associated with said trait, whereby an antisense functional gene profile of the plant host or of the donor plant is compiled.

2. A method of compiling a plant functional gene profile, comprising:

a) preparing a library of DNA or RNA sequence from a donor plant, and constructing recombinant viral nucleic acids obtained from a tobamo virus comprising an unidentified nucleic acid insert obtained from said library in either a positive sense or antisense orientation relative to said DNA or RNA sequence of said donor plant;

b) infecting a plant host with one or more said recombinant viral nucleic acids;

c) transiently expressing said unidentified nucleic acid in the plant host;

d) determining one or more phenotypic or biochemical changes in the plant host, if any;

e) identifying an associated trait where a phenotypic or biochemical change occurs;

f) identifying said recombinant viral nucleic acid that results a said one or more changes in the plant host;

g) identifying a plant host gene, if any, associated with the trait; and h) repeating steps b)–g ) until at least one nucleic acid is associated with said trait, whereby a functional gene profile of the plant host or of the plant donor is compiled.

3. A method of compiling a plant antisense functional gene profile comprising:

a) preparing a vector library of DNA or RNA sequences from a donor plant, and constructing recombinant viral nucleic acids obtained from a tobamo virus comprising an unidentified nucleic acid insert obtained from said library;

b) infecting a plant host with one or more said recombinant viral nucleic acids;

c) transiently expressing said recombinant nucleic acid in the plant host;

d) determining one or more changes in phenotypic or biochemical trait in the plant host if any;

e) identifying said recombinant viral nucleic acid that results in said one or more changes in the plant host;

f) determining and selecting the sequence of said nucleic acid insert in said recombinant viral nucleic acid that is in an antisense orientation relative to a donor plant gene or a plant host gene;

g) identifying a plant host gene, if any, associated with the trait; and h) repeating steps b)–g) until at least one donor plant gene or one plant host gene associated with said trait is identified, whereby an antisense functional gene profile of the plant host or of the donor plant is compiled.

4. A method of compiling a plant functional gene profile, comprising:
   a) preparing a library of DNA or RNA sequences from a donor plant, and constructing recombinant viral nucleic acids obtained from a tobamo virus comprising an unidentified nucleic acid insert obtained from said library;
   b) infecting a plant host with one or more said recombinant viral nucleic acids;
   c) transiently expressing said recombinant nucleic acid in the plant host;
   d) determining one or more changes in a phenotypic or biochemical trait in the plant host, if any;
   e) identifying and determining said recombinant viral nucleic acid that results in said one or more changes in the plant host;
   f) identifying a plant host gene, if any, associated with the trait and
   g) repeating steps b)–f) until at least one donor plant gene or one plant host gene associated with said trait is identified, whereby a functional gene profile of the plant host or the plant donor is compiled.

5. The method according to any one of claims 1–4, wherein said changes in said plant host is compared with a plant host that is uninfected.

6. The method according to any one of claims 1–4, wherein said changes occur after infecting said plant host with said one or more recombinant viral nucleic acids.

7. The method according to claim 1, wherein said plant host is Nicotiana.

8. The method according to claim 7, wherein said plant host is *Nicotiana benthamiana* or *Nicotiana cleavlandii.*

9. The method according to claim 1, wherein an antisense RNA is produced in the cytoplasm of said plant host, and said antisense RNA results in a reduced expression of an endogenous gene in said host plant.

10. The method according to claim 1, wherein said recombinant viral nucleic acid further comprises a native plant viral subgenomic promoter and a plant viral coat protein coding sequence.

11. The method according to claim 10, wherein said recombinant viral nucleic acid further comprises a non-native plant viral subgenomic promoter, said native plant viral subgenomic promoter initiates transcription of said plant viral coat protein sequence and said non-native plant viral subgenomic promoter initiates transcription of said nucleic acid sequence.

12. The method according to any one of claim 1–4, wherein said tobamo virus is a tobacco mosaic virus.

13. A method of compiling a plant antsense functional gene profile comprising:
   a) preparing a library of DNA or RNA sequences from a donor plant, and constructing recombinant viral nucleic acids obtained from a tobamo virus comprising an unidentified nucleic acid insert obtained from said library in an antisense orientation relative to said DNA or RNA sequence from said donor plant;
   b) infecting a plant host with one or more sad recombinant viral nucleic acids;
   c) transiently expressing said unidentified nucleic acid in the plant host;
   d) identifying one or more phenotypic or biochemical changes in the plant host, if any;
   e) identifying an associated trait where a phenotypic or biochemical change occurs;
   f) identifying said recombinant viral nucleic acid that results in said one or more changes in the plant host;
   g) repeating steps b)–f) until at least one nucleic acid is associated with said trait, whereby an antisense functional gene profile of the plant host or of the donor plant is compiled.

14. A method of compiling a plant functional gene profile, comprising:
   a) preparing a library of DNA or RNA sequences from a donor plant, and constructing recombinant viral nucleic acids obtained from a tobamo virus comprising an unidentified nucleic acid insert obtained from said library in either a positive sense or antisense orientation relative to said DNA or RNA sequences from said donor plant;
   b) infecting a plant host with one or more said recombinant viral nucleic acids;
   c) transiently expressing said unidentified nucleic acid in the plant host;
   d) determining one or more phenotypic or biochemical changes in the plant host, if any;
   e) identifying an associated trait where a phenotypic or biochemical change occurs;
   f) identifying said recombinant viral nucleic acid trait results in said one or more changes in the plant host;
   g) repeating steps b)–f) until at least one nucleic acid is associated with said trait, whereby a functional gene profile of the plant host or of the plant donor is compiled.

* * * * *

SEQUENCE LISTING

<160> NUMBER OF SEQ ID NOS: 42

<210> SEQ ID NO 1
<211> LENGTH: 26
<212> TYPE: DNA
<213> ORGANISM: Tomato mosaic virus

<400> SEQUENCE: 1
ctcgcaaagt ttcgaaccaa atcctc                                       26

<210> SEQ ID NO 2
<211> LENGTH: 35
<212> TYPE: DNA
<213> ORGANISM: Tomato mosaic virus

<400> SEQUENCE: 2
cggggtacct gggccccaac cggggttcc ggggg                              35

<210> SEQ ID NO 3
<211> LENGTH: 41
<212> TYPE: DNA
<213> ORGANISM: Tomato mosaic virus

<400> SEQUENCE: 3
tcctcgagcc taggctcgca aagtttcgaa ccaaatcctc a                       41

<210> SEQ ID NO 4

-continued

```
<210> SEQ ID NO 4
<211> LENGTH: 35
<212> TYPE: DNA
<213> ORGANISM: Tomato mosaic virus

<400> SEQUENCE: 4
cggggtacct gggccccaac cgggggttcc ggggg                              35

<210> SEQ ID NO 5
<211> LENGTH: 30
<212> TYPE: DNA
<213> ORGANISM: Tomato mosaic virus

<400> SEQUENCE: 5
tgctcgagtg tgttcttcag ttttctgtca                                   30

<210> SEQ ID NO 6
<211> LENGTH: 30
<212> TYPE: DNA
<213> ORGANISM: Tomato mosaic virus

<400> SEQUENCE: 6
aactcgagcg ctttgatttc tccgaagctt                                   30

<210> SEQ ID NO 7
<211> LENGTH: 31
<212> TYPE: DNA
<213> ORGANISM: Ribgrass mosaic virus

<400> SEQUENCE: 7
tactcgaggt tcataagacc gcggtaggcg g                                 31

<210> SEQ ID NO 8
<211> LENGTH: 36
<212> TYPE: DNA
<213> ORGANISM: Ribgrass mosaic virus

<400> SEQUENCE: 8
cggggtacct gggcccctac ccggggttta gggagg                            36

<210> SEQ ID NO 9
<211> LENGTH: 1543
<212> TYPE: DNA
<213> ORGANISM: Ribgrass mosaic virus

<400> SEQUENCE: 9
ctcgaggttc ataagaccgc ggtaggcgga gcgtttgttt actgtagtat aattaaatat   60
ttgtcagata aaaggttgtt taaagatttg tttttttgttt gactgagtcg ataatgtctt  120
acgagcctaa agttagtgac ttccttgctc ttacgaaaaa ggaggaaatt ttacccaagg  180
ctttgacgag attaaagact gtctctatta gtactaagga tgttatatct gttaaggagt  240
ctgagtccct gtgtgatatt gatttgttag tgaatgtgcc attagataag tataggtatg  300
tgggtgtttt gggtgttgtt ttcaccggtg aatggctggt accggatttc gttaaaggtg  360
gggtaacagt gagcgtgatt gacaaacggc ttgaaaattc cagagagtgc ataattggta  420
cgtaccgagc tgctgtaaag gacagaaggt tccagttcaa gctggttcca aattacttcg  480
tatccattgc ggatgccaag cgaaaaccgt ggcaggttca tgtgcgaatt caaaatctga  540
agatcgaagc tggatggcaa cctctagctc tagaggtggt ttctgttgcc atggttacta  600
ataacgtggt tgttaaaggt ttgagggaaa aggtcatcgc agtgaatgat ccgaacgtcg  660
aaggtttcga aggtgtggtt gacgatttcg tcgattcggt tgctgcattc aaggcgattg  720
```

-continued

```
acagtttccg aaagaaaaag aaaaagattg gaggaaggga tgtaaataat aataagtata      780
gatatagacc ggagagatac gccggtcctg attcgttaca atataaagaa gaaaatggtt      840
tacaacatca cgagctcgaa tcagtaccag tatttcgcag cgatgtgggc agagcccaca      900
gcgatgctta accagtgcgt gtctgcgttg tcgcaatcgt atcaaactca ggcggcaaga      960
gatactgtta gacagcagtt ctctaacctt ctgagtgcga ttgtgacacc gaaccagcgg     1020
tttccagaaa caggataccg ggtgtatatt aattcagcag ttctaaaacc gttgtacgag     1080
tctctcatga agtcctttga tactagaaat aggatcattg aaactgaaga agagtcgcgt     1140
ccatcggctt ccgaagtatc taatgcaaca caacgtgttg atgatgcgac cgtggccatc     1200
aggagtcaaa ttcagctttt gctgaacgag ctctccaacg acatggtct gatgaacagg      1260 gcagagttcg aggttttatt accttgggct actgcgccag ctacataggc gtggtgcaca     1320
cgatagtgca tagtgttttt ctctccactt aaatcgaaga gatatactta cggtgtaatt     1380
ccgcaagggt ggcgtaaacc aaattacgca atgttttagg ttccatttaa atcgaaacct     1440
gttatttcct ggatcacctg ttaacgtacg cgtggcgtat attacagtgg gaataactaa     1500
aagtgagagg ttcgaatcct ccctaacccc gggtaggggc cca                      1543

<210> SEQ ID NO 10
<211> LENGTH: 55
<212> TYPE: DNA
<213> ORGANISM: Ribgrass mosaic virus

<400> SEQUENCE: 10
gatggcgcct aatacgact cactatagtt ttattttgt tgcaacaaca acaac              55

<210> SEQ ID NO 11
<211> LENGTH: 30
<212> TYPE: DNA
<213> ORGANISM: Ribgrass mosaic virus

<400> SEQUENCE: 11
cttgtgccct tcatgacgag ctatatcacg                                        30

<210> SEQ ID NO 12
<211> LENGTH: 496
<212> TYPE: DNA
<213> ORGANISM: Ribgrass mosaic virus

<400> SEQUENCE: 12
ccttaatacg actcactata gttttatttt tgttgcaaca acaacaacaa attacaataa       60
caacaaaaca aatacaaaca acaacaacat ggcacaattt caacaaacag taaacatgca     120
aacattgcag gctgccgcag ggcgcaacag cctggtgaat gatttagcct cacgacgtgt     180
ttatgacaat gctgtcgagg agctaaatgc acgctcgaga cgccctaagg ttcattactc     240
caaatcagtg tctacggaac agacgctgtt agcttcaaac gcttatccgg agtttgagat     300
ttcctttact catacccaac atgccgtaca ctcccttgcg ggtggcctaa ggactcttga     360
gttagagtat ctcatgatgc aagttccgtt cggttctctg acgtacgaca tcggtggtaa     420 cttttgcagcg cacctttca aaggacgcga ctacgttcac tgctgtatgc caaacttgga     480
tgtacgtgat atagct                                                     496

<210> SEQ ID NO 13
<211> LENGTH: 55
<212> TYPE: DNA
```

-continued

<213> ORGANISM: Ribgrass mosaic virus

<400> SEQUENCE: 13
gatggcgcct taatacgact cactatagtt ttattttttgt tgcaacaaca acaac        55

<210> SEQ ID NO 14
<211> LENGTH: 37
<212> TYPE: DNA
<213> ORGANISM: Ribgrass mosaic virus

<400> SEQUENCE: 14
atcgtttaaa ctgggcccct acccggggtt agggagg        37

<210> SEQ ID NO 15
<211> LENGTH: 497
<212> TYPE: DNA
<213> ORGANISM: Ribgrass mosaic virus

<400> SEQUENCE: 15
ccttaatacg actcactata gtttattttt tgttgcaaca acaacaacaa attacaataa        60
caacaaaaca aatacaaaca acaacaacat ggcacaattt caacaaacag taaacatgca       120
aacattccag gctgccgcag ggcgcaacag cctggtgaat gatttagcct cacgacgtgt       180
ttatgacaat gctgtcgagg agctaaatgc acgctcgaga cgccctaagg ttcattactc       240
caaatcagtg tctacggaac agacgctgtt agcttcaaac gcttatccgg agtttgagat       300
tccttttact catacccaaa catgccgtac actcccttgc gggtggccta aggactcttg       360
agttagagta tctcatgatg caagttccgt tcggttctct gacgtacgac atcggtggta       420
actttgcagc gcacctttc aaaggacgcg actacgttca ctgctgtatg ccaaacttgg        480
atgtacgtga tatagct        497

<210> SEQ ID NO 16
<211> LENGTH: 55
<212> TYPE: DNA
<213> ORGANISM: Ribgrass mosaic virus

<400> SEQUENCE: 16
gatggcgcct taatacgact cactatagtt ttattttttgt tgcaacaaca acaac        55

<210> SEQ ID NO 17
<211> LENGTH: 37
<212> TYPE: DNA
<213> ORGANISM: Ribgrass mosaic virus

<400> SEQUENCE: 17
atcgtttaaa ctgggcccct acccggggtt agggagg        37

<210> SEQ ID NO 18
<211> LENGTH: 14
<212> TYPE: DNA
<213> ORGANISM: Arabidopsis thaliana

<400> SEQUENCE: 18
tcgagcggcc gcat        14

<210> SEQ ID NO 19
<211> LENGTH: 8
<212> TYPE: DNA
<213> ORGANISM: Arabidopsis thaliana

<400> SEQUENCE: 19

```
                                                            gcggccgc                                                                              8

<210> SEQ ID NO 20
<211> LENGTH: 773
<212> TYPE: DNA
<213> ORGANISM: Arabidopsis thaliana

<400> SEQUENCE: 20
ccgaaacatt cttcgtagtg aagcaaaatg gggttgagtt tcgccaagct gtttagcagg      60 cttttttgcca agaaggagat gcgaattctg atggttggtc ttgatgctgc tggtaagacc    120
acaatcttgt acaagctcaa gctcggagag attgtcacca ccatccctac tattggtttc    180
aatgtggaaa ctgtggaata caagaacatt agtttcaccg tgtgggatgt cggggggtcag   240 gacaagatcc gtcccttgtg agacactact tccagaacac tcaaggtcta atctttgttg    300
ttgatagcaa tgacagagac agagttgttg aggctcgaga tgaactccac aggatgctga    360
atgaggacga gctgcgtgat gctgtgttgc ttgtgtttgc caacaagcaa gatcttccaa    420
atgctatgaa cgctgctgaa atcacagata agcttggcct tcactccctc cgtcagcgtc    480
attggtatat ccagagcaca tgtgccactt caggtgaagg ctttatgaa ggtctggact     540 ggctctccaa caacatcgct ggcaaggcat gatgaggag aaattgcgtt gcatcgagat     600
gattctgtct gctgtgttgg gatctctctc tgtcttgatg caagagagat tataaatatt    660
atctgaacct ttttgctttt tgggtatgt gaatgtttct tattgtgcaa gtagatggtc    720
ttgtacctaa aaatttacta gaagaaccct tttaaatagc tttcgtgtat tgt            773

<210> SEQ ID NO 21
<211> LENGTH: 404
<212> TYPE: DNA
<213> ORGANISM: Arabidopsis thaliana

<400> SEQUENCE: 21
tccgaaacat tcttcgtact gaagcaaaat ggggttgagt ttcgccaagc tgtttagcag      60 gcttttttgcc aagaaggaga tgcgaattct gatggttggt cttgatgctg ctggtaagac    120
cacaatcttg tacaagctca agctcggaga gattgtcacc accatccctt actattggtt    180
tcaatgtgga aactgtggaa tacaagaaca ttagtttcac cgtgtggatg tcgggggtca    240
ggacaagatc cgtccgtccc ttgtggagac actacttcca gaacactcaa ggtctaatct    300
ttgttgttga tagcaatgac agagacagag ttgttgaggc tcgagatgaa ctccacagga    360
tgctgaatga ggacgagctg cgtgatgctg tgttgcttgt gttt                      404

<210> SEQ ID NO 22
<211> LENGTH: 400
<212> TYPE: DNA
<213> ORGANISM: Arabidopsis thaliana
<220> FEATURE:
<221> NAME/KEY: misc_feature
<222> LOCATION: (1)...(400)
<223> OTHER INFORMATION: n= a, t, c or g

<400> SEQUENCE: 22
tccgaaacat tcttcgtagt gaagcaaaat ggggttgagt ttcgccaagc tgtttagcag      60 gcttttttgcc aagaaggaga tgcgaattct gatggttggt cttgatgctg ctggtaagac    120
cacaatgttg tacaagctca agctcggaga gattgtcacc accatccctu ctattggttt    180
caatgtggaa actgtggaat acaagaacat tagtttcacc gtgtgggatg tcgggggtca    240
```

-continued

```
ggacaagatc cgtcccttgt ggagacacta cttccagaac actcaaggtc taatctttgt    300
tgttgatagc aatgacagag acagagttgt tgaggctcga gatgaactcc acaggatgct    360
gnatgagnac gagctgcgtg atgctgtgtt gcttgtgttt                          400
```

<210> SEQ ID NO 23
<211> LENGTH: 550
<212> TYPE: DNA
<213> ORGANISM: Arabidopsis thaliana

<400> SEQUENCE: 23

```
aaatggggtt gagtttcgcc aagctgttta gcaggctttt tgccaagaag gagatgcgaa     60
ttctgatggt tggtcttgat gctgctggta agaccacaat cttgtacaag ctcaagctcg    120
gagagattgt caccaccatc cctactattg gtttcaatgt ggaaactgtg aatacaaga    180 acattagttt caccgtgtgg gatgtcgggg gtcaggacaa gatccgtccc ttgtggagac    240
actacttcca gaacactcaa ggtctaatct ttgttgttga tagcaatgac agagacagag    300
ttgttgaggc tcgagatgaa ctccacagga tgctgaatga ggacgagctg cgtgatgctg    360
tgttgcttgt gtttgccaac aagcaagatc ttccaaatgc tatgaacgct gctgaaatca    420
cagataagct tggccttcac tccctccgtc agcgtcattg gtatatccag agcacatgtg    480
ccacttcagg tgaagggctt tatgaaggtc tggactggct ctccaacaac atcgctggca    540
aggcatgatg                                                            550
```

<210> SEQ ID NO 24
<211> LENGTH: 550
<212> TYPE: DNA
<213> ORGANISM: Oryza sativa

<400> SEQUENCE: 24

```
agatggggct cacgttcacg aagctgttca gccgcctctt cgccaagaag gagatgagga     60
tcctcatggt cggtctcgat gcggccggta aaaccaccat cctctacaag ctcaagctcg    120
gcgagatcgt caccactatc cccaccatcg gttttaatgt cgaaactgtt gagtacaaga    180
acattagctt caccgttgg gatgttggtg gtcaggacaa gatcaggccc ctgtggaggc    240
actatttcca gaacacccag ggcctcattt ttgttgtgga cagcaatgac agagagcgtg    300
ttgttgaggc cagggatgag ctccaccgta tgctgaatga ggatgagcta cgtgatgctg    360
tgctgctggt gtttgcaaac aaacaagatc ttcctaatgc catgaacgct gctgagatca    420
ccgacaagct tggtctgcac tccttgcgcc agcggcactg gtacatccag agcacatgtg    480
ctacctctgg tgaggggttg tatgaggggc ttgactggct ttccaacaac attgccaaca    540
aggcttgaag                                                            550
```

<210> SEQ ID NO 25
<211> LENGTH: 8
<212> TYPE: PRT
<213> ORGANISM: Arabidopsis thaliana

<400> SEQUENCE: 25

Gly Leu Asp Ala Ala Gly Lys Thr
 1               5

<210> SEQ ID NO 26
<211> LENGTH: 389
<212> TYPE: DNA
<213> ORGANISM: Arabidopsis thaliana

<400> SEQUENCE: 26

```
tggtcttgat gctgctggta agaccacaat cttgtacaag ctcaagctcg gagagattgt        60
caccaccatc cctactattg gtttcaatgt ggaaactgtg aatacaaga acattagttt       120
caccgtggga tgtcggggt caggacaaga tccgtccctt gtggagacac tacttccaga       180
acactcaagg tctaatcttt gttgttgata gcaatgacag agacagagtt gttgaggctc       240
gagatgaact ccacaggatg ctgaatgagg acgagctgcg tgatgctgtg ttgcttgtgt       300
ttgccaacaa gcaagatctt ccaaatgcta tgaacgctgc tgaaatcaca gataagcttg       360
gccttcactc cctccgtcag cgtcattgg                                         389
```

<210> SEQ ID NO 27
<211> LENGTH: 391
<212> TYPE: DNA
<213> ORGANISM: N. benthiamiana

<400> SEQUENCE: 27

```
cggtcttgat gcagctggta aaaccaccat attgtacaag ctcaagctgg gagagatagt        60
taccactatt cctaccattg gattcaatgt ggagactgtt gaatacaaga acataagctt       120
cacggtctgg gatgttggtg gtcaggacaa gatccgacca ttgtggaggc attacttcca       180
aaacacacaa ggacttatct ttgtggtcga tagtaatgat cgtgatcgtg ttgttgaggc       240
tagagatgag ctgcaccgga tgttaatga ggatgaactg agggatgctg tgctgcttgt        300
gtttgctaac aagcaagatc ttccaaatgc tatgaatgct gctgagatta ctgacaagct       360
tggtcttcat tctctccgtc aacgtcactg g                                      391
```

<210> SEQ ID NO 28
<211> LENGTH: 26
<212> TYPE: DNA
<213> ORGANISM: N. benthiamiana

<400> SEQUENCE: 28

```
aagaaggaga tgcgaattct gatggt                                             26
```

<210> SEQ ID NO 29
<211> LENGTH: 26
<212> TYPE: DNA
<213> ORGANISM: N. benthiamiana

<400> SEQUENCE: 29

```
atgttgttgg agagccagtc cagacc                                             26
```

<210> SEQ ID NO 30
<211> LENGTH: 750
<212> TYPE: DNA
<213> ORGANISM: Arabidopsis thaliana

<400> SEQUENCE: 30

```
tttcgatcta aggttcgtga tctccttctt ctctacgaag tttacacttt ttcttcaaag        60
gaaacaatga gccagtacaa tcaacctccc gttggtgttc ctcctcctca aggttatcca       120
ccggagggat atccaaaaga tgcttatcca ccacaaggat atcctcctca gggatatcct       180
cagcaaggct atccacctca gggatatcct caacaaggtt atcctcagca aggatatcct       240
ccaccgtacg cgcctcaata tcctccacca ccgcaagcat cagcaacaac agagcaagtc       300
ctggctttct agaaggatgt cttgctgctc tgtgttgttg ctgtctcttg gatgcttgct       360
tctgattgga gtctctctct ctctgcataa agcttcggga tttatttgta agagggtttt       420
```

-continued

```
tgggttaaac aaaaacctta attgatttgt ggggcattaa aaatgaatct ctcgatgatt      480
ctcttcgttt atgtggtaat gttcttcggt tataacattt aacattgcta tcgacgttct      540
gcctagttgg atttgattat tgggaatgta aattggttgg aagacaccg ggccgttaat       600 gacagaaccc gaactgagat ggagtatgat ctgaaatatt taaacaatc ctcgcgacat       660 agcctccaat ctcatcgtaa atattctttt taaactattc ccaatcttaa cttttatagt     720
ctggtcgact gaccactact cttttccctt                                       750
```

<210> SEQ ID NO 31
<211> LENGTH: 543
<212> TYPE: DNA
<213> ORGANISM: Arabidopsis thaliana

<400> SEQUENCE: 31

```
cttaaaagca atatgacagt agagaagatc tctcacaaaa gacccaaaat cgagtcgtgc       60
aaaattgtac gaacaacaaa atttaaaatt cagtccttat caaagatcca atccagctgc     120
aactagcaac attggcttaa cgcttcttag acacaccaac agtctttcct ctgcgaccag     180
ttgtcttggt gtgttgtcca cgaacacgga gaccccagta atgtctcaga ccacgatggt     240
ttctgatttt cttgagacgc tcaagatcat ccctgagctt catgtcaagg cattggaga      300 caacttgaga gtacttccca tccttgtaat ctttctgtct gttcaaaaac cagtctggaa    360
tcttgaactg tcttgggttt gcaacaatag tcatgaggtt gtcaatctca gctgcagata    420
actcaccagc cctcttgttc atgtcgacat cggctttctt gcagacaatg ttggccaatc    480
tccttccaat acctttgata gaggtaaggg caaacataat cttttgctta ccatcaacgg    540
tag                                                                   543
```

<210> SEQ ID NO 32
<211> LENGTH: 757
<212> TYPE: DNA
<213> ORGANISM: Arabidopsis thaliana

<400> SEQUENCE: 32

```
ctgacataag ttatgttctt tgcgaaaata aaagttattc cacaaacgca ttcgataaaa      60
cattcaaaac cttcttcaga gtctaatccg tgaactgatg atcgatatag cttcacacta     120
tatatcctct tcacttctta gacttcttct tcggtacagc tgcagttgga gcaggtgtag     180
cagcaggtgc tggagcagct acaggcgcaa catctccacc gggacccctta gctaaacgct    240 cctctctcct agcatgcttc cttttctcggc tagccttgtt cttcgccctc ttagcctcaa    300
actgatcaag acagagtctt ctccctagcc ttctcaagcc tttgacttgt ggatactctc    360
catcaagaca cgcttgttct tgaacacatt tacccttaac acgcatgtac atggtcatgg    420
tacatgtgct tgtcaatctt ctttcgtctc tctggatttc ttcaaacaga cgcctaagaa    480
acacgccttc ctacgcattc cacagtacct tggttggga acctaactta cgggtacccc     540
ttccttttaa ccgattccag agtggcgacc ctttatcttg caatcttca ttttgcgagc    600 ttggaacaag agtgaatctt gggtggcttc tgatgatgaa acctctttaa actttctgag    660
gttttggcgg aaatggctga aacggatttg tgggaccaac caaattgcct ttcggcttaa    720
tactgatgcg accgtttgag taaaaaccgc cttcagg                             757
```

<210> SEQ ID NO 33
<211> LENGTH: 11
<212> TYPE: DNA

-continued

<213> ORGANISM: Tobacco mosaic virus

<400> SEQUENCE: 33
tatagtattt t                                                                11

<210> SEQ ID NO 34
<211> LENGTH: 11
<212> TYPE: DNA
<213> ORGANISM: Tobacco mosaic virus

<400> SEQUENCE: 34
tataggtatt t                                                                11

<210> SEQ ID NO 35
<211> LENGTH: 11
<212> TYPE: DNA
<213> ORGANISM: Tobacco mosaic virus
<220> FEATURE:
<221> NAME/KEY: misc_feature
<222> LOCATION: (1)...(11)
<223> OTHER INFORMATION: n= a, t, c, or g

<400> SEQUENCE: 35
tatagntatt t                                                                11

<210> SEQ ID NO 36
<211> LENGTH: 13
<212> TYPE: DNA
<213> ORGANISM: Tobacco mosaic virus
<220> FEATURE:
<221> NAME/KEY: misc_feature
<222> LOCATION: (1)...(12)
<223> OTHER INFORMATION: n= a, t, c or g

<400> SEQUENCE: 36
tatagtngta ttt                                                              13

<210> SEQ ID NO 37
<211> LENGTH: 12
<212> TYPE: DNA
<213> ORGANISM: Tobacco mosaic virus

<400> SEQUENCE: 37
tataggtatt tt                                                               12

<210> SEQ ID NO 38
<211> LENGTH: 14
<212> TYPE: DNA
<213> ORGANISM: Tobacco mosaic virus

<400> SEQUENCE: 38
tatagtcgta tttt                                                             14

<210> SEQ ID NO 39
<211> LENGTH: 15
<212> TYPE: DNA
<213> ORGANISM: Tobacco mosaic virus
<220> FEATURE:
<221> NAME/KEY: misc_feature
<222> LOCATION: (1)...(15)
<223> OTHER INFORMATION: n= a. t, c or g

<400> SEQUENCE: 39
tatagtngtn gtatt                                                            15

<210> SEQ ID NO 40

```
<211> LENGTH: 21
<212> TYPE: DNA
<213> ORGANISM: Tobacco mosaic virus
<220> FEATURE:
<221> NAME/KEY: misc_feature
<222> LOCATION: (1)...(21)
<223> OTHER INFORMATION: n= a, t, c or g

<400> SEQUENCE: 40
tatagtngtn gtngtngtat t                                     21

<210> SEQ ID NO 41
<211> LENGTH: 16
<212> TYPE: DNA
<213> ORGANISM: Tobacco mosaic virus

<400> SEQUENCE: 41
tatagtattt gtattt                                           16

<210> SEQ ID NO 42
<211> LENGTH: 12
<212> TYPE: DNA
<213> ORGANISM: Tobacco mosaic virus

<400> SEQUENCE: 42
tatagtcgta tt                                               12
```